US012773391B2

(12) United States Patent
Gindy et al.

(10) Patent No.: US 12,773,391 B2
(45) Date of Patent: Oct. 27, 2026

(54) LIPID NANOPARTICLE COMPOSITIONS CONTAINING MONOESTER CATIONIC LIPIDS

(71) Applicant: Merck Sharp & Dohme LLC, Rahway, NJ (US)

(72) Inventors: Marian E. Gindy, Haledon, NJ (US); Andrew Bett, Lansdale, PA (US); Izzat Tiedje Raheem, Doylestown, PA (US); Ronald M. Kim, Summit, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 407 days.

(21) Appl. No.: 18/254,898

(22) PCT Filed: Dec. 1, 2021

(86) PCT No.: PCT/US2021/061336
§ 371 (c)(1),
(2) Date: May 30, 2023

(87) PCT Pub. No.: WO2022/119883
PCT Pub. Date: Jun. 9, 2022

(65) Prior Publication Data

US 2024/0050378 A1 Feb. 15, 2024

Related U.S. Application Data

(60) Provisional application No. 63/120,449, filed on Dec. 2, 2020.

(51) Int. Cl.
*A61K 9/51* (2006.01)
*A61K 31/7088* (2006.01)

(52) U.S. Cl.
CPC .......... *A61K 9/5123* (2013.01); *A61K 9/5146* (2013.01); *A61K 31/7088* (2013.01)

(58) Field of Classification Search
CPC . A61K 9/5123; A61K 9/5146; A61K 31/7088
See application file for complete search history.

(56) References Cited

U.S. PATENT DOCUMENTS

| | | | |
|---|---|---|---|
| 5,208,036 | A | 5/1993 | Eppstein et al. |
| 5,264,618 | A | 11/1993 | Felgner et al. |
| 5,279,833 | A | 1/1994 | Rose |
| 5,283,185 | A | 2/1994 | Epand et al. |
| 6,890,557 | B2 | 5/2005 | Huang et al. |
| 7,691,405 | B2 | 4/2010 | Chen et al. |
| 8,952,955 | B2 | 2/2015 | Yokoyama et al. |
| 9,669,097 | B2 | 6/2017 | Stanton et al. |
| 2008/0057080 | A1 | 3/2008 | Luke et al. |
| 2008/0085870 | A1 | 4/2008 | Hermanson et al. |
| 2009/0263407 | A1 | 10/2009 | Dande et al. |
| 2009/0285881 | A1 | 11/2009 | Dande et al. |
| 2010/0055168 | A1 | 3/2010 | Dande et al. |
| 2010/0055169 | A1 | 3/2010 | Dande et al. |
| 2010/0063135 | A1 | 3/2010 | Dande et al. |
| 2010/0076055 | A1 | 3/2010 | Dande et al. |
| 2010/0099738 | A1 | 4/2010 | Hansen et al. |
| 2010/0104629 | A1 | 4/2010 | Dande et al. |
| 2013/0017239 | A1 | 1/2013 | Petit et al. |
| 2016/0361411 | A1 | 12/2016 | Gindy et al. |
| 2017/0296469 | A1 | 10/2017 | Kaufmann et al. |

FOREIGN PATENT DOCUMENTS

| | | | | | |
|---|---|---|---|---|---|
| WO | 2009132131 | A1 | | 10/2009 | |
| WO | 2010/021865 | A1 | | 2/2010 | |
| WO | 2010042877 | A1 | | 4/2010 | |
| WO | 2010105209 | A1 | | 9/2010 | |
| WO | 2010146740 | A1 | | 12/2010 | |
| WO | 2011022460 | A1 | | 2/2011 | |
| WO | 2011076807 | A2 | | 6/2011 | |
| WO | 2012040184 | A2 | | 3/2012 | |
| WO | WO-2012170930 | A1 | * | 12/2012 | ................ A61P 7/06 |
| WO | WO-2013059496 | A1 | * | 4/2013 | .............. A61P 35/00 |
| WO | 2013086354 | A1 | | 6/2013 | |
| WO | WO-2013116126 | A1 | * | 8/2013 | .............. C08L 91/00 |
| WO | 2014089486 | A1 | | 6/2014 | |
| WO | 2017112865 | A1 | | 6/2017 | |
| WO | 2017192470 | A1 | | 11/2017 | |
| WO | 2018170336 | A1 | | 9/2018 | |
| WO | 2020072324 | A1 | | 4/2020 | |
| WO | 2020191103 | A1 | | 9/2020 | |

OTHER PUBLICATIONS

Google Search; is a siRNA lipid nanoparticle suitable as a vaccine (accessed Jul. 2025) (Year: 2025).*
Hassett, Kimberly J. et al., Optimization of Lipid Nanoparticles for Intramuscular Administration of mRNA Vaccines, Mol. Ther., 2019, 1-11, 15.
Maier, Martin A et al., Biodegradable Lipids Enabling Rapidly Eliminated Lipid Nanoparticles for Systemic Delivery of RNAi Therapeutics, Mol. Ther., 2013, 1570-1578, 21(8).
Zhi, Defu et al., A review on cationic lipids with different linkers for gene delivery, Advances in Colloid and Interface Science, 2018, 117-140, 253.
Guevara, Maria L. et al., Advances in Lipid Nanoparticles for mRNA-Based Cancer Immunotherapy, Frontiers in Chemistry, 8, 1-17, 2020.

* cited by examiner

*Primary Examiner* — Robert A Wax
*Assistant Examiner* — John W Lippert, III
(74) *Attorney, Agent, or Firm* — Matthew A. Leff; Emily K. Sauter

(57) ABSTRACT

The present disclosure provides, among other things, lipid nanoparticle formulations that include monoester cationic lipids. The present invention also provides compositions that include monoester cationic lipid nanoparticles and nucleic acids. The present disclosure also provides lipid nanoparticles encapsulating agents. The present disclosure further provides methods of producing lipid nanoparticles with encapsulated nucleic acids.

7 Claims, 14 Drawing Sheets

| Formulation | Geomean |
|---|---|
| 9 | 178.3 |
| 10 | 112.3 |
| 11 | 130.6 |
| 13 | 72.6 |

| Formulation | Geomean |
|---|---|
| 12 | 278.8 |
| 8 | 1.5 |

| Formulation | Geomean |
|---|---|
| 12 | 256 |
| 6 | 413 |
| 3 | 115 |

LIPID NANOPARTICLE COMPOSITIONS CONTAINING MONOESTER CATIONIC LIPIDS

This application is a § 371 National Phase Application of International Application No. PCT/US2021/061336, filed Dec. 1, 2021, which claims the benefit of priority to U.S. Provisional Application No. 63/120,449, filed Dec. 2, 2020, the contents of which are hereby incorporated by reference in their entirety.

FIELD OF THE INVENTION

The present disclosure provides, among other things, compositions that include lipid nanoparticles. The present disclosure also provides lipid nanoparticles that encapsulate agents. The present disclosure further provides methods of producing lipid nanoparticles capable of encapsulating agents, such as polynucleotides.

BACKGROUND

In recent years, various biomedical applications of nanoparticle platforms have been explored. Lipid nanoparticles ("LNP") are a nanoparticle technology useful, e.g., for the delivery of an agent to a subject. For example, delivery of agents such as polynucleotides, including small interfering RNA (siRNA), mRNA, or plasmid DNA, in LNPs provide potential therapies and vaccines for many diseases, e.g., by silencing pathological genes, expressing therapeutic proteins or antigens, or through gene-editing applications.

The primary challenges associated with development of this technology are the optimization of activity and safety characteristics to meet a defined product profile consistent with intended use as therapeutic or vaccine, the disease indication, route of administration, and target patient or subject population. Protection of the administered agent, especially, e.g., in the delivery of polynucleotide agents, protecting the polynucleotide from nuclease degradation, effective modulation of biodistribution, pharmacokinetics, intracellular delivery to target cells, immunogenic profile, and safety or tolerability, both systemic and local depending on route of administration, are critical to product optimization. Further, due to the chemical-physical properties (e.g., high MW, high charge density, enzymatic lability, etc.) of polynucleotides, most polynucleotides require drug delivery systems and formulations for in vivo use.

LNPs have emerged as promising delivery systems for polynucleotide-based therapeutics and vaccines. LNPs may include multiple components, such as one or more cationic lipids, a neutral lipid, a steroid, and a polymer conjugated lipid, where the polynucleotide of interest is encapsulated within the LNP. While several LNP systems have been reported, their design has largely been focused on in vivo delivery of therapeutic siRNA to down-regulate the synthesis of disease-associated proteins through RNA interference (RNAi) process. These siRNA-LNPs have been primarily leveraged for liver-associated disease targets and administered systemically via intravenous ("IV") route.

The optimization of LNPs for use as systemic delivery vehicles of siRNA has focused primarily on the discovery of novel cationic lipids that improve intracellular delivery and/or endosomal escape of the encapsulated polynucleotide when formulated as part of LNPs. Additionally, LNPs incorporating monoester cationic lipid components have been developed to facilitate lipid elimination from the liver and improve systemic safety profiles.

With recent interest in mRNA polynucleotides as a treatment modality, LNPs have found applications in mRNA-based therapeutics and vaccines. In general, LNPs used for mRNA therapeutics and/or vaccines have relied on LNPs originally designed for delivery of siRNA or related polynucleotides. However, these LNP systems are not necessarily optimized for mRNA applications. For example, effective mRNA delivery requires an LNP system optimized for robust expression of mRNA-encoded protein when administered to a subject, often via intramuscular ("IM") or intradermal ("ID") routes. The LNP must also be tolerated, locally, at the site of administration, and systemically consistent with use within a specific indication and target population.

Lipid components capable of being rapidly eliminated from plasma and tissues are desirable components for systemically-administered LNP delivery systems due to improved systemic tolerability. See, e.g., Maier M A, Jayaraman M, Matsuda S, et al., "Biodegradable Lipids Enabling Rapidly Eliminated Lipid Nanoparticles for Systemic Delivery of RNAi Therapeutics", *Mol Ther.* 2013; 21(8):1570-1578. doi:10.1038/mt.2013.124. However, there remains a need for improved LNP systems for delivery of polynucleotide actives intended for local routes of administration (e.g., intramuscular, intradermal, intratumoral, intranasal, intraocular, etc.).

SUMMARY

The present invention provides a composition comprising:

a polynucleotide; and a lipid nanoparticle (LNP) comprising:

(a) a monoester cationic lipid having the structure set forth in Formula D:

Formula D

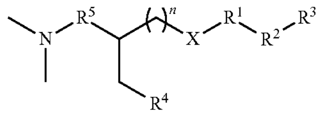

wherein, $R^3$ is $C_1$-$C_{12}$alkyl, X—$R^1$—$R^2$, $R^1$—X—$R^2$ or absent;

$R^4$ is $C_1$-$C_{12}$alkyl, $C_1$-$C_{12}$ heteroalkyl, or absent;

$R^5$ is $C_1$-$C_{12}$alkyl;

each X is independently,

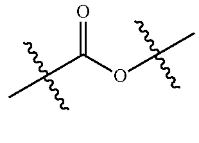
,
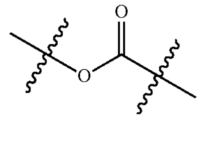
, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent;

and n is 0-12;

(b) a phospholipid;

(c) cholesterol; and (d) a PEG-lipid;

wherein the polynucleotide is at least partially encapsulated in the LNP.

The present invention also provides a composition comprising:

a polynucleotide; and a lipid nanoparticle (LNP) comprising:

(a) a monoester cationic lipid having the structure set forth in Formula E:

Formula E

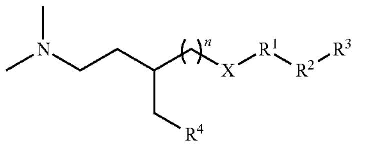

wherein, $R^3$ is $C_1$-$C_{12}$ alkyl, X—$R^1$—$R^2$, $R^1$—X—$R^2$ or absent;

$R^4$ is $C_1$-$C_{12}$ alkyl, $C_1$-$C_{12}$ heteroalkyl, or absent;

each X is independently

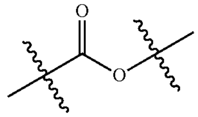 [SMILES: *OC(*)=O]

,

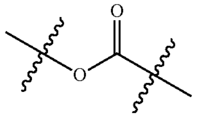

, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent;

and n is 0-12;

(b) a phospholipid;

(c) cholesterol; and (d) a PEG-lipid;

wherein the polynucleotide is at least partially encapsulated in the LNP.

The present invention also provides a composition comprising:

a polynucleotide; and a lipid nanoparticle (LNP) comprising:

(a) a monoester cationic lipid having the structure set forth in Formula F:

Formula F

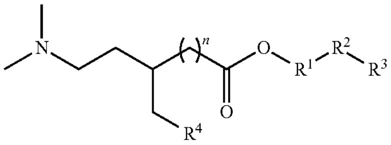

wherein, $R^1$ is $C_1$-$C_{12}$ alkyl;

$R^2$ is cis-alkenyl;

$R^3$ is $C_1$-$C_{12}$ alkyl;

$R^4$ is $C_1$-$C_{12}$ alkyl; and n is 0-12;

(b) a phospholipid;

(c) cholesterol; and (d) a PEG-lipid;

wherein the polynucleotide is at least partially encapsulated in the LNP.

The present invention also provides a composition comprising:

a polynucleotide, and a lipid nanoparticle (LNP) comprising:

(a) a monoester cationic lipid selected from the group consisting of:

(20Z,23Z)-nonacosa-20,23-dien-10-yl 3-(dimethylamino)-propanoate;

(Z)-undec-2-en-1-yl 8-(2-(dimethylamino)ethyl)heptadecanoate;

(Z)-non-2-en-1-yl 10-(2-(dimethylamino)ethyl)nonadecanoate;

(Z)-tridec-2-en-1-yl 6-(2-(dimethylamino)ethyl)pentadecanoate;

pentyl (14Z,17Z)-4-(2-(dimethylamino)ethyl)tricosa-14,17-dienoate;

(Z)-oct-2-en-1-yl 11-(2-(dimethylamino)ethyl)icosanoate;

(Z)-hept-2-en-1-yl 12-(2-(dimethylamino)ethyl)henicosanoate;

methyl (Z)-18-(2-(dimethylamino)-ethyl)heptacos-7-enoate;

and combinations thereof, (b) a phospholipid, (c) cholesterol, and (d) a PEG-lipid, wherein the polynucleotide is at least partially encapsulated in the LNP.

The invention also provides a composition comprising:

a buffer;

a polynucleotide; and a lipid nanoparticle comprising:

(a) a phospholipid;

(b) cholesterol;

(c) a PEG-lipid; and (d) a monoester cationic lipid having the structure set forth in Formula D:

Formula D

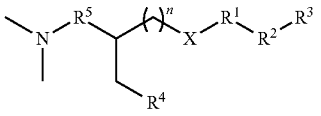

wherein, $R^3$ is $C_4$-$C_{10}$ alkyl, $R^1$—X—$R^2$ or absent;

$R^4$ is $C_5$-$C_8$ alkyl or absent;

$R^5$ is $C_2$ alkyl;

each X is independently

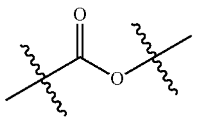 [SMILES: *OC(*)=O]

or cis-alkenyl;

each $R^1$ is independently $C_1$-$C_5$ alkyl or absent;

each $R^2$ is independently $C_1$ alkyl, cis-alkenyl, or absent;

and n is 4, 6, 8, 9, or 10, wherein the polynucleotide is at least partially encapsulated in the lipid nanoparticle.

The invention also provides a composition comprising:

a buffer;

a polynucleotide; and a lipid nanoparticle, wherein the lipid nanoparticle comprises:

(a) a phospholipid;

(b) cholesterol;

(c) a PEG-lipid; and (d) a monoester cationic lipid having the structure set forth in Formula F:

Formula F

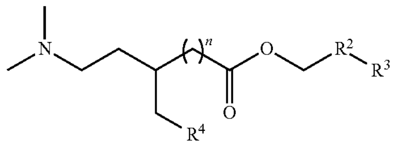

wherein, $R^2$ is cis-alkenyl;

$R^3$ is $C_4$-$C_{10}$ alkyl;

$R^4$ is $C_5$-$C_8$ alkyl or absent; and n is 4, 6, 8, 9, or 10;

wherein the polynucleotide is at least partially encapsulated in the lipid nanoparticle.

The present invention also provides a composition comprising:

a buffer;

a polynucleotide; and a lipid nanoparticle, wherein the lipid nanoparticle comprises:

(a) a phospholipid;

(b) cholesterol;

(c) a PEG-lipid; and (d) a monoester cationic lipid selected from the group consisting of:

(20Z,23Z)-nonacosa-20,23-dien-10-yl 3-(dimethylamino)-propanoate; (Z)-undec-2-en-1-yl 8-(2-(dimethylamino)ethyl)heptadecanoate; (Z)-non-2-en-1-yl 10-(2-(dimethylamino)ethyl) nonadecanoate; (Z)-tridec-2-en-1-yl 6-(2-(dimethylamino)ethyl)pentadecanoate; pentyl (14Z,17Z)-4-(2-(dimethylamino)ethyl)tricosa-14,17-dienoate; (Z)-oct-2-en-1-yl 11-(2-(dimethylamino)ethyl)icosanoate; (Z)-hept-2-en-1-yl 12-(2-(dimethylamino)ethyl)henicosanoate; and methyl (Z)-18-(2-(dimethylamino)-ethyl)heptacos-7-enoate;

wherein the polynucleotide is at least partially encapsulated in the lipid nanoparticle; and wherein the composition formulated with the monoester cationic lipid provides improved tolerability compared to the same composition formulated without the monoester cationic lipid.

Definitions

The following abbreviations are used herein:

ACN acetonitrile
AcOH or HOAc acetic acid
anh anhydrous
aq aqueous
Bn benzyl
brine saturated aqueous NaCl
Bz benzoyl
calc'd calculated
CAN ceric ammonium nitrate
Celite diatomaceous earth
DCM dichloromethane
DIEA or DIPEA N,N-diisopropylethylamine
DMAP 4-dimethylaminopyridine
DMF N, N-dimethylformamide
DMP Dess-Martin periodinane
DMSO dimethyl sulfoxide
EDCI 1-ethyl-3-(3-dimethylaminopropyl)carbodiimide
EDTA ethylenediamine tetraacetic acid
ESI electrospray ionization
Et ethyl
$Et_2O$ diethyl ether
EtOH ethanol
EtOAc ethyl acetate
$Et_3N$ triethylamine
h hour
HPLC high-performance liquid chromatography
IPA isopropanol
iPr isopropyl
LC liquid chromatography
LCMS liquid chromatography mass spectrometry
MeOH methanol
mg milligrams
min minutes
L microliters
mL milliliters
mmol millimoles
MS mass spectrometry
NBS N-bromosuccinimide
NMR nuclear magnetic resonance spectroscopy
PBS phosphate buffered saline
PDC pyridinium dichromate
Pet. ether petroleum ether
Ph phenyl
Pr propyl
PS polystyrene
Rac racemic mixture
RT or rt room temperature
Sat saturated
SFC supercritical fluid chromatography
TBAF tert-butyl ammonium fluoride
TBS or TBDMS tert-butyldimethylsilyl
TBSCl tert-butyldimethylsilyl chloride
t-Bu tert-butyl
TEA triethylamine
TBAI tetrabutyl ammonium iodide
TBDPS tert-butyldiphenylsilyl
TBDPSCl tert-butyldiphenylsilyl chloride
TFA trifluoroacetic acid
THF tetrahydrofuran
TLC thin layer chromatography
TMS trimethylsilyl The wavy line 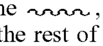, as used herein, indicates a point of attachment to the rest of the compound.

About: As used herein, the term "about," when used herein in reference to a value, refers to a value that is the same as or, in context, is similar to the referenced value. In general, those skilled in the art, familiar with the context, will appreciate the absolute amount and/or relative degree of difference encompassed by "about" in that context. For example, in some embodiments, the term "about" can encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referenced value.

Administration: As used herein, the term "administration," "administering," or "administered" refers to the act of providing an active agent, composition, or formulation to a subject, e.g., a human. Exemplary routes of administration to the human body can be through the eyes (ophthalmic), mouth (oral), skin (transdermal), nose (nasal), lungs (inhalant), rectal, vaginal, oral mucosa (buccal), ear, by injection (e.g., intravenously (IV), subcutaneously, intratumorally, intraperitoneally, intramuscular (IM), intradermal (ID) etc.) and the like.

Agent: As used herein, the term "agent" refers to a particle, compound, molecule, or entity of any chemical class including, for example, a small molecule, polypeptide (e.g., a protein), polynucleotide (e.g., a DNA polynucleotide or an RNA polynucleotide), saccharide, lipid, or a combination or complex thereof. In some embodiments, the term "agent" can refer to a compound, molecule, or entity that includes a polymer, or a plurality thereof. In some embodiments, the term "agent" in general may refer to an agent that elicits a desired pharmacological effect when administered to an organism. In some embodiments, the agent may be used to prevent the spread of a disease. In some embodiments, the term refers to an agent intended for use as a prophylactic. In some embodiments, the prophylactic agent is a vaccine.

Alkyl and Alkenyl: As used herein, the term "alkyl" refers to a straight chain, cyclic or branched saturated aliphatic hydrocarbon having the specified number of carbon atoms, e.g., $C_1$ is methyl and $C_2$ is ethyl. In different embodiments, an alkyl group contains from 1 to 12 carbon atoms ($C_1$-$C_{12}$ alkyl); from 4 to 10 carbon atoms ($C_4$-$C_{10}$ alkyl); from 5 to 8 carbon atoms ($C_5$-$C_8$ alkyl). In one embodiment, an alkyl group is linear. In another embodiment, an alkyl group is branched. Unless otherwise indicated, an alkyl group is unsubstituted. As used herein, the term "alkenyl" means a straight chain, cyclic or branched unsaturated aliphatic hydrocarbon having the specified number of carbon atoms including but not limited to diene, triene and tetraene unsaturated aliphatic hydrocarbons.

Antigen: As used herein, the term "antigen" refers to any antigen that can generate one or more immune responses. The antigen may be a protein (including recombinant proteins), VLP, polypeptide, or peptide (including synthetic peptides). In certain embodiments, the antigen is a lipid or a carbohydrate (polysaccharide). In certain embodiments, the antigen is a protein extract, cell (including tumor cell), or tissue. The antigen may be one that generates a humoral and/or CTL immune response.

API: As used herein, the term "API" refers to an active pharmaceutical ingredient, which is a component of the compositions or formulations disclosed herein that is biologically active (e.g., capable of inducing an appropriate immune response) and confers a therapeutic or prophylactic benefit to a person or animal in need thereof. As used herein, an API can be a vaccine active ingredient.

Biomarker: As used herein, the term "biomarker" refers to an entity whose presence, level, or form, correlates with a particular biological event or state of interest, so that it is considered to be a "marker" of that event or state. For example, in some embodiments, a biomarker can be or include a marker for a particular adverse event or other biological outcome, or a marker that predicts the likelihood that a particular adverse event or other biological outcome will develop, occur, or reoccur. Thus, in some embodiments a biomarker is predictive, in some embodiments a biomarker is prognostic, and in some embodiments a biomarker is diagnostic, of a relevant event, adverse event or other biological outcome. A biomarker can be an entity of any chemical class. For example, in some embodiments, a biomarker can be or include a polynucleotide, a polypeptide, a lipid, a carbohydrate, a small molecule, an inorganic agent (e.g., a metal or ion), a symptom of an adverse event, or a combination thereof. In some embodiments, a biomarker is intracellular. In some embodiments, a biomarker is found outside of cells (e.g., is secreted or is otherwise generated or present outside of cells, e.g., in a body fluid such as blood, urine, tears, saliva, cerebrospinal fluid, etc. In some embodiments, a biomarker can be assessed by physical examination.

Cationic lipid: As used herein, the term "cationic lipid" refers to a lipid species that carries a net positive charge at a selected pH, such as physiological pH. Those of skill in the art will appreciate that a cationic lipid can be an ionizable lipid, such as an ionizable cationic lipid. Such lipids include, but are not limited to, the cationic lipids that are disclosed in U.S. Patent Application Publication Nos. US 2009/0263407, US 2009/0285881, US 2010/0055168, US 2010/0055169, US 2010/0063135, US 2010/0076055, US 2010/0099738, US 2010/0104629, US 2016/0361411, US2008/0085870, US2008/0057080, and US2013/0017239, International Patent Application Publication Nos. WO2011/022460; WO2012/040184, WO2011/076807, WO2010/021865, WO 2009/132131, WO2010/042877, WO2010/146740, and WO2010/105209, and in U.S. Pat. Nos. 5,208,036, 5,264,618, 5,279,833, 5,283,185, 6,890,557, and 9,669,097.

Cis-alkenyl: As used herein, the term "cis-alkenyl" refers to a double bond comprised of two carbons where the substituent of either end of the double bond are cis to one another.

Compositions: As used herein, the term "composition" refers to an active agent in combination with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a composition can be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Effective amount: As used herein, the term "effective amount" refers to an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, an effective amount is one that reduces the incidence and/or severity of, and/or delays onset of, one or more symptoms of the disease, disorder, and/or condition. Those of ordinary skill in the art will appreciate that the term "effective amount" does not in fact require successful treatment be achieved in a particular subject. Rather, an effective amount can be that amount that provides a particular desired pharmacological response in a significant number of subjects when administered to subjects in need of such treatment. In some embodiments, reference to an effective amount can be a reference to an amount as measured in one or more specific tissues (e.g., a tissue affected by the disease, disorder, or condition) or fluids (e.g., blood, saliva, serum, sweat, tears, urine, etc.). Those of ordinary skill in the art will appreciate that, in some embodiments, an effective amount of a particular agent or therapy can be formulated and/or administered in a single dose. In some embodiments, an effective agent can be formulated and/or administered in a plurality of doses, for example, as part of a dosing regimen.

Encapsulated or Encapsulation: As used herein, the term "encapsulated" or "encapsulation" refers to the process or result of confining one or more agents, such as one or more polynucleotides, within a nanoparticle. As used herein, the terms "encapsulation" and "loading" can be used interchangeably. The agent may be fully encapsulated or partially encapsulated. An agent that is at least partially encapsulated by a carrier if at least a portion of the molecule or particle is confined within the carrier (e.g., for example within a pore of the carrier).

Expression: As used herein, "expression" refers to one or more biological processes that result in production of a polypeptide from a polynucleotide sequence, specifically including either or both of transcription and translation.

Formulation: As used herein, the term "formulation" refers to a composition containing an active pharmaceutical or biological ingredient, along with one or more additional components. The formulations can be liquid or solid (e.g., lyophilized). Additional components that may be included as appropriate include pharmaceutically acceptable excipients, additives, diluents, buffers, sugars, amino acids, chelating agents, surfactants, polyols, bulking agents, stabilizers, lyoprotectants, solubilizers, emulsifiers, salts, adjuvants, tonicity enhancing agents, delivery vehicles, and anti-microbial preservatives. Formulations are nontoxic to recipients at the dosages and concentrations employed. In some embodiments, the formulation refers to a single-dose of vaccine, which can be included in any volume suitable for injection.

Half-life: As used herein, the term "half-life" refers to the time it takes for the concentration of an active pharmaceutical ingredient to reduce to its original value by half. Systemic half-life refers to the time it takes for plasma concentration of the active pharmaceutical ingredient to reduce to half its original value. Local half-life refers to the time it takes for local tissue concentration of the active pharmaceutical ingredient to reduce to half its original value.

Heteroalkyl: As used herein, the term "heteroalkyl" refers to an alkyl moiety as defined above, having one or more carbon atoms, for example one, two or three carbon atoms, replaced with one or more heteroatoms, which may be the same or different, where the point of attachment to the remainder of the molecule is through a carbon atom of the heteroalkyl radical. Suitable such heteroatoms include O, S, S(O), $S(O)_2$, and —NH—, —N(alkyl)-. Non-limiting examples include ethers, thioethers, amines, hydroxymethyl, 3-hydroxypropyl, 1,2-dihydroxyethyl, 2-methoxyethyl, 2-aminoethyl, 2-dimethylaminoethyl, and the like. In some embodiments, heteroalkyl may include an aliphatic group containing a heteroatom. In different embodiments, a heteroalkyl group contains from 1 to 12 carbon atoms ($C_1$-$C_{12}$ heteroalkyl). In one embodiment, a heteroalkyl group is linear. In another embodiment, a heteroalkyl group is branched.

Lipid: As used herein, the term "lipid" refers to any of a group of organic compounds that are esters of fatty acids and are characterized by being insoluble in water or having low solubility in water but may be soluble in many organic solvents. They can be divided in at least three classes: (1) "simple lipids," which include, e.g., fats and oils as well as waxes; (2) "compound lipids," which include, e.g., phospholipids and glycolipids; and (3) "derived lipids," which include, e.g., steroids.

Lipid nanoparticle: As used herein, the term "lipid nanoparticle" (or "LNP") refers to a lipid composition that forms a particle having a length or width measurement (e.g., a maximum length or width measurement) between 10 and 1000 nanometers. In some embodiments, the LNP may be used to deliver antigens, antibodies, APIs, and the like.

Monoester cationic lipid: As used herein, the term "monoester" refers to a cationic lipid containing only a single ester group.

Neutral lipid: As used herein, the term "neutral lipid" refers to a lipid species that exists either in an uncharged or neutral zwitterionic form at a selected pH. At physiological pH, such lipids include, for example, diaeylphosphatidylcholine, diacylphosphatidyletbanolamine, ceramide, sphingomyelin, cephalin, cholesterol, cerebrosides and diacylglycerols.

Nucleic acid: As used herein, "nucleic acid" refers to an individual nucleic acid molecule (e.g., a nucleotide or nucleoside). In some embodiments, a nucleic acid is or includes a natural nucleic acid (e.g., adenosine, thymidine, guanosine, cytidine, uridine, deoxyadenosine, deoxythymidine, deoxyguanosine, and deoxycytidine). In some embodiments a nucleic acid is an RNA or a DNA. In some embodiments, a nucleic acid is or includes a nucleic acid analog (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, and combinations thereof). In some embodiments, a nucleic acid analog differs from a typical nucleic acid in that the nucleic acid analog does not utilize a phosphodiester backbone for association with other nucleic acids of a polynucleotide. For example, in some embodiments, a nucleic acid is or includes a "peptide nucleic acid" known in the art to associate with other nucleic acids via a peptide bond backbone rather than via a phosphodiester bond backbone. In some embodiments, a nucleic acid includes a modified sugar (e.g., 2'-fluororibose, ribose, 2'-deoxyribose, arabinose, or hexose) as compared with a sugar of a natural nucleic acid.

Pharmaceutically acceptable: As used herein with respect to a carrier, diluent, or excipient of a composition, the term "pharmaceutically acceptable" indicates that a carrier, diluent, or excipient must be compatible with the other ingredients of the composition and not deleterious to the recipient thereof.

Polynucleotide: As used herein, the term "polynucleotide" refers to a molecule including two or more nucleic acids. In some embodiments, a polynucleotide is a DNA polynucleotide or an RNA polynucleotide. Examples of DNA polynucleotides can include antisense DNA, plasmid DNA, pre-condensed DNA, DNA produced by a polymerase chain reaction (PCR), vector DNA (P1, PAC, BAC, YAC, artificial chromosomes), a DNA aptamer, an expression cassette, a chimeric sequence, chromosomal DNA, or a form derivative thereof. Examples of RNA polynucleotides can include tRNA (transfer RNA), snRNA (small nuclear RNA), rRNA (ribosomal RNA), mRNA (messenger RNA), antisense RNA, siRNA (small interfering RNA), miRNA, shRNA (short hairpin RNA), ncRNA (non-coding RNA), an RNA aptamer, a ribozyme, a chimeric sequence, or a form derivative thereof. A polynucleotide can be single, double, triple, or quadruple stranded in its entirety or in any portion thereof. In some embodiments, a polynucleotide includes a phosphodiester backbone. In some embodiments, a polynucleotide includes a peptide bond backbone. In some embodiments, a polynucleotide includes one or more phosphorothioate linkages and/or 5'-N-phosphoramidite linkages, e.g., rather a phosphodiester bond. In some embodiments, a polynucleotide has a nucleotide sequence that encodes a functional gene product such as an RNA or protein. In some embodiments, a polynucleotide includes one or more introns. In some embodiments, a polynucleotide is prepared by one or more of isolation from a natural source, enzymatic synthesis by polymerization based on a complementary template (in vivo or in vitro), reproduction in a recombinant cell or system, and chemical synthesis. In some embodiments, a polynucleotide is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more nucleic acid residues long. In some embodiments a polynucleotide has a nucleotide sequence including at least one element that encodes, or is the complement of a sequence that encodes, all or a portion of a polypeptide. In some embodiments, a polynucleotide has enzymatic activity.

Secreted embryonic alkaline phosphatase ("SEAP"): As used herein, the term "SEAP" refers to secreted embryonic alkaline phosphatase protein that is a truncated form of human placental alkaline phosphatase. Those of skill in the art will appreciate that SEAP is expressed in CHO cells and shows a 75 kDa band on an SDS page gel. Recombinant SEAP protein is purified by affinity chromatography.

Sample: As used herein, the term "sample" typically refers to an aliquot of material obtained or derived from a source of interest. In some embodiments, a source of interest is a solution or an emulsion. In some embodiments, a source of interest is a reaction product, laboratory product, or manufactured product. In some embodiments, a source of interest is a biological or environmental source. In some embodiments, a source of interest can be or include a cell or an organism, such as a microbe, a plant, or an animal (e.g., a human). In some embodiments, a source of interest is or includes biological tissue or fluid. In some embodiments, a biological sample is or includes cells obtained from a subject. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" can include, for example polynucleotides or proteins extracted from a sample or obtained by subjecting a primary sample to one or more techniques such as amplification or reverse transcription of polynucleotide, isolation and/or purification of certain components, etc.

Subject: As used herein, the term "subject" refers an organism, typically a mammal (e.g., a human, in some embodiments including prenatal human forms). In some embodiments, a subject is suffering from a relevant disease, disorder, or condition. In some embodiments, a subject is susceptible to a disease, disorder, or condition. In some embodiments, a subject displays one or more symptoms or characteristics of a disease, disorder, or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Trans-alkenyl: As used herein, the term "trans-alkenyl" refers to a double bond comprised of two carbons where the substituent of either end of the double bond are trans to one another.

Tolerability: As used herein, the term "tolerability" refers to a quantitative or qualitative measure of the presence and/or degree of adverse effects caused by administration of an agent or composition (e.g., pharmaceutically acceptable composition or formulation) to a subject. In some embodiments, tolerability is assessed locally, e.g., at an administration site of a subject. In some embodiments, tolerability is assessed systemically, e.g., throughout the entire body. In some embodiments, tolerability may be measured as an improvement in a biomarker. In some instances, tolerability is or includes subjective or objective assessment of, e.g., pain, discomfort, nausea, fatigue, defecation activities, eating behaviors (e.g., anorexia), sleeping behaviors, hair loss, inflammation, swelling, rash, weight change, skin-related toxicities, quality of life, emotional status, or lifestyle impact. In some instances, tolerability is assessed by whether a practitioner continues, discontinues, interrupts, delays, updates dosage (e.g., reduces dosage) in, or otherwise revises a course of treatment. In some instances, assessing tolerability includes physical examination of a subject. In some instances, assessing tolerability includes assessing the presence and/or degree of medical adverse event(s), including without limitation emergency room visits, hospitalization, death, and/or any adverse event recognized by the U.S. Department of Health and Human Services Common Terminology Criteria for Adverse Events (CTCAE). In various embodiments, assessing tolerability includes assessing a biomarker. Those of skill in the art will appreciate that some or all assessments that can constitute or contribute to a determination of tolerability can be applied to human and/or non-human animal subjects, e.g., with respect to same or equivalent biological responses or events in non-human animal subjects.

Those of skill in the art will further appreciate that methods and/or standards for measuring adverse effects are known in the art.

DETAILED DESCRIPTION

Figure 1:
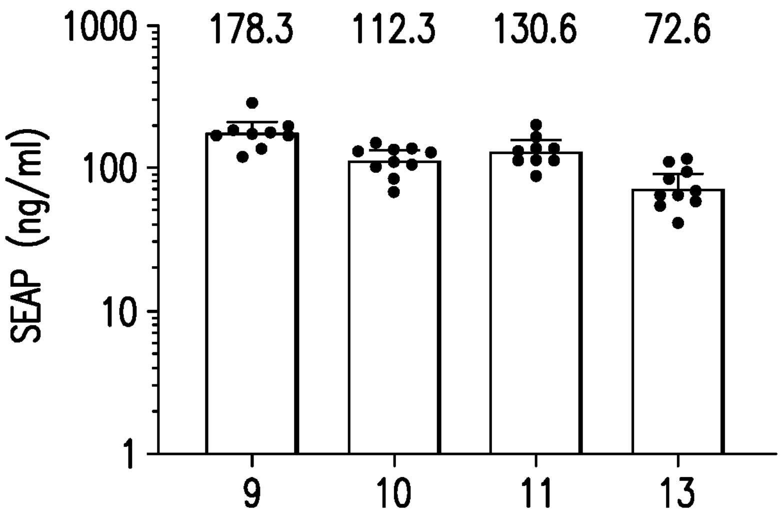
FIG. 1 is a graph depicting SEAP expression of LNP 9, 10, 11, and 13 of the present invention.

The present invention generally relates to compositions that include agents encapsulated in monoester cationic lipid based lipid nanoparticles (LNPs) for administration via parenteral routes (e.g., intramuscular ("IM"), subcutaneous ("SC"), intradermal ("ID"), intranasal, or intravenous ("IV")). In some embodiments, the agents may be polynucleotides. As shown herein, monoester cationic lipids, when formulated as part of an LNP, display short half-lives following in vivo administration to a subject, and exhibit increased tolerability at the site of administration of the LNP composition. Following in vivo administration to a subject, the monoester cationic lipids, as part of the LNP, display short half-lives and increased local tolerability, compared to LNPs formulated without monoester cationic lipids. The monoester cationic lipids, as part of the LNP, lead to improved local tolerability or systemic tolerability, as measured by various biomarkers. This improvement is particularly observed when administration is via the IM route. Monoester cationic lipids of the present invention may provide reduced swelling and/or redness at the injection site. The LNP compositions of the present invention provide efficient intracellular delivery of the agents, e.g., polynucleotides, and are better tolerated by the recipient subject than compositions formulated with different cationic lipid classes, including non-monoester cationic lipids and even other monoester cationic lipids. The monoester cationic lipids of this invention are further suitable for delivery of mRNA and non-mRNA actives, including but not limited to dsRNA, siRNA, etc.

It was surprisingly found herein that specific monoester cationic lipids, when formulated as part of lipid nanoparticles, provided effective intracellular delivery of encapsulated agents. These formulations also provided improved delivery of mRNA payload (e.g., expression of a protein (e.g., an antigen) encoded by the mRNA and improved local tolerability at site of administration of the LNP composition (e.g., when administered via IM route). In addition, it was surprisingly found that specific monoester cationic lipids, when formulated as part of an LNP composition of the invention, provided robust intracellular delivery of a nucleotide cargo and improved tolerability when compared to LNPs that did not include the specific monoester cationic lipids, such as MC3, MC3 ester derivatives, and Langer lipids. (See e.g., Maier M A, Jayaraman M, Matsuda S, et al. Biodegradable lipids enabling rapidly eliminated lipid nanoparticles for systemic delivery of RNAi therapeutics. Mol Ther. 2013; 21(8):1570-1578; Hassett et al., Optimization of Lipid Nanoparticles for Intramuscular Administration of mRNA Vaccines, Molecular Therapy Volume 15, P1-11, Apr. 15, 2019).

It was surprisingly found that certain monoester cationic lipids, when formulated as part of LNP, result in improved LNP performance with respect to the delivery of the encapsulated payload (e.g., expression of an mRNA payload) and/or tolerability at site of administration. In addition, it was surprisingly found that specific monoester cationic lipids, formulated as part of an LNP system, provided robust intracellular delivery of a nucleotide cargo and improved tolerability at site of administration relative to other known lipids, including other monoester cationic lipids. Finally, administration of LNPs for delivery of mRNA that contain specific monoester cationic lipids provide improved expression of antigen or protein and improved tolerability at site of administration.

The LNPs

Lipid nanoparticles (LNPs) of the present invention are used herein to deliver the encapsulated agent(s) for the treatment or prevention of disease. Generally, LNPs of the present invention include one or more cationic lipids, one or more poly(ethylneglycol)-lipid (PEG-lipid), one or more cholesterol, and one or more phospholipid.

In some embodiments, the LNP includes any cationic lipid mentioned in U.S. Patent Application Publication Nos. US 2008/0085870, US 2008/0057080, US 2009/0263407, US 2009/0285881, US 2010/0055168, US 2010/0055169, US 2010/0063135, US 2010/0076055, US 2010/0099738, US 2010/0104629, US 2013/0017239, or US 2016/0361411, International Patent Application Publication Nos. WO2011/022460; WO2012/040184, WO2011/076807, WO2010/021865, WO 2009/132131, WO2010/042877, WO2010/146740, or WO2010/105209, and in U.S. Pat. Nos. 5,208,036, 5,264,618, 5,279,833, 5,283,185, 6,890,557, or 9,669,097.

In some embodiments, the LNP includes a cationic lipid that carries a net positive charge at a selected pH, such as physiological pH. In some embodiments, the LNP includes a cationic lipid. In some embodiments, the LNP includes a cationic lipid selected from: N,N-dioleyl-N,N-dimethylammonium chloride ("DODAC"); N-[1-(2,3-dioleyloxy)propyl]-N,N,N-trimethylammonium chloride ("DOTMA"); N,N-distearyl-N,N-dimethylammonium bromide ("DDAB"); N-(2,3dioleoyloxy)propyl)-N,N,N-trimethylammonium chloride; 1 2-Dioleoyloxy-3-dimethylaminopropane ("DODAP"); 3-(N—(N,N-dimethylaminoethane)-carbam-oyl)cholesterol ("DC-Chol") and N-(1,2-dimyristyloxyprop-3-yl)-N,N-dimethyl-N-hydroxy ethyl ammonium bromide ("DMRIE"). In some embodiments, the LNP includes a cationic lipid selected from: LIPOFECTIN© (commercially available cationic lipid nanoparticles comprising DOTMA and 1,2-dioleoyl-sn-3-phosphoethanolamine ("DOPE"), from Gibco BRL, Grand Island, N.Y., USA); LIPOFECTAMINE© (commercially available cationic lipid nanoparticles comprising N-(1-(2,3dioleyloxy) propyl)N-(2-(sperminecarboxamido)ethyl)-N,N-dimethylaammonium trifluoroacetate; (2,3-dioleoyloxy-N-[2-(spermine-carboxamido)ethyl]-N,N-dimethyl-1-propanaminium) ("DOSPA") and 1,2-dioleoyl-sn-glycero-3-phosphoethanolamine ("DOPE"), from (Gibco BRL); and TRANSFECTAM© (commercially available cationic lipids comprising dioctadecyl amido glycyl carboxyspermine ("DOGS") in ethanol from Promega Corp., Madison, WI., USA). In some embodiments, the LNP includes a cationic lipid selected from: DODAP, DODMA, DMDMA, 1,2-DiLinoleyloxy-N,N-dimethylaminopropane (DLinDMA), 4-(2,2-diocta-9,12-dienyl-[1,3]dioxolan-4-ylmethyl)-dimethylamine, DLinKDMA (WO 2009/132131), DLin-K-C2-DMA (WO2010/042877), DLin-M-C3-DMA (WO2010/

146740 and/or WO2010/105209), 2-{4-[(33)-cholest-5-en-3-yloxy]butoxy}-N,N-dimethyl-3-[(9Z,12Z)-oct-adeca-9,12-dienlyloxyl]propan-1-amine) (CLinDMA), and the like.

In some embodiments of the invention, the cationic lipid component of the LNP is synthesized via various intermediates. In some embodiments, the intermediate is (11Z,14Z)-icosa-11,14-dienal; (2E,13Z,16Z)-ethyl docosa-2,13,16-trienoate; (Z)-undec-2-en-1-ol; (Z)-non-2-en-1-ol; (Z)-tridec-2-en-1-ol; (Z)-oct-2-en-1-ol; (Z)-hept-2-en-1-ol; or 1-methoxy-4-((oct-7-yn-1-yloxy)methyl)benzene. In some embodiments, the intermediate is (11Z, 14Z)-icosa-11,14-dienal. In some embodiments, the intermediate is (2E,13Z,16Z)-ethyl docosa-2,13,16-trienoate. In some embodiments, the intermediate is (Z)-undec-2-en-1-ol. In some embodiments, the intermediate is (Z)-non-2-en-1-ol. In some embodiments, the intermediate is (Z)-tridec-2-en-1-ol. In some embodiments, the intermediate is (Z)-oct-2-en-1-ol. In some embodiments, the intermediate is ((Z)-hept-2-en-1-ol. In some embodiments, the intermediate is 1-methoxy-4-((oct-7-yn-1-yloxy)methyl)benzene.

In some embodiments of the LNP of the invention, the cationic lipid is represented by the structure set forth in Formula A:

Formula A

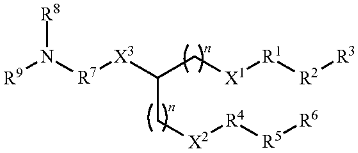

wherein, $X^2$ is

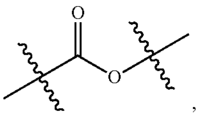,
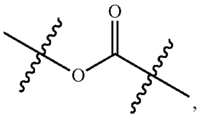, or absent;

$X^3$ is

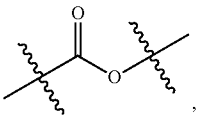,
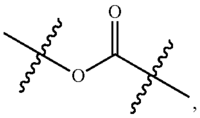, or absent;

$R^3$ is $C_1$-$C_{12}$ alkyl, $X^1$—$R^1$—$R^2$, $R^1$—$X^1$—$R^2$ or absent;

$R^4$ is $C_1$-$C_{12}$ alkyl, $C_1$-$C_{12}$ heteroalkyl, or absent;

$R^5$ is $C_1$-$C_{12}$ alkyl, or absent;

$R^6$ is $C_1$-$C_{12}$ alkyl or absent;

$R^7$ is $C_1$-$C_{12}$ alkyl, $C_1$-$C_{12}$ heteroalkyl, or absent;

$R^8$ is $C_1$-$C_{12}$ alkyl, $C_1$-$C_{12}$ heteroalkyl;

$R^9$ is $C_1$-$C_{12}$ alkyl, $C_1$-$C_{12}$ heteroalkyl;

optionally, $R^8$ and $R^9$, together with the nitrogen atom to which they are attached, can join to form a 4- to 8-membered monocyclic heterocycloalkyl group;

each $X^1$ is independently

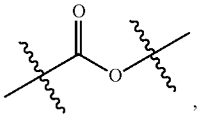,
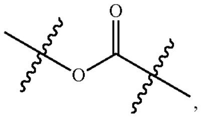, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and each n is independently 0-12.

In some embodiments of the LNP of the invention, the cationic lipid is represented by the structure set forth in Formula A, wherein $X^2$ is

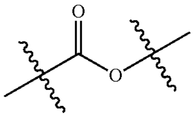 [SMILES: *OC(*)=O]

or absent;

$X^3$ is

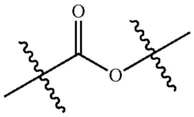 [SMILES: *OC(*)=O]

or absent;

$R^3$ is $C_4$-$C_{10}$ alkyl, $R^1$—$X^1$—$R^2$ or absent;

$R^4$ is $C_5$-$C_8$ alkyl or absent;

$R^5$ and $R^6$ are absent;

$R^7$ is $C_2$ alkyl;

$R^8$ is $C_1$ alkyl;

$R^9$ is $C_1$ alkyl;

each $X^1$ is independently

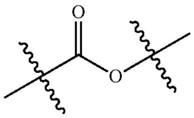 [SMILES: *OC(*)=O]

or cis-alkenyl;

each $R^1$ is independently $C_1$-$C_5$ alkyl or absent;

each $R^2$ is independently $C_1$ alkyl, cis-alkenyl, or absent; and each n is independently 1, 2, 4, 5, 6, 8, 9, or 10.

In some embodiments of the invention, the cationic lipid is represented by the structure set forth in Formula B:

Formula B

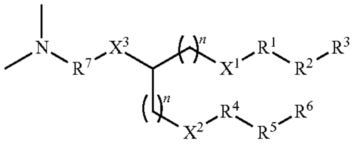

wherein, $X^2$ is

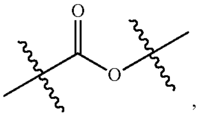,
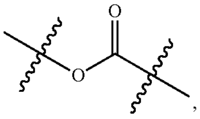, or absent, $X^3$ is

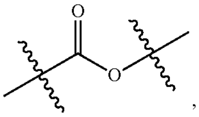,
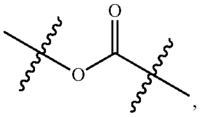, or absent;

$R^3$ is $C_1$-$C_{12}$ alkyl, $X^1$—$R^1$—$R^2$, $R^1$—$X^1$—$R^2$ or absent;

$R^4$ is $C_1$-$C_{12}$ alkyl, $C_1$-$C_{12}$ heteroalkyl, or absent;

$R^5$ is $C_1$-$C_{12}$ alkyl or absent;

$R^6$ is $C_1$-$C_{12}$ alkyl or absent;

$R^7$ is $C_1$-$C_{12}$ alkyl, $C_1$-$C_{12}$ heteroalkyl, or absent;

each $X^1$ is independently

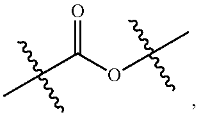,
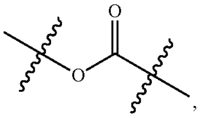, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and each n is independently 0-12.

In some embodiments of the invention, the cationic lipid is represented by the structure set forth in Formula B, wherein $X^2$ is

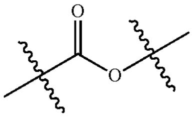 [SMILES: *OC(*)=O]

or absent, $X^3$ is

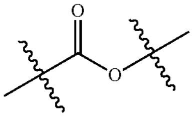 [SMILES: *OC(*)=O]

or absent;

$R^3$ is $C_4$-$C_{10}$ alkyl, $R^1$—$X^1$—$R^2$ or absent;

$R^4$ is $C_5$-$C_8$ alkyl or absent;

$R^5$ and $R^6$ are absent;

$R^7$ is $C_2$ alkyl;

each $X^1$ is independently

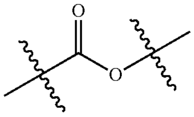

or cis-alkenyl;

each $R^1$ is independently $C_1$-$C_5$ alkyl or absent;

each $R^2$ is independently $C_1$ alkyl, cis-alkenyl, or absent; and each n is independently 1, 2, 4, 5, 6, 8, 9, or 10.

In some embodiments of the invention, the cationic lipid is represented by the structure set forth in Formula C:

Formula C

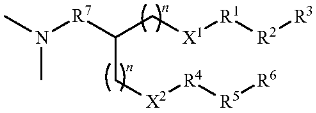

wherein, $X^2$ is

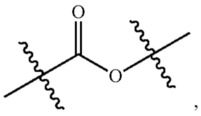,
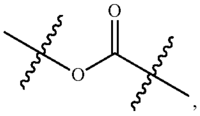, or absent;

$R^3$ is $C_1$-$C_{12}$ alkyl, $X^1$—$R^1$—$R^2$, $R^1$—$X^1$—$R^2$ or absent;

$R^4$ is $C_1$-$C_{12}$ alkyl, $C_1$-$C_{12}$ heteroalkyl, or absent;

$R^5$ is $C_1$-$C_{12}$ alkyl, or absent;

$R^6$ is $C_1$-$C_{12}$ alkyl or absent;

$R^7$ is $C_1$-$C_{12}$ alkyl, $C_1$-$C_{12}$ heteroalkyl, or absent;

each $X^1$ is independently

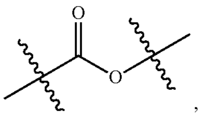,
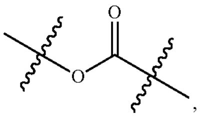, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and each n is independently 0-12.

In some embodiments of the invention, the cationic lipid is represented by the structure set forth in Formula C, wherein $X^2$ is

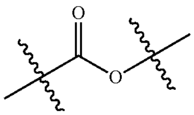 [SMILES: *OC(*)=O]

or absent;

$R^3$ is $C_4$-$C_{10}$ alkyl, $R^1$—$X^1$—$R^2$ or absent;

$R^4$ is $C_5$-$C_8$ alkyl or absent;

$R^5$ and $R^6$ are absent;

$R^7$ is $C_2$ alkyl;

each $X^1$ is independently

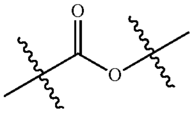 [SMILES: *OC(*)=O]

or cis-alkenyl;

each $R^1$ is independently $C_1$-$C_5$ alkyl or absent;

each $R^2$ is independently $C_1$ alkyl, cis-alkenyl, or absent; and each n is independently 1, 2, 4, 5, 6, 8, 9, or 10.

In some embodiments of the invention, the cationic lipid is represented by the structure set forth in Formula D.

Formula D

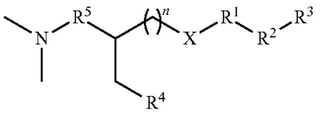

wherein, $R^3$ is $C_1$-$C_{12}$ alkyl, X—$R^1$—$R^2$, $R^1$—X—$R^2$ or absent;

$R^4$ is $C_1$-$C_{12}$ alkyl, $C_1$-$C_{12}$ heteroalkyl, or absent;

$R^5$ is $C_1$-$C_{12}$ alkyl;

each X is independently

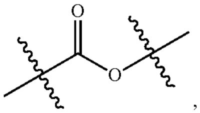
,
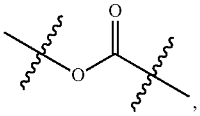
, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and each n is independently 0-12.

In some embodiments of the invention, the cationic lipid is represented by the structure set forth in Formula D, wherein each X is independently

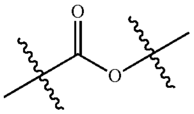 [SMILES: *OC(*)=O]

or cis-alkenyl;

each $R^1$ is independently $C_1$-$C_5$ alkyl or absent;

each $R^2$ is independently $C_1$ alkyl, cis-alkenyl, or absent;

$R^3$ is $C_4$-$C_{10}$ alkyl, $R^1$—X—$R^2$ or absent;

$R^4$ is $C_5$-$C_8$ alkyl or absent;

$R^5$ is $C_2$ alkyl; and each n is independently 4, 6, 8, 9, or 10.

In some embodiments of the invention, the cationic lipid is represented by the structure set forth in Formula E:

Formula E

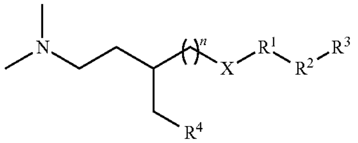

wherein, $R^3$ is $C_1$-$C_{12}$ alkyl, X—$R^1$—$R^2$, $R^1$—X—$R^2$, or absent;

$R^4$ is $C_1$-$C_{12}$ alkyl, $C_1$-$C_{12}$ heteroalkyl, or absent;

each X is independently

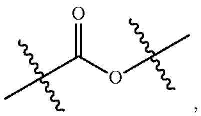
,
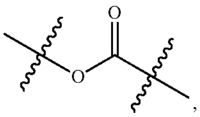
, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and each n is independently 0-12.

In some embodiments of the invention, the cationic lipid is represented by the structure set forth in Formula E, wherein $R^3$ is $C_4$-$C_{10}$ alkyl, $R^1$—X—$R^2$ or absent, $R^4$ is $C_5$-$C_8$ alkyl or absent;

each X is independently

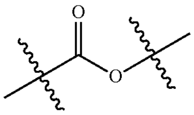 [SMILES: *OC(*)=O]

or cis-alkenyl;

each $R^1$ is independently $C_1$-$C_5$ alkyl or absent;

each $R^2$ is independently $C_1$ alkyl, cis-alkenyl, or absent; and each n is independently 4, 6, 8, 9, or 10.

In some embodiments of the invention, the cationic lipid is represented by the structure set forth in Formula F:

Formula F

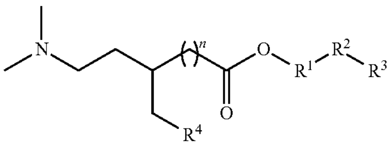

wherein, $R^1$ is $C_1$-$C_{12}$ alkyl;

$R^2$ is cis-alkenyl;

$R^3$ is $C_1$-$C_{12}$ alkyl;

$R^4$ is $C_1$-$C_{12}$ alkyl; and n is 0-12.

In some embodiments of the invention, the cationic lipid is represented by the structure set forth in Formula F, wherein $R^1$ is $C_1$;

$R^2$ is cis-alkenyl;

$R^3$ is $C_4$-$C_{10}$ alkyl;

$R^4$ is $C_5$-$C_8$ alkyl or absent; and each n is independently 4, 6, 8, 9, or 10.

In some embodiments, exemplary monoester cationic lipids include compounds 1-8 shown in Table I below:

In some embodiments of the invention, the cationic lipid is (20Z,23Z)-nonacosa-20,23-dien-10-yl 3-(dimethylamino)-propanoate. In some embodiments, the cationic lipid is (Z)-undec-2-en-1-yl 8-(2-(dimethylamino)ethyl)heptadecanoate. In some embodiments, the cationic lipid is (Z)-non-2-en-1-yl 10-(2-(dimethylamino)ethyl)nonadecanoate. In some embodiments, the cationic lipid is (Z)-tridec-2-en-1-yl 6-(2-(dimethylamino)ethyl)pentadecanoate. In some embodiments, the cationic lipid is pentyl (14Z,17Z)-4-(2-(dimethylamino)ethyl)tricosa-14,17-dienoate. In some

TABLE I

| Lipid | Structure | Chemical name |
|---|---|---|
| 1 | 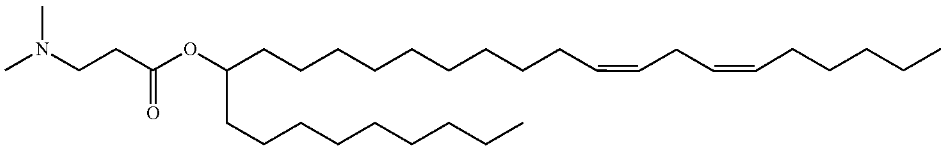 [SMILES: CCCCC/C=C\C/C=C\CCCCCCCCCC(CCCCCCCCC)OC(=O)CCN(C)C] | (20Z,23Z)-nonacosa-20,23-dien-10-yl 3-(dimethylamino)-propanoate |
| 2 | 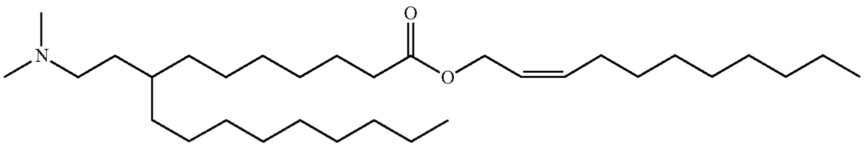 [SMILES: CCCCCCCC/C=C\COC(=O)CCCCCCC(CCCCCCCCC)CCN(C)C] | (Z)-undec-2-en-1-yl 8-(2-(dimethylamino) ethyl) heptadecanoate |
| 3 | 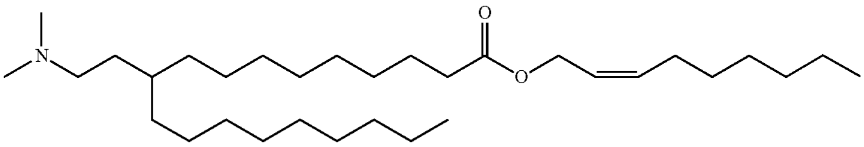 [SMILES: CCCCCC/C=C\COC(=O)CCCCCCCCC(CCCCCCCCC)CCN(C)C] | (Z)-non-2-en-1-yl 10-(2-(dimethylamino) ethyl) nonadecanoate |
| 4 | 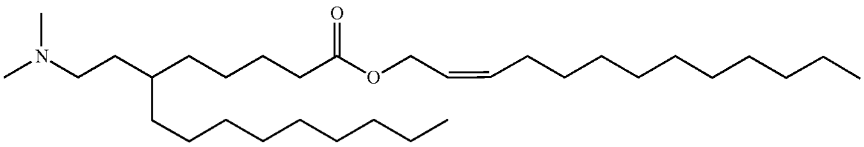 [SMILES: CCCCCCCCCC/C=C\COC(=O)CCCCC(CCCCCCCCC)CCN(C)C] | (Z)-tridec-2-en-1-yl 6-(2-(dimethylamino) ethyl) pentadecanoate |
| 5 | 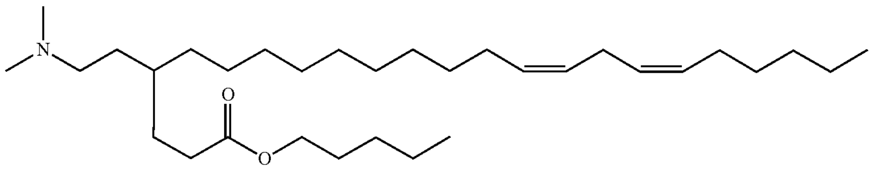 [SMILES: CCCCC/C=C\C/C=C\CCCCCCCCCC(CCC(=O)OCCCCC)CCN(C)C] | pentyl (14Z, 17Z)-4-(2-(dimethylamino) ethyl) tricosa-14,17-dienoate |
| 6 | 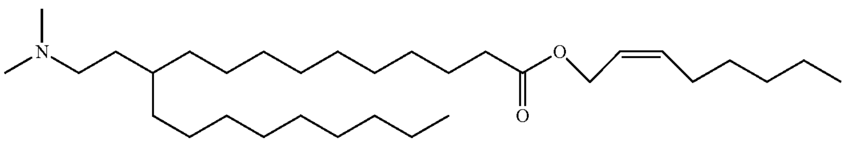 [SMILES: CCCCC/C=C\COC(=O)CCCCCCCCCC(CCCCCCCCC)CCN(C)C] | (Z)-oct-2-en-1-yl 11-(2-(dimethylamino) ethyl) icosanoate |
| 7 | 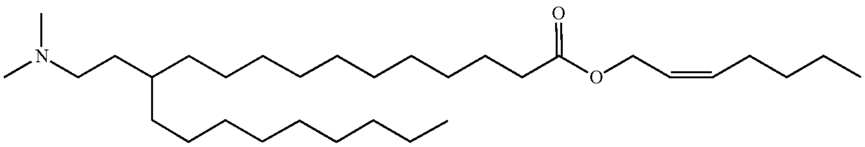 [SMILES: CCCC/C=C\COC(=O)CCCCCCCCCCC(CCCCCCCCC)CCN(C)C] | (Z)-hept-2-en-1-yl 12-(2-(dimethylamino)ethyl) henicosanoate |
| 8 | 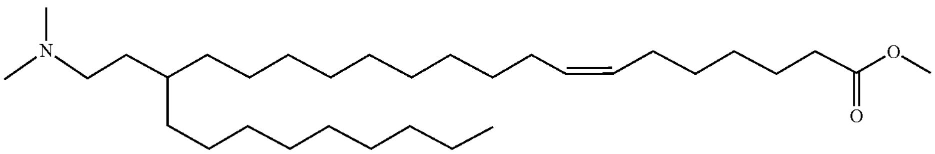 | methyl (Z)-18-(2-(dimethylamino)-ethyl)heptacos-7-enoate |

embodiments, the cationic lipid is (Z)-oct-2-en-1-yl 10-(2-(dimethylamino)ethyl)icosanoate. In some embodiments, the cationic lipid is (Z)-hept-2-en-1-yl 12-(2-(dimethylamino)ethyl)henicosanoate. In some embodiments, the cationic lipid is methyl (Z)-18-(2-(dimethylamino)-ethyl)heptacos-7-enoate.

In some embodiments, the LNP includes 30-65 mole % cationic lipid. In some embodiments, the LNP includes 30-55 mole % cationic lipid. In some embodiments, the LNP includes 30-45 mole % cationic lipid. In some embodiments, the LNP includes 55-65 mole % cationic lipid.

In some embodiments, the LNP includes a neutral lipid selected from: phospholipids, diaeylphosphatidylcholine, diacylphosphatidyletbanolamine, ceramide, sphingomyelin, cephalin, cholesterol, cerebrosides, diacylglycerols, and combinations thereof. In some embodiments, the neutral lipid includes a phospholipid and cholesterol.

In some embodiments, the neutral lipid includes a sterol, such as cholesterol. In some embodiments, the neutral lipid includes cholesterol. In some embodiments, the LNP includes 10-40 mole % cholesterol. In some embodiments, the LNP includes 15-25 mole % cholesterol. In some embodiments, the LNP includes 10-20 mole % cholesterol. In some embodiments, the LNP includes 20-30 mole % cholesterol. In some embodiments, the LNP includes 10-15 mole % cholesterol. In some embodiments, the LNP includes 25-35 mole % cholesterol.

In some embodiments, the LNP includes a phospholipid selected from: phospholipids, aminolipids and sphingolipids. In some embodiments, the LNP includes a phospholipid selected from: phosphatidylcholine, phosphatidylethanolamine, phosphatidylserine, phosphatidylinositol, phosphatidic acid, palmitoyloleryl phosphatidylcholine, lysophosphatidylcholine, lysophosphatidylethanolamine, dipalmitoylphosphatidylcholine, dioleoylphospbatidylcholine, dstearoylphosphatidylcholine and dilinoleoylphosphatidylcholine. In some embodiments, the LNP includes a neutral lipid selected from: sphingolipid, glycosphingolipid families, diacylglycerols and S-acyloxyacids. In some embodiments, the LNP includes a neutral lipid selected from: phosphatidylcholine (PC), phosphatidylethanolamine (PE), and phosphatidylglycerol (PG), phosphatidylserine (PS), phosphatidylinositol (PI), phosphatidic acid (phosphatidate) (PA), dipalmitoylphosphatidylcholine, monoacylphosphatidylcholine (lyso PC), 1-palmitoyl-2-oleoyl-sn-glycero-3-phosphocholine (POPC), N-acyl-PE, phosphoinositides, and phosphosphingolipids. In some embodiments, the LNP includes a neutral lipid selected from: phosphatidic acid (DMPA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), and phosphatidylserine (DOPS). In some embodiments, the LNP includes a neutral lipid selected from: fatty acids include C14:0, palmitic acid (C16:0), stearic acid (C18:0), oleic acid (C18:1), linoleic acid (C18:2), linolenic acid (C18:3), arachidonic acid (C20:4), C20:0, C22:0 and lecithin. In some embodiments, the phospholipid includes 1,2-Distearoyl-sn-glycero-3-phosphocholine (DSPC).

In some embodiments, the neutral lipid includes a phospholipid. In some embodiments, the LNP includes 5-30 mole % phospholipid. In some embodiments, the LNP includes 5-15 mole % phospholipid. In some embodiments, the LNP includes 10-20 mole % phospholipid. In some embodiments, the LNP includes 20-30 mole % phospholipid. In some embodiments, the LNP includes 10-15 mole % phospholipid. In some embodiments, the LNP includes 25-30 mole % phospholipid.

In some embodiments, the polymer-lipid conjugate includes a PEG-lipid. In some embodiments, the LNP includes a PEG-lipid selected from: α-[8'-(1,2-Dimyristoyl-3-propanoxy)-carboxamide-3', 6'-Dioxaoctanyl]carbamoyl-ω-methyl-poly(ethylene glycol); 1,2-didecanoyl-rac-glycero-3-methylpolyoxyethylene; 1,2-didodecanoyl-rac-glycero-3-methylpolyoxyethylene; and 1,2-Distearoyl-rac-glycero-3-methylpolyoxyethylene.

In some embodiments, the LNP includes 0.05-5 mole % polymer-lipid conjugate. In some embodiments, the LNP includes 1-4 mole % polymer-lipid conjugate. In some embodiments, the LNP includes 0.5-2 mole % polymer-lipid conjugate. In some embodiments, the LNP includes 1-4 mole % polymer-lipid conjugate. In some embodiments, the LNP includes 1-3 mole % polymer-lipid conjugate. In some embodiments, the LNP includes 1-2.5 mole % polymer-lipid conjugate.

In some embodiments, the LNP includes 30-65 mole % cationic lipid, 10-30 mole % cholesterol, 5-30 mole % phospholipid, and 0.05-4 mole % PEG-lipid. In some embodiments, the LNP includes 55-65 mole % cationic lipid, 25-35 mole % cholesterol, 5-15 mole % phospholipid, and 1-2.5 mole % PEG-lipid. In some embodiments, the LNP includes 40-50 mole % cationic lipid, 15-20 mole % cholesterol, 18-20 mole % phospholipid, and 1.5-2.5 mole % PEG-lipid. In some embodiments, the LNP includes 56-59 mole % cationic lipid, 15-20 mole % cholesterol, 18-20 mole % phospholipid, and 0.5-1.5 mole % PEG-lipid.

The Agents

In some embodiments, the LNPs of the present invention deliver encapsulated agents. Agents may include any particles, compounds, molecules, or entities of any chemical class including, for example, a small molecule, polypeptide (e.g., a protein), polynucleotide (e.g., a DNA polynucleotide or an RNA polynucleotide), saccharide, lipid, or a combination or complex thereof.

In some embodiments, the agent is a nucleic acid or polynucleotide. The agent may include polynucleotides, such as mRNA, self-amplifying mRNA, siRNA, miRNA, DNA, cDNA. In some embodiments, the polynucleotide may be a DNA polynucleotide or an RNA polynucleotide. In some embodiments, the polynucleotide may include DNA polynucleotides such as antisense DNA, plasmid DNA, pre-condensed DNA, DNA produced by a polymerase chain reaction (PCR), vector DNA (P1, PAC, BAC, YAC, artificial chromosomes), a DNA aptamer, an expression cassette, a chimeric sequence, chromosomal DNA, or a form derivative thereof. In some embodiments, the polynucleotide may include RNA polynucleotides such as tRNA (transfer RNA), snRNA (small nuclear RNA), rRNA (ribosomal RNA), mRNA (messenger RNA), antisense RNA, siRNA (small interfering RNA), miRNA, shRNA (short hairpin RNA), ncRNA (non-coding RNA), an RNA aptamer, a ribozyme, a chimeric sequence, or a form derivative thereof. In some embodiments, the polynucleotide can be single, double, triple, or quadruple stranded in its entirety or in any portion thereof. In some embodiments, the polynucleotide may include a phosphodiester backbone. In some embodiments, the polynucleotide may include a peptide bond backbone. In some embodiments, the polynucleotide may include one or more phosphorothioate linkages and/or 5'-N-phosphoramidite linkages, e.g., rather a phosphodiester bond. In some embodiments, the polynucleotide may have a nucleotide sequence that encodes a functional gene product such as an RNA or protein. In some embodiments, the polynucleotide may include one or more introns. In some embodiments, the polynucleotide may be prepared by one or more of isolation from a natural source, enzymatic synthesis by polymerization based on a complementary template (in vivo or in vitro), reproduction in a recombinant cell or system, and chemical synthesis. In some embodiments, a polynucleotide is at least 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more nucleic acid residues long. In some embodiments a polynucleotide may have a nucleotide sequence including at least one element that encodes, or is the complement of a sequence that encodes, all or a portion of a polypeptide. In some embodiments, a polynucleotide has enzymatic activity.

The LNP Compositions

In some embodiments of the invention, the LNP compositions are formed, for example, by a rapid precipitation process that entails micro-mixing the lipid components dissolved in a lower alkanol solution (e.g., ethanol) with an aqueous solution containing polynucleotide(s) using a confined volume mixing apparatus such as a confined volume T-mixer, a multi-inlet vortex mixer, microfluidics mixer devices, or other. The lipid solution may include one or more cationic lipids, one or more neutral lipid (e.g., phospholipids, DSPC, cholesterol), one or more polymer-lipid conjugate (e.g., PEG-DMG) at specific molar ratios in ethanol to form an organic solution. In some embodiments, the lipid/ethanol solution is then mixed with an aqueous solution of an agent, e.g., a polynucleotide or mRNA. The aqueous solution may be a buffer, selected from: a sodium citrate, a sodium acetate buffered salt solution, and combinations thereof, wherein the buffer may have a pH of about 2-6.

In some embodiments, the aqueous and organic solutions are optionally heated to a temperature in the range of 25° C.-45° C., preferably 30° C.-40° C., and then mixed in a confined volume mixer to form the LNP. When a confined volume T-mixer is used, the T-mixer may have an internal diameter range from 0.25 to 10.0 mm. In some embodiments, the alcohol and aqueous solutions may be delivered to the inlet of the T-mixer using programmable syringe pumps, and with a total flow rate from 10 mL/min-600 L/minute. In some embodiments, the aqueous and alcohol solutions may be combined in the confined-volume mixer with a ratio in the range of 1:1 to 4:1 vol:vol. In some embodiments, the aqueous and alcohol solutions may be combined at a ratio in the range of 1.1:1 to 4:1, 1.2:1 to 4:1, 1.25:1 to 4:1, 1.3:1 to 4:1, 1.5:1 to 4:1, 1.6:1 to 4:1, 1.7:1 to 4:1, 1.8:1 to 4:1, 1.9:1 to 4:1, 2.0:1 to 4:1, 2.5:1 to 4:1, 3.0:1 to 4:1, and 3.5:1 to 4:1.

In some embodiments, the organic and aqueous solutions may be delivered to the inlet of the T-mixer using programmable syringe pumps and with a total flow rate from 10 mL/min-600 L/minute and combined with a ratio in the range of about 1:1 to 4:1 vol:vol. In some embodiments, the mixing of the lipid/ethanal and mRNA/aqueous solutions forms the LNP composition. The resulting LNP suspension may be then twice diluted with a buffer, such as a citrate buffered solution having a pH of about 6-8, in a sequential, in-line mixing process. For the first dilution, the LNP suspension may be mixed with a buffered solution having a pH of about 6-7.5 and a mixing ratio in the range of about 1:1 to 1:3 vol:vol. The resulting LNP suspension may then be further mixed with a buffered solution having a pH of about 6-8 and a mixing ratio in the range of 1:1 to 1:3 vol:vol.

In some embodiments, the LNP compositions may then be concentrated and filtered via an ultrafiltration process where the alcohol is removed and the buffer exchanged for the final buffer solution. The ultrafiltration process, having a tangential flow filtration format ("TFF"), used a hollow fiber membrane nominal molecular weight cutoff range from 30-500 KD, targeting 100 KD. The TFF may retain the LNP composition in the retentate and the filtrate or permeate may contain the alcohol and final buffer wastes. The TFF may provide an initial concentration to a lipid concentration of 20-100 mg/mL. Following concentration, the LNP suspension may be diafiltered against the final buffer with pH 7-8, 10 mM Tris, 140 mM NaCl with pH 7-8, or 10 mM Tris, 70 mM NaCl, 5-10 wt % sucrose, with pH 7-8, for 5-20 volumes to remove the alcohol and perform buffer exchange. The material may then be concentrated via ultrafiltration.

In some embodiments, the concentrated LNP suspension is then sterile filtered into a suitable container under aseptic conditions. Sterile filtration was accomplished by passing the LNP suspension through a pre-filter (Acropak 500 PES 0.45/0.8μιη capsule) and a bioburden reduction filter (Acropak 500 PES 0.2/0.8μιη capsule). Following filtration, the vialed LNP product may be stored 0° C. to −20° C.

In some embodiments, the combination of ethanol volume fraction, solution flow rates, lipid(s) concentrations, polynucleotide (s) concentrations, mixer configuration and internal diameter, and mixer tubing internal diameter utilized at this mixing stage may provide LNPs having a particle size of the between 30 and 300 nm and the encapsulation efficiency of the agent, e.g., polynucleotide or mRNA, in the amount of about 70-100%. The encapsulation efficiency of the polynucleotide may be defined as the fraction of the agent, e.g., polynucleotide or mRNA, found inside the LNP, i.e., encapsulated, versus outside of the LNP. In some embodiments, the encapsulation efficiency of encapsulated polynucleotide in compositions of the present invention may be greater than 80%. In some embodiments, the encapsulation efficiency of encapsulated polynucleotides in compositions of the present invention is about 80-100%. The resulting LNP suspension may be twice diluted into higher pH buffers in the range of 6-8 to form the composition.

In some embodiments, the dilution step may be performed at a temperature in the range of 15-40° C. In some embodiments, the dilution step may be performed at a temperature in the range of 30-40° C. In some embodiments, the resulting LNP suspension may be further mixed with a high pH buffer, i.e., a buffered solution at a higher pH, (e.g., 6-8) and with a mixing ratio in the range of 1:1 to 1:3 vol:vol to form the composition.

In some embodiments, the LNP suspension may be subjected to an incubation period where the suspension may be held from a minimum of 1 second to 48 hours prior to an anion exchange filtration step. In some embodiments, the temperature during this incubation period may be in the range of 15-40° C. In some embodiments, the LNP suspension may be filtered after the incubation step. In some embodiments, the LNP suspension may be filtered through a filter containing an anion exchange separation step, such as an 0.8 micron filter.

In some embodiments, the LNP compositions may also be concentrated and filtered via an ultrafiltration process to remove the alcohol. In some embodiments, the high pH buffer may also be removed and exchanged for a final buffer solution. In some embodiments, the final buffer solution may be selected from a phosphate buffered saline or any buffer system suitable for cryopreservation (for example, buffers containing sucrose, trehalose, or combinations thereof).

In some embodiments, the LNP composition may be subjected to an ultrafiltration process that uses a tangential flow filtration format ("TFF"). In some embodiments, the process may use a membrane nominal molecular weight cutoff range from 30-500 KD. In some embodiments, the filtration membrane may include a hollow fiber or a flat sheet cassette. In some embodiments, the TFF processes with the proper molecular weight cutoff may retain the LNP in the retentate and the filtrate or permeate that includes the alcohol and final buffer wastes. In some embodiments, the TFF process is a multiple step process with an initial concentration to a lipid concentration of 20-100 mg/mL. Following concentration, the LNP suspension may be diafiltered against the final buffer for 5-20 volumes to remove the alcohol and perform the buffer exchange. In some embodiments, the suspension may also be concentrated an additional 1-3 fold via ultrafiltration. In some embodiments, the LNP composition manufacturing process may also include a sterilization step where the concentrated LNP suspension is sterile filtered into a suitable container under aseptic conditions. In some embodiments, the sterile filtration may be accomplished by any system contemplated in the art, such as, e.g., passing the LNP suspension through a pre-filter (such as, e.g., Acropak 500 PES 0.45/0.8μιη capsule) or a bioburden reduction filter (such as, e.g., Acropak 500 PES 0.2/0.8μιη capsule). Following filtration, the vialed LNP product may be stored under suitable storage conditions (such as, 2° C.-8° C., or −80 to −20° C. if frozen) or may be lyophilized.

Tolerability of the LNP Composition

In some embodiments, tolerability may refer to local tolerability, e.g., at the site of administration, or systemic tolerability, e.g., throughout the entire body, or a combination thereof. In some embodiments, tolerability may be assessed as determined by the presence of a biomarker, which may be analyzed via a sample of tissue or blood taken from the subject. In some embodiments, a biomarker may be the number of neutrophils and/or white blood cells of the subject after administration of LNPs. In some embodiments, a biomarker of increased tolerability in a subject administered LNPs that include a monoester cationic lipid may be a lower level of neutrophils and/or white blood cells than the levels of neutrophils and/or white blood cells in a subject administered LNPs that do not include monoester cationic lipids. In some embodiments, a biomarker may include an observed change in body temperature of the subject after administration of LNPs. In some embodiments, subjects administered LNPs that include monoester cationic lipids may exhibit a lower increase in body temperature than subjects administered LNPs that did not include monoester cationic lipids. In some embodiments, subjects administered LNPs that include monoester cationic lipids may exhibit an initial increase in body temperature that returns to a normal temperature (e.g., approximately 98.6° F.) faster than subjects administered LNPs that did not include monoester cationic lipids. In some embodiments, the biomarker may indicate a level of inflammatory response in the body of the subject, as a whole, after administration of the LNPs. In some embodiments, subjects administered LNPs that include monoester cationic lipids may exhibit a lower inflammatory response than subjects administered LNPs that did not include monoester cationic lipids.

In some embodiments, the tolerability of the LNP composition at the site of administration may be evaluated by determining the terminal half-life (t½) of the elimination of the cationic lipids. Specifically, the terminal half-life of the present invention may refer to the time it takes for the concentration of a the LNP comprising an agent, such as a polynucleotide or mRNA, to reduce to its original value by half. Systemic half-life refers to the time it takes for plasma concentration of the active pharmaceutical ingredient to reduce to half its original value. Local half-life refers to the time it takes for local tissue concentration of the active pharmaceutical ingredient to reduce to half its original value.

In some embodiments, the terminal half-life may be determined by collecting samples of blood and tissues, including e.g., muscles, around the injection sites. The blood samples may be centrifuged to obtain plasma samples. The tissue samples may be homogenized in the presence homogenization buffer, such as a Tris buffer, sucrose, a non-selective protease inhibitor 4-(2-aminoethyl)benzenesulfonyl fluoride, or combinations thereof, and the like.

In some embodiments, the concentrations of cationic lipids in plasma and tissue samples may be determined by an LC-MS/MS assay following a protein precipitation step and addition of an appropriate internal standard (labetalol, imipramine, or diclofenac). Quantification may be performed by determining peak area-ratios of the cation lipids to the internal standard.

In some embodiments, pharmacokinetic parameters may be obtained using non-compartmental methods (e.g., Phoenix®). The area under the drug concentration-time curve (AUC0-t) may be calculated from the first time point (0 min) up to the last time point with measurable drug concentration using the linear trapezoidal or linear/log-linear trapezoidal rule. The terminal half-life of elimination (t½) may be determined by unweighted linear regression analysis of the log-transformed data. The time points for determination of half-life may be selected by visual inspection of the data.

In some embodiments, the terminal half-life of elimination (t½) of cationic lipids at the site of administration, when administered as a component of lipid nanoparticle formulations via the intramuscular route, may be decreased for ester-containing cationic lipids in comparison to cationic lipids that do not include an ester. In some embodiments, ester-containing cationic lipids (e.g., LNPs 3, 6, and 9-11 of the present invention) were more rapidly eliminated from the site of administration relative to non-ester containing cationic lipids (e.g., LNPs 12 and 13).

In some embodiments, the terminal half-life of elimination of the monoester cationic lipids when administered as a component of the LNP composition is less than 100 hours. In some embodiments, the terminal half-life of elimination of the cationic lipids when administered as a component of the LNP composition is less than 50 hours. In some embodiments, the terminal half-life of elimination of the cationic lipids when administered as a component of the LNP composition is less than 25 hours. In some embodiments, the terminal half-life of elimination of the cationic lipids when administered as a component of the LNP composition is less than 10 hours. In some embodiments, the terminal half-life of elimination of the cationic lipids when administered as a component of the LNP composition is less between 4 hours and 10 hours. In some embodiments, the terminal half-life of elimination of the cationic lipids when administered as a component of the LNP composition is less between 5 hours and 9 hours. In some embodiments, the terminal half-life of elimination of the cationic lipids when administered as a component of the LNP composition is less between 5 hours and 8 hours. In some embodiments, the terminal half-life of elimination of the cationic lipids when administered as a component of the LNP composition is less between 6 hours and 8 hours. In some embodiments, the terminal half-life of elimination of the cationic lipids when administered as a component of the LNP composition is less between 7 hours and 9 hours. In some embodiments, the terminal half-life of elimination of the cationic lipids when administered as a component of the LNP composition is 1 hour, 2 hours, 3 hours, 4 hours, 5 hours, six hours, seven hours, eight hours, nine hours, or 10 hours.

In some embodiments, the use of a monoester cationic lipid of the present invention when administered as a component of the LNP composition provides improved systemic tolerability when compared to LNP compositions that do not include the same monoester cationic lipid. In some embodiments, the systemic tolerability is measured by a biomarker. In some embodiments, the biomarker may indicate an attenuated inflammatory response to LNPs including monoester cationic lipids of the present invention. In some embodiments, LNP compositions that included monoesters of the present invention may provide biomarkers that were lower than LNP compositions that did not include monoesters of the present invention. In some embodiments, LNP compositions that included monoesters of the present invention may provide biomarkers that returned to a normal level quicker than LNP compositions that did not include monoesters of the present invention.

In some embodiments, LNP compositions that include a monoester cationic lipid having the structure set forth in Formula D:

Formula D

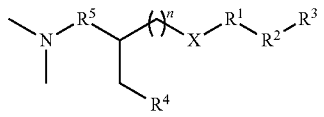

wherein, $R^3$ is $C_1$-$C_{12}$ alkyl, X—$R^1$—$R^2$, $R^1$—X—$R^2$ or absent;

$R^4$ is $C_1$-$C_{12}$ alkyl, $C_1$-$C_{12}$ heteroalkyl, or absent;

$R^5$ is $C_1$-$C_{12}$ alkyl;

each X is independently

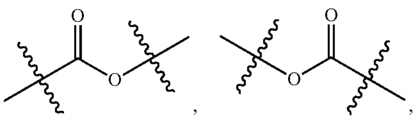 [SMILES: *OC(*)=O ; *OC(*)=O]

cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and each n is independently 0-12, provide improved systemic tolerability in comparison to LNP compositions that did not include the monoester cationic lipid having the structure set forth in Formula D. In some embodiments, the improved systemic tolerability includes an attenuated biomarker. In some embodiments, the improved systemic tolerability includes an attenuated inflammatory response. In some embodiments, improved systemic tolerability may include biomarkers that return to a normal level quicker than LNP compositions that do not include the monoester cationic lipid having the structure set forth in Formula D.

In some embodiments, LNP compositions that include a monoester cationic lipid selected from the group consisting of: (20Z,23Z)-nonacosa-20,23-dien-10-yl 3-(dimethylamino)-propanoate, (Z)-undec-2-en-1-yl 8-(2-(dimethylamino)ethyl)heptadecanoate, (Z)-non-2-en-1-yl 10-(2-(dimethylamino)ethyl)nonadecanoate, (Z)-tridec-2-en-1-yl 6-(2-(dimethylamino)ethyl)pentadecanoate, pentyl (14Z,17Z)-4-(2-(dimethylamino)ethyl)tricosa-14,17-dienoate, (Z)-oct-2-en-1-yl 11-(2-(dimethylamino)ethyl)icosanoate, (Z)-hept-2-en-1-yl 12-(2-(dimethylamino)ethyl)henicosanoate, methyl (Z)-18-(2-(dimethylamino)-ethyl)heptacos-7-enoate, and combinations thereof, provide improved systemic tolerability in comparison to LNP compositions that do not include the monoester cationic lipid. In some embodiments, the improved systemic tolerability includes an attenuated biomarker. In some embodiments, the improved systemic tolerability includes an attenuated inflammatory response. In some embodiments, improved systemic tolerability is measured by biomarkers that return to a normal level quicker than LNP compositions that did not include the monoester cationic lipid.

All publications mentioned herein are incorporated by reference for the purpose of describing and disclosing methodologies and materials that might be used in connection with the present invention. Nothing herein is to be construed as an admission that the invention is not entitled to antedate such disclosure by virtue of prior invention.

Having described preferred embodiments of the invention with reference to the accompanying drawings, it is to be understood that the invention is not limited to those precise embodiments, and that various changes and modifications may be used by one skilled in the art without departing from the scope or spirit of the invention as defined in the appended claims.

In embodiment 1, a composition is provided that includes a lipid nanoparticle (LNP) including:

a monoester cationic lipid having the structure set forth in Formula A:

Formula A

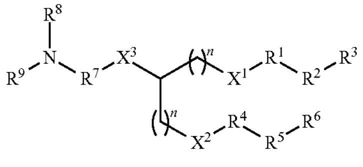

wherein, $X^2$ is

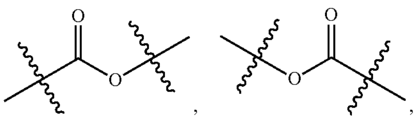 [SMILES: *OC(*)=O ; *OC(*)=O]

or absent;

$X^3$ is

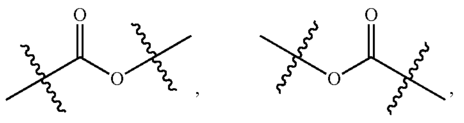 [SMILES: *OC(*)=O ; *OC(*)=O]

or absent;

$R^3$ is $C_1$-$C_{12}$ alkyl, $X^1$—$R^1$—$R^2$, $R^1$—$X^1$—$R^2$ or absent;

$R^4$ is $C_1$-$C_{12}$ alkyl, $C_1$-$C_{12}$ heteroalkyl, or absent;

$R^5$ is $C_1$-$C_{12}$ alkyl, or absent;

$R^6$ is $C_1$-$C_{12}$ alkyl or absent;

$R^7$ is $C_1$-$C_{12}$ alkyl, $C_1$-$C_{12}$ heteroalkyl, or absent;

$R^8$ is $C_1$-$C_{12}$ alkyl, $C_1$-$C_{12}$ heteroalkyl;

$R^9$ is $C_1$-$C_{12}$ alkyl, $C_1$-$C_{12}$ heteroalkyl;

optionally, $R^8$ and $R^9$, together with the nitrogen atom to which they are attached, can join to form a 4- to 8-membered monocyclic heterocycloalkyl group;

each $X^1$ is independently

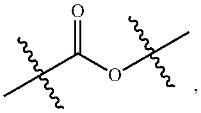
,
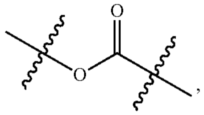
, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and each n is independently 0-12.

In embodiment 2, the composition of embodiment 1 is provided wherein $X^2$ is

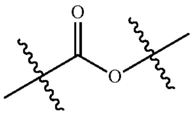

or absent;

$X^3$ is

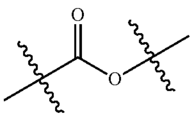 [SMILES: *OC(*)=O]

or absent;

$R^3$ is $C_4$-$C_{10}$ alkyl, $R^1$—$X^1$—$R^2$ or absent;

$R^4$ is $C_5$-$C_8$ alkyl or absent;

$R^5$ and $R^6$ are absent;

$R^7$ is $C_2$ alkyl;

$R^8$ is $C_1$ alkyl;

$R^9$ is $C_1$ alkyl;

each $X^1$ is independently

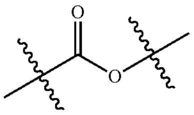 [SMILES: *OC(*)=O]

or cis-alkenyl;

each $R^1$ is independently $C_1$-$C_5$ alkyl or absent;

each $R^2$ is independently $C_1$ alkyl, cis-alkenyl, or absent; and each n is independently 1, 2, 4, 5, 6, 8, 9, or 10.

In embodiment 3, a composition is provided that includes a lipid nanoparticle (LNP) including:

a monoester cationic lipid having the structure set forth in Formula B:

Formula B

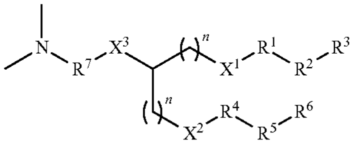

wherein, $X^2$ is

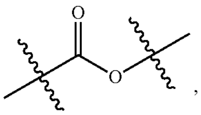
,
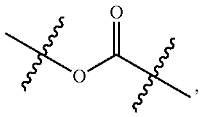
, or absent;

$X^3$ is

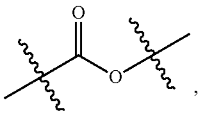
,
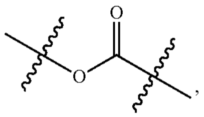
, or absent;

$R^3$ is $C_1$-$C_{12}$ alkyl, $X^1$—$R^1$—$R^2$, $R^1$—$X^1$—$R^2$ or absent;

$R^4$ is $C_1$-$C_{12}$ alkyl, $C_1$-$C_{12}$ heteroalkyl, or absent;

$R^5$ is $C_1$-$C_{12}$ alkyl, or absent;

$R^6$ is $C_1$-$C_{12}$ alkyl or absent;

$R^7$ is $C_1$-$C_{12}$ alkyl, $C_1$-$C_{12}$ heteroalkyl, or absent;

each $X^1$ is independently

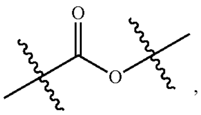
,
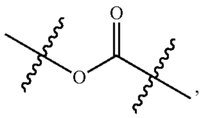
, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and each n is independently 0-12.

In embodiment 4, the composition of embodiment 3 is provided, wherein $X^2$ is

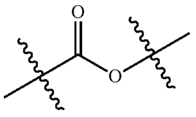 [SMILES: *OC(*)=O]

or absent;

$X^3$ is

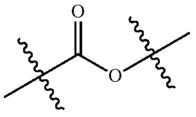 [SMILES: *OC(*)=O]

or absent;

$R^3$ is $C_4$-$C_{10}$ alkyl, $R^1$—$X^1$—$R^2$ or absent;

$R^4$ is $C_5$-$C_8$ alkyl or absent;

$R^5$ and $R^6$ are absent;

$R^7$ is $C_2$ alkyl;

each $X^1$ is independently

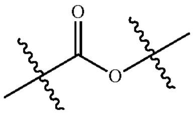 [SMILES: *OC(*)=O]

or cis-alkenyl;

each $R^1$ is independently $C_1$-$C_5$ alkyl or absent;

each $R^2$ is independently $C_1$ alkyl, cis-alkenyl, or absent; and each n is independently 1, 2, 4, 5, 6, 8, 9, or 10.

In embodiment 5, a composition is provided that includes a lipid nanoparticle (LNP) including:

a monoester cationic lipid having the structure set forth in Formula C:

Formula C

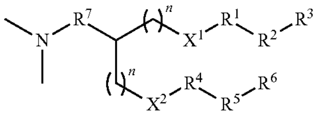

wherein, $X^2$ is

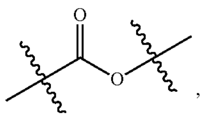
,
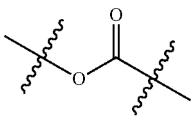
, or absent;

$R^3$ is $C_1$-$C_{12}$ alkyl, $X^1$—$R^1$—$R^2$, $R^1$—$X^1$—$R^2$ or absent;

$R^4$ is $C_1$-$C_{12}$ alkyl, $C_1$-$C_{12}$ heteroalkyl, or absent;

$R^5$ is $C_1$-$C_{12}$ alkyl, or absent;

$R^6$ is $C_1$-$C_{12}$ alkyl or absent;

$R^7$ is $C_1$-$C_{12}$ alkyl, $C_1$-$C_{12}$ heteroalkyl, or absent;

each $X^1$ is independently

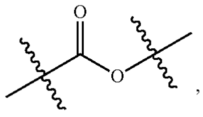
,
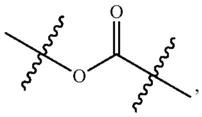
, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and each n is independently 0-12.

In embodiment 6, the composition of embodiment 5 is provided, wherein $X^2$ is

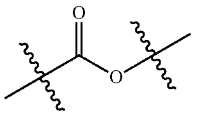 [SMILES: *OC(*)=O]

or absent;

$R^3$ is $C_4$-$C_{10}$ alkyl, $R^1$—$X^1$—$R^2$ or absent;

$R^4$ is $C_5$-$C_8$ alkyl or absent;

$R^5$ and $R^6$ are absent;

$R^7$ is $C_2$ alkyl;

each $X^1$ is independently

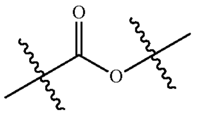 [SMILES: *OC(*)=O]

or cis-alkenyl;

each $R^1$ is independently $C_1$-$C_5$ alkyl or absent;

each $R^2$ is independently $C_1$ alkyl, cis-alkenyl, or absent; and each n is independently 1, 2, 4, 5, 6, 8, 9, or 10.

In embodiment 7, a composition is provided that includes a lipid nanoparticle (LNP) including:

a monoester cationic lipid having the structure set forth in Formula D:

Formula D

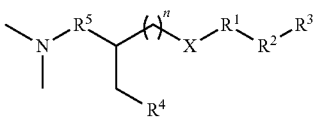

wherein, $R^3$ is $C_1$-$C_{12}$ alkyl, X—$R^1$—$R^2$, $R^1$—X—$R^2$ or absent;

$R^4$ is $C_1$-$C_{12}$ alkyl, $C_1$-$C_{12}$ heteroalkyl, or absent;

$R^5$ is $C_1$-$C_{12}$ alkyl;

each X is independently

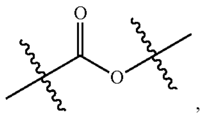,
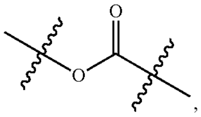, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and n is 0-12.

In embodiment 8, the composition of embodiment 7 is provided, wherein $R^3$ is $C_4$-$C_{10}$ alkyl, $R^1$—X—$R^2$ or absent;

$R^4$ is $C_5$-$C_8$ alkyl or absent;

$R^5$ is $C_2$ alkyl;

each X is independently

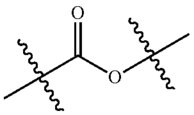 [SMILES: *OC(*)=O]

or cis-alkenyl;

each $R^1$ is independently $C_1$-$C_5$ alkyl or absent;

each $R^2$ is independently $C_1$ alkyl, cis-alkenyl, or absent; and n is 4, 6, 8, 9, or 10.

In embodiment 9, a composition is provided that includes a lipid nanoparticle (LNP) including:

a monoester cationic lipid having the structure set forth in Formula E:

Formula E

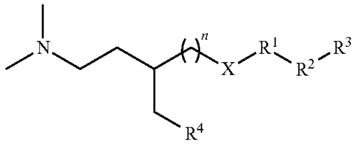

wherein, $R^3$ is $C_1$-$C_{12}$ alkyl, X—$R^1$—$R^2$, $R^1$—X—$R^2$, or absent;

$R^4$ is $C_1$-$C_{12}$ alkyl, $C_1$-$C_{12}$ heteroalkyl, or absent;

each X is independently

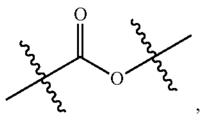,
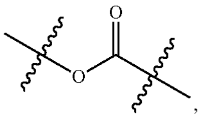, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and n is 0-12.

In embodiment 10, the composition of embodiment 9 is provided wherein $R^3$ is $C_4$-$C_{10}$ alkyl, $R^1$—X—$R^2$ or absent;

$R^4$ is $C_5$-$C_8$ alkyl or absent;

each X is independently

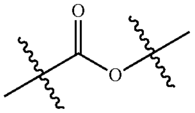 [SMILES: *OC(*)=O]

or cis-alkenyl;

each $R^1$ is independently $C_1$-$C_5$ alkyl or absent;

each $R^2$ is independently $C_1$ alkyl, cis-alkenyl, or absent; and n is 4, 6, 8, 9, or 10.

In embodiment 11, a composition is provided that includes a lipid nanoparticle (LNP) including:

a monoester cationic lipid having the structure set forth in Formula F:

Formula F

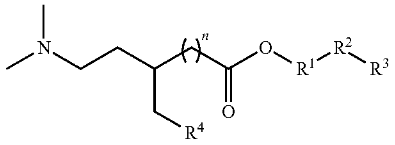

wherein, $R^1$ is $C_1$-$C_{12}$ alkyl;

$R^2$ is cis-alkenyl;

$R^3$ is $C_1$-$C_{12}$ alkyl;

$R^4$ is $C_1$-$C_{12}$ alkyl; and n is 0-12.

In embodiment 12, the composition of embodiment 11 is provided, wherein $R^1$ is $C_1$;

$R^2$ is cis-alkenyl;

$R^3$ is $C_4$-$C_{10}$ alkyl;

$R^4$ is $C_5$-$C_8$ alkyl or absent; and n is 4, 6, 8, 9, or 10.

In embodiment 13, a composition is provided comprising:

a lipid nanoparticle (LNP) comprising (a) the monoester cationic lipid of any of embodiments 1-12;

(b) a phospholipid;

(c) cholesterol; and (d) a PEG-lipid; and a polynucleotide, wherein the polynucleotide is at least partially encapsulated in the LNP. In some embodiments, the polynucleotide is fully encapsulated in the LNP.

In embodiment 14, a composition is provided comprising:

a lipid nanoparticle (LNP) comprising (a) a monoester cationic lipid selected from the group consisting of: (20Z,23Z)-nonacosa-20,23-dien-10-yl 3-(dimethylamino)-propanoate, (Z)-undec-2-en-1-yl 8-(2-(dimethylamino)ethyl)heptadecanoate, (Z)-non-2-en-1-yl 10-(2-(dimethylamino)ethyl)nonadecanoate, (Z)-tridec-2-en-1-yl 6-(2-(dimethylamino)ethyl)pentadecanoate, pentyl (14Z,17Z)-4-(2-(dimethylamino)ethyl)tricosa-14,17-dienoate, (Z)-oct-2-en-1-yl 11-(2-(dimethylamino)ethyl)icosanoate, (Z)-hept-2-en-1-yl 12-(2-(dimethylamino)ethyl)henicosanoate, methyl (Z)-

18-(2-(dimethylamino)-ethyl)heptacos-7-enoate, and combinations thereof;

(b) a phospholipid;

(c) cholesterol; and (d) a PEG-lipid; and a polynucleotide, wherein the polynucleotide is at least partially encapsulated in the LNP.

In embodiment 15, the composition of any of embodiments 1-14 is provided, wherein the composition formulated with the monoester cationic lipid provides improved tolerability compared to a composition formulated without a monoester cationic lipid.

In embodiment 16, the composition of any of embodiments 13-14 is provided, wherein the LNP comprises 30-65 mole % monoester cationic lipid, 5-30 mole % phospholipid, 10-40 mole % cholesterol, and 0.5-4 mole % PEG-lipid.

In embodiment 17, the composition of any of embodiments 13-14 is provided, wherein the LNP comprises 55-65 mole % monoester cationic lipid, 5-15 mole % phospholipid, 25-35% cholesterol, and 1-2.5 mole % PEG-lipid.

In embodiment 18, the composition of any of embodiments 13-17 is provided, wherein the LNP comprises DSPC, cholesterol, PEG2000-DMG, and a monoester selected from the group consisting of: (20Z,23Z)-nonacosa-20,23-dien-10-yl 3-(dimethylamino)-propanoate, (Z)-undec-2-en-1-yl 8-(2-(dimethylamino)ethyl)heptadecanoate, (Z)-non-2-en-1-yl 10-(2-(dimethylamino)ethyl)nonadecanoate, (Z)-tridec-2-en-1-yl 6-(2-(dimethylamino)ethyl)pentadecanoate, pentyl (14Z,17Z)-4-(2-(dimethylamino)ethyl)tricosa-14,17-dienoate, (Z)-oct-2-en-1-yl 11-(2-(dimethylamino)ethyl) icosanoate, (Z)-hept-2-en-1-yl 12-(2-(dimethylamino)ethyl) henicosanoate, methyl (Z)-18-(2-(dimethylamino)-ethyl) heptacos-7-enoate, or combinations thereof.

In embodiment 19, the composition of any of embodiments 13-18 is provided, wherein the LNP comprises DSPC in the amount of about 5-15 mole %, cholesterol in the amount of about 25-35 mole %, PEG2000-DMG in the amount of about 1-2.5 mole %, and a monoester selected from the group consisting of: (20Z,23Z)-nonacosa-20,23-dien-10-yl 3-(dimethylamino)-propanoate, (Z)-undec-2-en-1-yl 8-(2-(dimethylamino)ethyl)heptadecanoate, (Z)-non-2-en-1-yl 10-(2-(dimethylamino)ethyl)nonadecanoate, (Z)-tridec-2-en-1-yl 6-(2-(dimethylamino)ethyl)pentadecanoate, pentyl (14Z,17Z)-4-(2-(dimethylamino)ethyl)tricosa-14,17-dienoate, (Z)-oct-2-en-1-yl 11-(2-(dimethylamino)ethyl)icosanoate, (Z)-hept-2-en-1-yl 12-(2-(dimethylamino)ethyl) henicosanoate, methyl (Z)-18-(2-(dimethylamino)-ethyl) heptacos-7-enoate, or combinations thereof in the amount of about 55-65 mole %.

In embodiment 20, a composition is provided including:

(a) a monoester cationic lipid having the structure set forth in Formula A:

Formula A

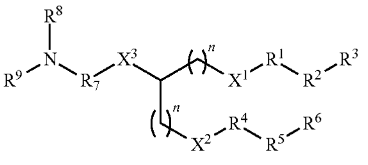

wherein, $X^2$ is

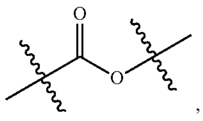
,
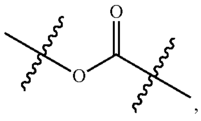
, or absent;

$X^3$ is

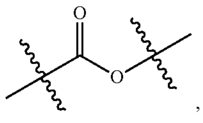
,
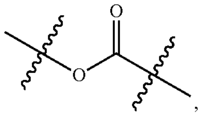
, or absent;

$R^3$ is $C_1$-$C_{12}$ alkyl, $X^1$—$R^1$—$R^2$, $R^1$—$X^1$—$R^2$ or absent;

$R^4$ is $C_1$-$C_{12}$ alkyl, $C_1$-$C_{12}$ heteroalkyl, or absent;

$R^5$ is $C_1$-$C_{12}$ alkyl, or absent;

$R^6$ is $C_1$-$C_{12}$ alkyl or absent;

$R^7$ is $C_1$-$C_{12}$ alkyl, $C_1$-$C_{12}$ heteroalkyl, or absent;

$R^8$ is $C_1$-$C_{12}$ alkyl, $C_1$-$C_{12}$ heteroalkyl;

$R^9$ is $C_1$-$C_{12}$ alkyl, $C_1$-$C_{12}$ heteroalkyl;

optionally, $R^8$ and $R^9$, together with the nitrogen atom to which they are attached, can join to form a 4- to 8-membered monocyclic heterocycloalkyl group;

each $X^1$ is independently

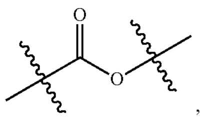
,
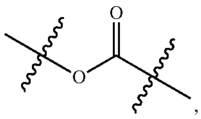
, cis-alkenyl, trans-alkenyl, or absent, each $R^1$ is independently $C_1$-$C_{12}$ alkyl, $C_1$-$C_{12}$ heteroalkyl, or absent; each $R^2$ is independently $C_1$-$C_{12}$ alkyl, cis-alkenyl, trans-alkenyl, or absent; and each n is independently 0-12;

(b) a phospholipid;

(c) cholesterol;

(d) a PEG-lipid; and (e) a polynucleotide, wherein a composition formulated with the monoester cationic lipid having the structure set forth in Formula A provides improved tolerability compared to a composition formulated without the monoester cationic lipid having the structure set forth in Formula A.

In embodiment 21, a composition is provided including:

(a) a monoester cationic lipid having the structure set forth in Formula B:

Formula B

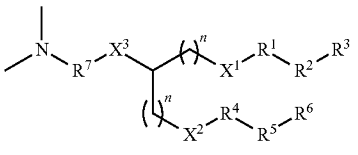

wherein, $X^2$ is

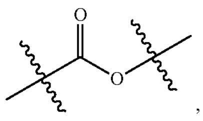,
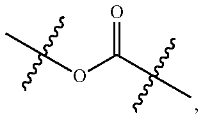, or absent, $X^3$ is

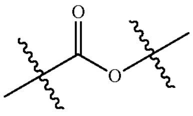 [SMILES: *OC(*)=O],
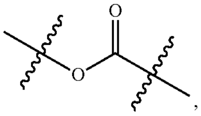, or absent;

$R^3$ is $C_1$-$C_{12}$ alkyl, $X^1$—$R^1$—$R^2$, $R^1$—$X^1$—$R^2$ or absent;

$R^4$ is $C_1$-$C_{12}$ alkyl, $C_1$-$C_{12}$ heteroalkyl, or absent;

$R^5$ is $C_1$-$C_{12}$ alkyl, or absent;

$R^6$ is $C_1$-$C_{12}$ alkyl or absent;

$R^7$ is $C_1$-$C_{12}$ alkyl, $C_1$-$C_{12}$ heteroalkyl, or absent;

each $X^1$ is independently

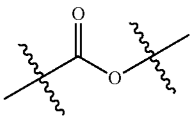 [SMILES: *OC(*)=O],
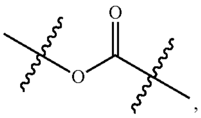, cis-alkenyl, trans-alkenyl, or absent, each $R^1$ is independently $C_1$-$C_{12}$ alkyl, $C_1$-$C_{12}$ heteroalkyl, or absent, each $R^2$ is independently $C_1$-$C_{12}$ alkyl, cis-alkenyl, trans-alkenyl, or absent, and each n is independently 0-12, (b) a phospholipid;

(c) cholesterol;

(d) a PEG-lipid; and (e) a polynucleotide, wherein a composition formulated with the monoester cationic lipid having the structure set forth in Formula B provides improved tolerability compared to a composition formulated without the monoester cationic lipid having the structure set forth in Formula B.

In embodiment 21, a composition is provided including:

(a) a monoester cationic lipid having the structure set forth in Formula C:

Formula C

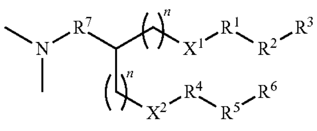

wherein, $X^2$ is

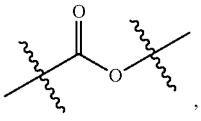,
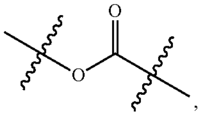, or absent;

$R^3$ is $C_1$-$C_{12}$ alkyl, $X^1$—$R^1$—$R^2$, $R^1$—$X^1$—$R^2$ or absent;

$R^4$ is $C_1$-$C_{12}$ alkyl, $C_1$-$C_{12}$ heteroalkyl, or absent, $R^5$ is $C_1$-$C_{12}$ alkyl, or absent, $R^6$ is $C_1$-$C_{12}$ alkyl or absent, $R^7$ is $C_1$-$C_{12}$ alkyl, $C_1$-$C_{12}$ heteroalkyl, or absent, each $X^1$ is independently

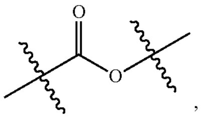,
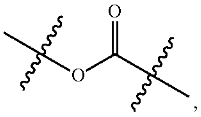, cis-alkenyl, trans-alkenyl, or absent, each $R^1$ is independently $C_1$-$C_{12}$ alkyl, $C_1$-$C_{12}$ heteroalkyl, or absent, each $R^2$ is independently $C_1$-$C_{12}$ alkyl, cis-alkenyl, trans-alkenyl, or absent, and each n is independently 0-12, (b) a phospholipid;

(c) cholesterol;

(d) a PEG-lipid, and (e) a polynucleotide, wherein a composition formulated with the monoester cationic lipid having the structure set forth in Formula C provides improved tolerability compared to a composition formulated without the monoester cationic lipid having the structure set forth in Formula C.

In embodiment 22, a composition is provided including:

(a) a monoester cationic lipid having the structure set forth in Formula D:

Formula D

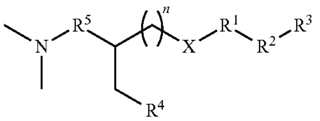

wherein, $R^3$ is $C_1$-$C_{12}$ alkyl, X—$R^1$—$R^2$, $R^1$—X—$R^2$ or absent, $R^4$ is $C_1$-$C_{12}$ alkyl, $C_1$-$C_{12}$ heteroalkyl, or absent, $R^5$ is $C_1$-$C_{12}$ alkyl, each X is independently

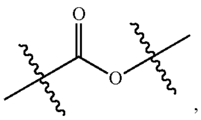,
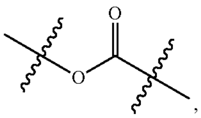, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and n is 0-12, (b) a phospholipid;

(c) cholesterol;

(d) a PEG-lipid; and (e) a polynucleotide, wherein a composition formulated with the monoester cationic lipid having the structure set forth in Formula D provides improved tolerability compared to a composition formulated without the monoester cationic lipid having the structure set forth in Formula D.

In embodiment 23, the composition of embodiment 21 is provided, wherein $R^3$ is $C_4$-$C_{10}$ alkyl, $R^1$—X—$R^2$ or absent;

$R^4$ is $C_5$-$C_8$ alkyl or absent;

$R^5$ is $C_2$ alkyl;

each X is independently

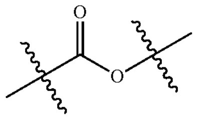 [SMILES: *OC(*)=O]

or cis-alkenyl;

each $R^1$ is independently $C_1$-$C_5$ alkyl or absent;

each $R^2$ is independently $C_1$ alkyl, cis-alkenyl, or absent; and n is 4, 6, 8, 9, or 10.

In embodiment 24, a composition is provided including: a monoester cationic lipid having the structure set forth in Formula E Formula E

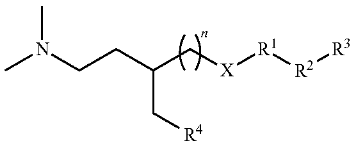

wherein, $R^3$ is $C_1$-$C_{12}$ alkyl, X—$R^1$—$R^2$, $R^1$—X—$R^2$, or absent;

$R^4$ is $C_1$-$C_{12}$ alkyl, $C_1$-$C_{12}$ heteroalkyl, or absent;

each X is independently

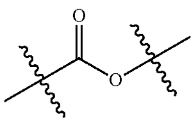
,
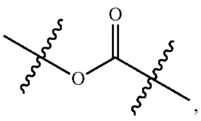
, cis-alkenyl, trans-alkenyl, or absent;

each $R^1$ is independently $C_1$-$C_{12}$ alkyl, $C_1$-$C_{12}$ heteroalkyl, or absent;

each $R^2$ is independently $C_1$-$C_{12}$ alkyl, cis-alkenyl, trans-alkenyl, or absent; and each n is independently 0-12, wherein a composition formulated with the monoester cationic lipid having the structure set forth in Formula E provides improved tolerability compared to a composition formulated without the monoester cationic lipid having the structure set forth in Formula E.

In embodiment 25, a composition is provided including: a monoester cationic lipid having the structure set forth in Formula F Formula F

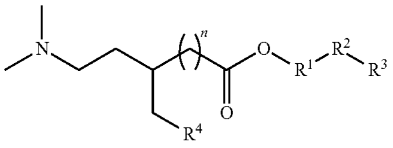

wherein, $R^1$ is $C_1$-$C_{12}$ alkyl;

$R^2$ is cis-alkenyl;

$R^3$ is $C_1$-$C_{12}$ alkyl;

$R^4$ is $C_1$-$C_{12}$ alkyl; and n is 0-12, wherein a composition formulated with the monoester cationic lipid having the structure set forth in Formula F provides improved tolerability compared to a composition formulated without the monoester cationic lipid having the structure set forth in Formula F.

In embodiment 26, a composition is provided including:

(a) a monoester cationic lipid selected from the group consisting of: (20Z,23Z)-nonacosa-20,23-dien-10-yl 3-(dimethylamino)-propanoate, (Z)-undec-2-en-1-yl 8-(2-(dimethylamino)ethyl)heptadecanoate, (Z)-non-2-en-1-yl 10-(2-(dimethylamino)ethyl)nonadecanoate, (Z)-tridec-2-en-1-yl 6-(2-(dimethylamino)ethyl)pentadecanoate, pentyl (14Z,17Z)-4-(2-(dimethylamino)ethyl)tricosa-14,17-dienoate, (Z)-oct-2-en-1-yl 11-(2-(dimethylamino)ethyl)icosanoate, (Z)-hept-2-en-1-yl 12-(2-(dimethylamino)ethyl)henicosanoate, methyl (Z)-18-(2-(dimethylamino)-ethyl)heptacos-7-enoate, and combinations thereof, (b) a phospholipid;

(c) cholesterol;

(d) a PEG-lipid; and (e) a polynucleotide, wherein a composition formulated with the monoester cationic lipid provides improved tolerability compared to a composition formulated without the monoester cationic lipid.

In embodiment 27, the composition of any of embodiments 1-26 is provided, wherein each X is independently

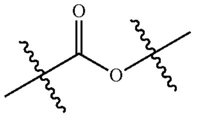

or cis-alkenyl.

In embodiment 28, the composition of any of embodiments 1-27 is provided, wherein each $R^1$ is independently $C_1$-$C_5$ alkyl or absent.

In embodiment 29, the composition of any of embodiments 1-28 is provided, wherein each $R^2$ is independently $C_1$ alkyl, cis-alkenyl, or absent.

In embodiment 30, the composition of any of embodiments 1-29 is provided, wherein each $R^3$ is independently $C_1$-$C_{10}$ alkyl, $R^1$—$X^1$—$R^2$, or absent.

In embodiment 31, the composition of any of embodiments 1-30 is provided, wherein each $R^4$ is independently $C_1$-$C_8$ alkyl or absent.

In embodiment 32, the composition of any of embodiments 1-31 is provided, wherein each $R^5$ is independently $C_1$-$C_2$ alkyl or absent.

In embodiment 33, the composition of any of embodiments 1-32 is provided, wherein each n is independently 4, 6, 8, 9, or 10.

In embodiment 34, the composition of any of embodiments 1-33 is provided, wherein the monoester is selected from the group consisting of:

(20Z,23Z)-nonacosa-20,23-dien-10-yl 3-(dimethylamino)-propanoate;

(Z)-undec-2-en-1-yl 8-(2-(dimethylamino)ethyl)heptadecanoate;

(Z)-non-2-en-1-yl 10-(2-(dimethylamino)ethyl)nonadecanoate;

(Z)-tridec-2-en-1-yl 6-(2-(dimethylamino)ethyl)pentadecanoate;

pentyl (14Z,17Z)-4-(2-(dimethylamino)ethyl)tricosa-14,17-dienoate;

(Z)-oct-2-en-1-yl 11-(2-(dimethylamino)ethyl)icosanoate;

(Z)-hept-2-en-1-yl 12-(2-(dimethylamino)ethyl)henicosanoate;

methyl (Z)-18-(2-(dimethylamino)-ethyl)heptacos-7-enoate;

and combinations thereof.

In embodiment 35, the composition of embodiments 1-34 is provided, wherein the monoester is present in the amount of about 55-65 mole %.

In embodiment 36, a composition is provided comprising:

a lipid nanoparticle (LNP) comprising:

a monoester cationic lipid selected from the group consisting of:

(20Z,23Z)-nonacosa-20,23-dien-10-yl 3-(dimethylamino)-propanoate;

(Z)-undec-2-en-1-yl 8-(2-(dimethylamino)ethyl)heptadecanoate;

(Z)-non-2-en-1-yl 10-(2-(dimethylamino)ethyl)nonadecanoate;

(Z)-tridec-2-en-1-yl 6-(2-(dimethylamino)ethyl)pentadecanoate;

pentyl (14Z,17Z)-4-(2-(dimethylamino)ethyl)tricosa-14,17-dienoate;

(Z)-oct-2-en-1-yl 11-(2-(dimethylamino)ethyl)icosanoate;

(Z)-hept-2-en-1-yl 12-(2-(dimethylamino)ethyl)henicosanoate;

methyl (Z)-18-(2-(dimethylamino)-ethyl)heptacos-7-enoate;

and combinations thereof, a phospholipid, cholesterol, and a PEG-lipid, and a polynucleotide, wherein the polynucleotide is at least partially encapsulated in the LNP.

In embodiment 37, the composition of any of embodiments 1-36 is provided, wherein a composition formulated with the monoester cationic lipid provides improved tolerability compared to a composition formulated without a monoester cationic lipid.

In embodiment 38, the composition of any of embodiments 1-37 is provided wherein the LNP comprises 30-65 mole % monoester cationic lipid, 5-30 mole % phospholipid, 10-40 mole % cholesterol, and 0.5-4 mole % PEG-lipid.

In embodiment 39, the composition of any of embodiments 1-38 is provided, wherein the LNP comprises 55-65 mole % monoester cationic lipid, 5-15 mole % phospholipid, 25-35% cholesterol, and 1-2.5 mole % PEG-lipid.

In embodiment 40, the composition of any of embodiments 1-39 is provided, wherein the phospholipid is DSPC.

In embodiment 41, the composition of embodiment 40 is provided, wherein the DSPC is present in the amount of about 5-15 mole %.

In embodiment 42, the composition of any of embodiments 1-41 is provided, wherein the PEG-lipid is PEG2000-DMG.

In embodiment 43, the composition of embodiment 42, wherein the PEG2000-DMG is present in the amount of about 5-15 mole %.

In embodiment 44, a composition is provided comprising:

a buffer; and a lipid nanoparticle composition comprising:

a polynucleotide at least partially encapsulated in a lipid nanoparticle, wherein the lipid nanoparticle comprises:

a phospholipid, cholesterol, a PEG-lipid, and a monoester cationic lipid having the structure set forth in Formula D:

Formula D

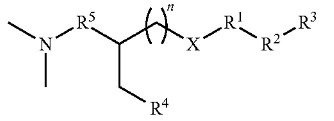

wherein, $R^3$ is $C_4$-$C_{10}$ alkyl, $R^1$—X—$R^2$ or absent;

$R^4$ is $C_5$-$C_8$ alkyl or absent;

$R^5$ is $C_2$ alkyl;

each X is independently

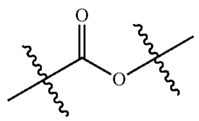 [SMILES: *OC(*)=O]

or cis-alkenyl;

each $R^1$ is independently $C_1$-$C_5$ alkyl or absent;

each $R^2$ is independently $C_1$ alkyl, cis-alkenyl, or absent; and n is 4, 6, 8, 9, or 10.

In embodiment 45, the composition of embodiment 44 is provided, wherein the vaccine provides improved tolerability compared to a composition formulated without the monoester cationic lipid having the structure set forth in Formula D.

In embodiment 46, a composition is provided comprising:

a buffer; and a lipid nanoparticle composition comprising:

a polynucleotide at least partially encapsulated in a lipid nanoparticle, wherein the lipid nanoparticle comprises:

a phospholipid;

cholesterol;

a PEG-lipid; and a monoester cationic lipid having the structure set forth in Formula F:

Formula F

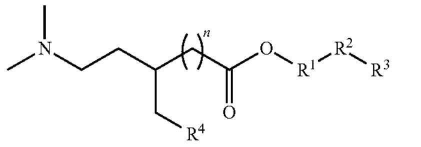

wherein, $R^1$ is $C_1$;

$R^2$ is cis-alkenyl;

$R^3$ is $C_4$-$C_{10}$ alkyl;

$R^4$ is $C_5$-$C_8$ alkyl or absent; and n is 4, 6, 8, 9, or 10.

In embodiment 47, the composition of embodiment 44 is provided, wherein the vaccine provides improved tolerability compared to a composition formulated without the monoester cationic lipid having the structure set forth in Formula F.

In embodiment 48, a composition is provided comprising:

a buffer; and a lipid nanoparticle composition comprising:

a polynucleotide at least partially encapsulated in a lipid nanoparticle, wherein the lipid nanoparticle comprises:

a phospholipid;

cholesterol;

a PEG-lipid; and a monoester cationic lipid selected from the group consisting of: (20Z,23Z)-nonacosa-20,23-dien-10-yl 3-(dimethylamino)-propanoate, (Z)-undec-2-en-1-yl 8-(2-(dimethylamino)ethyl)heptadecanoate, (Z)-non-2-en-1-yl 10-(2-(dimethylamino)ethyl)nonadecanoate, (Z)-tridec-2-en-1-yl 6-(2-(dimethylamino)ethyl) pentadecanoate, pentyl (14Z,17Z)-4-(2-(dimethylamino)ethyl)tricosa-14,17-dienoate, (Z)-oct-2-en-1-yl 11-(2-(dimethylamino)ethyl)icosanoate, (Z)-hept-2-en-1-yl 12-(2-(dimethylamino)ethyl) henicosanoate, methyl (Z)-18-(2-(dimethylamino)-ethyl)heptacos-7-enoate, wherein a vaccine formulated with the monoester cationic provides improved tolerability compared to the same composition formulated without the monoester cationic lipid In embodiment 49, the composition of any of embodiments 1-48 is provided, wherein the vaccine is formulated for intramuscular administration.

In embodiment 50, the composition of any of embodiments 1-49 is provided, wherein the vaccine is an intramuscular vaccine providing a terminal half-life of elimination of less than 100 hours after administration.

In embodiment 51. the composition of any of embodiments 1-50 is provided, wherein the vaccine is an intramuscular vaccine providing a terminal half-life of elimination of less than 10 hours after administration.

In embodiment 52, the composition of any of embodiments 1-51 is provided, wherein the vaccine is an intramuscular vaccine providing a terminal half-life of elimination of between 4 to 10 hours after administration.

In embodiment 53, the composition of any of embodiments 1-52 is provided, wherein the vaccine is an intramuscular vaccine providing a terminal half-life of elimination of between 5 to 8 hours after administration.

In embodiment 54, the composition of any of embodiments 1-53 is provided, wherein the improved tolerability is a systemic tolerability.

In embodiment 55, the composition of any of embodiments 1-54 is provided, wherein the improved tolerability is a local tolerability.

In embodiments 56, a composition is provided comprising (11Z, 14Z)-icosa-11,14-dienal.

In embodiments 57, a composition is provided comprising (2E,13Z,16Z)-ethyl docosa-2,13,16-trienoate.

In embodiments 58, a composition is provided comprising (Z)-undec-2-en-1-ol.

In embodiments 59, a composition is provided comprising (Z)-non-2-en-1-ol.

In embodiments 60, a composition is provided comprising (Z)-tridec-2-en-1-ol.

In embodiments 61, a composition is provided comprising (Z)-oct-2-en-1-ol.

In embodiments 62, a composition is provided comprising ((Z)-hept-2-en-1-ol.

In embodiments 63, a composition is provided comprising 1-methoxy-4-((oct-7-yn-1-yloxy)methyl)benzene.

EXAMPLES

The invention is illustrated by the following examples. These examples illustrate, but do not limit the invention. For all of the examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Intermediates

Intermediate 1 and 5: Synthesis of (11Z, 14Z)-icosa-11,14-dienal and (2E,13Z,16Z)-ethyl docosa-2,13,16-trienoate

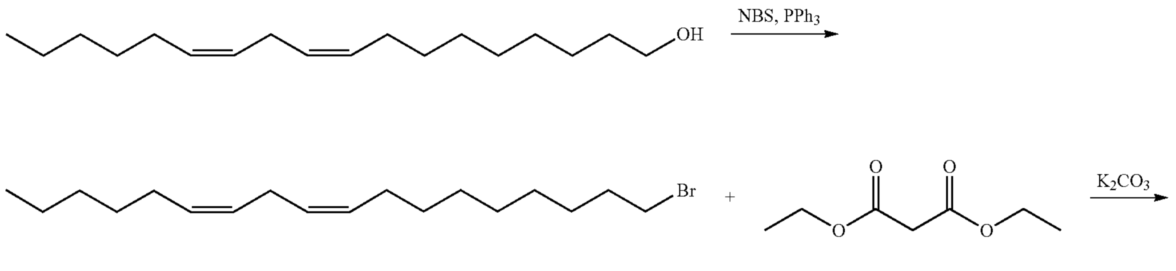

-continued

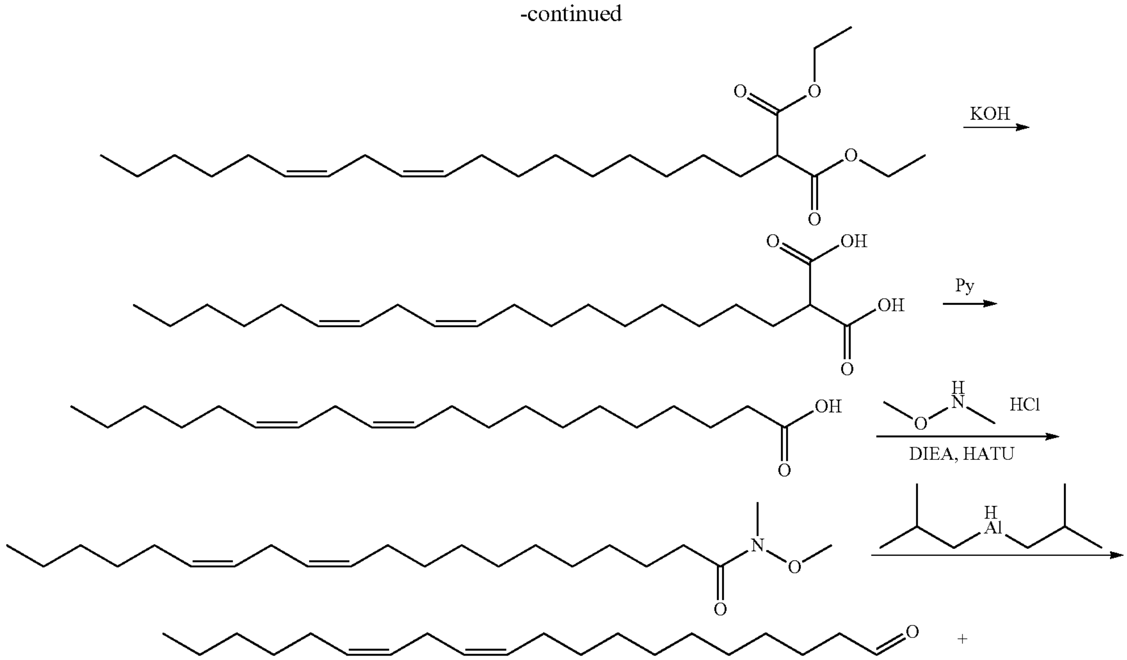

INTERMEDIATE 1

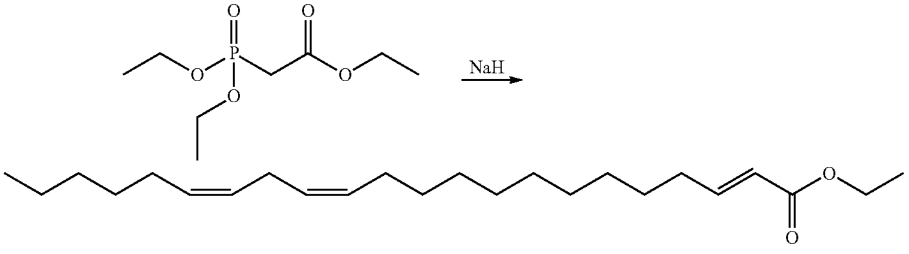

INTERMEDIATE 5

Step 1: Synthesis of (6Z, 9Z)-18-bromooctadeca-6, 9-diene

To a solution of (9Z, 12Z)-octadeca-9, 12-dien-1-ol (10 g, 37.5 mmol) and $Ph_3P$ (22.64 g, 86 mmol) in DCM (40 mL) was slowly added NBS (13.36 g, 75 mmol) at 0° C. The reaction mixture was stirred at 25° C. for 3 h under $N_2$. Then the reaction was diluted with $H_2O$ (150 mL), and the resulting mixture was extracted with DCM (200 mL*2). The combined organic extracts were washed with brine (200 mL), dried over anhydrous $Na_2SO_4$ and filtered. The filtrate was concentrated and the resulting mixture was purified by column chromatography ($SiO_2$, Pet. ether) to give (6Z,9Z)-18-bromooctadeca-6,9-diene (11 g, 26.7 mmol).

$^1H$ NMR (400 MHz, CHLOROFORM-d): δ=5.32-5.39 (m, 4H), 4.05 (t, J=6.80 Hz, 2H), 2.77 (t, J=6.80 Hz, 2H), 1.83-2.08 (m, 6H), 1.33-1.42 (m, 16H), 0.88 (t, J=7.60 Hz, 3H).

Step 2: Synthesis of Diethyl 2-((9Z, 12Z)-octadeca-9,12-dien-1-yl)malonate $K_2CO_3$ (20.98 g, 152 mmol) was added to diethyl malonate (24.32 g, 152 mmol) in a 1:1 mixture of THF (50 mL) and DMF (50 mL) at 0° C. Then (6Z, 9Z)-18-bromooctadeca-6, 9-diene (10 g, 30.4 mmol) was added to the reaction mixture. The mixture was heated 60° C. for 16 h under $N_2$. The resulting solution was filtered and washed with EtOAc (50 mL*3). The combined organic layers were washed with 1.0 M aqueous HCl to adjust pH to 3~4. The resulting solution was extracted with EtOAc (150 mL*3). The combined organic extracts were washed with water (160 mL), brine (160 mL), dried over anhydrous $Na_2SO_4$, and filtered. The filtrate was concentrated under reduced pressure. The residue was purified by column chromatography ($SiO_2$, Pet. ether:EtOAc=50:1 to 10:1) to give the desired product diethyl 2-((9Z, 12Z)-octadeca-9, 12-dien-1-yl)malonate (10 g, 19.58 mmol).

$^1H$ NMR (400 MHz, CHLOROFORM-d): δ=5.29-5.38 (m, 4H), 3.19 (q, J=7.2 Hz, 4H), 3.30 (t, J=7.60 Hz, 1H), 2.76 (t, J=6.40 Hz, 2H), 1.86-2.05 (m, 6H), 1.24-2.34 (m, 24H), 0.88 (t, J=7.20 Hz, 3H).

Step 3: Synthesis of 2-((9Z, 12Z)-octadeca-9,12-dien-1-yl)malonic Acid

KOH (20.60 g, 367 mmol) was added to diethyl 2-((9Z, 12Z)-octadeca-9,12-dien-1-yl)malonate (15 g, 36.7 mmol) in MeOH (150 mL) at 0° C. The mixture was heated 25° C. for 2 h under $N_2$ atmosphere. The reaction was concentrated. Then 1.0 M aqueous HCl was added to the resulting solution to adjust pH to 4~5. The mixture was extracted with DCM (500 mL*3) and $H_2O$ (500 mL). The combined organic layer was dried over anhydrous $Na_2SO_4$, and the solvent was removed in vacuo to give 2-((9Z, 12Z)-octadeca-9,12-dien-1-yl)malonic acid (11 g, 23.40 mmol), which was used in the subsequent step without further purification.

$^1$H NMR (400 MHz, DMSO-d6): δ=12.64 (brs, 2H), 5.26-5.36 (m, 4H), 3.16 (t, J=7.2 Hz, 1H), 2.73 (t, J=6.00 Hz, 2H), 1.98-2.02 (m, 4H), 1.60-1.70 (m, 2H), 1.23-1.32 (m, 18H), 0.85 (t, J=7.20 Hz, 3H).

Step 4: Synthesis of (11Z, 14Z)-icosa-11,14-dienoic Acid

Pyridine (11.36 mL, 140 mmol) was added to 2-((9Z, 12Z)-octadeca-9,12-dien-1-yl)malonic acid (11 g, 31.2 mmol) in toluene (170 mL). The mixture was heated 120° C. for 14 h under $N_2$. The resulting solution was concentrated under reduced pressure to give (11Z, 14Z)-icosa-11,14-dienoic acid (11 g, 26.7 mmol), which was used in the subsequent step without further purification.

$^1$H NMR (400 MHz, DMSO-d6): δ=11.98 (brs, 1H), 5.26-5.35 (m, 4H), 2.73 (t, J=6.00 Hz, 2H), 2.17 (t, J=7.20 Hz, 2H), 1.98-2.01 (m, 4H), 1.40-1.50 (m, 2H), 1.23-1.31 (m, 18H), 0.85 (t, J=7.20 Hz, 3H).

Step 5: Synthesis of (11Z, 14Z)—N-methoxy-N-methylicosa-11, 14-dienamide (11Z, 14Z)-icosa-11,14-dienoic acid (11 g, 35.7 mmol) and DIEA (31.1 mL, 178 mmol) was dissolved in DCM (100 mL). HATU (20.34 g, 53.5 mmol) was added and the mixture was stirred for 1 h. Then N, O-dimethylhydroxylamine hydrochloride (5.22 g, 53.5 mmol) was added. The reaction was stirred at 25° C. for 16 h. The reaction was extracted with DCM (100 mL*3), washed with brine (100 mL), dried over $Na_2SO_4$, filtered, and concentrated in vacuo. The residue was purified by column chromatography ($SiO_2$, Pet. ether:EtOAc=20:1) to give (11Z,14Z)—N-methoxy-N-methylicosa-11,14-dienamide (12 g, 27.3 mmol). MS: m/z=352.3 (M+1).

$^1$H NMR (400 MHz, CHLOROFORM-d): δ=5.30-5.38 (m, 4H), 3.67 (s, 3H), 3.17 (s, 3H), 2.77 (t, J=6.40 Hz, 2H), 2.38-2.40 (m, 2H), 2.01-2.05 (m, 4H), 1.59-1.61 (m, 2H), 1.27-1.38 (m, 18H), 0.883 (t, J=6.80 Hz, 3H).

Step 6: Synthesis of (11Z, 14Z)-icosa-11,14-dienal (Intermediate 1)

To a solution of (11Z,14Z)—N-methoxy-N-methylicosa-11,14-dienamide (10 g, 28.4 mmol) in DCM (100 mL) was slowly added DIBAL-H (56.9 mL, 56.9 mmol) at −78° C. under $N_2$. The reaction mixture was stirred at −78° C. for 2 h. Then the mixture was quenched with sat. aq. sodium potassium tartrate tetrahydrate solution (100 mL), and the mixture was stirred for 1 h. Then it was extracted with DCM (100 mL*2). The combined organic extracts were washed with brine (200 mL), dried over anhydrous $Na_2SO_4$, and filtered. The filtrated was concentrated in vacuo, and the residue was purified by column chromatography ($SiO_2$, Pet. ether:EtOAc=99:1 to 25:1) to give the product (11Z, 14Z)-icosa-11,14-dienal (6 g, 16.41 mmol).

$^1$H NMR (400 MHz, CHLOROFORM-d): δ=9.76 (s, 1H), 5.30-5.42 (m, 4H), 2.77 (t, J=6.00 Hz, 2H), 2.38-2.42 (m, 2H), 2.01-2.07 (m, 4H), 1.62-1.64 (m, 2H), 1.25-1.35 (m, 18H), 0.883 (t, J=6.80 Hz, 3H).

Step 7: Synthesis of (2E,13Z,16Z)-ethyl docosa-2,13,16-trienoate (Intermediate 5)

To a solution of ethyl 2-(diethoxyphosphoryl)acetate (9.93 g, 44.3 mmol) in THF (140 mL) was slowly added NaH (1.477 g, 36.9 mmol) at 0° C. under $N_2$. The reaction mixture was stirred for 20 min at 0° C. Then the solution of (11Z, 14Z)-icosa-11, 14-dienal (7.2 g, 24.62 mmol) in THE (10 mL) was added to the above mixture at 0° C. The reaction mixture was stirred at 25° C. for 13 h. The mixture was quenched with sat. aq. $NH_4Cl$ (100 mL), then water (100 mL) was added to the above mixture at 0° C., and the resulting mixture was extracted with EtOAc (200 mL*2). The combined organic extracts were washed with brine (500 ml), dried over anh. $Na_2SO_4$, and filtered. The filtrate was concentrated in vacuo and the residue was purified by column chromatography ($SiO_2$, Pet. ether:EtOAc=20:1) to give (2E,13Z,16Z)-ethyl docosa-2,13,16-trienoate (6.5 g, 14.34 mmol).

$^1$H NMR (400 MHz, CHLOROFORM-d): δ=6.96 (dt, J=15.2, 7.2 Hz, 1H), 5.73-5.85 (m, 1H), 5.30-5.42 (m, 4H), 4.14-4.22 (m, 2H), 2.77 (t, J=6.4 Hz, 2H), 2.14-2.22 (m, 2H), 2.04 (q, J=6.8 Hz, 4H), 1.40-1.47 (m, 2H), 1.27-1.36 (m, 21H), 0.87-0.90 (m, 3H).

Intermediate 2: Synthesis of (Z)-undec-2-en-1-ol

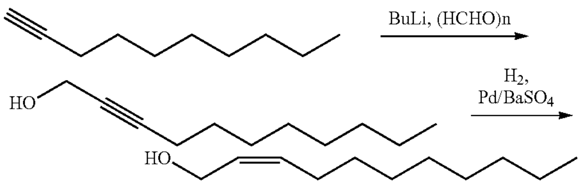

INTERMEDIATE 2

Step 1: Synthesis of Undec-2-yn-1-ol

To a solution of dec-1-yne (9 g, 65.1 mmol) in THF (72 mL) was slowly added n-butyllithium (31.8 mL, 79 mmol, 2.5 M) at −78° C. under $N_2$. The reaction mixture was allowed to warm to 0° C. and stirred for 1 h. Then the reaction mixture was cooled to −78° C., and paraformaldehyde (2.346 g, 78 mmol) was added. The reaction mixture was again warmed to 25° C. and stirred for 16 h. The reaction was quenched with sat. aq. $NH_4Cl$ (70 mL) at 0° C., and the resulting mixture was extracted with EtOAc (70 mL*2). The combined organic extracts were washed with water (70 mL), brine (70 mL), dried over anhydrous $Na_2SO_4$, and filtered. The filtrate was concentrated in vacuo and the residue was purified by column chromatography ($SiO_2$, Pet. ether:EtOAc=20:1) to give undec-2-yn-1-ol (8 g, 38.0 mmol).

$^1$H NMR (400 MHz, CHLOROFORM-d): δ=4.25 (s, 2H), 2.18-2.22 (m, 2H), 1.26-1.57 (m, 13H), 0.88 (t, J=6.80 Hz, 3H).

Step 2: (Z)-undec-2-en-1-ol (Intermediate 2)

To a solution of undec-2-yn-1-ol (1 g, 5.94 mmol) in pyridine (10 mL) at 0° C. was slowly added $Pd/BaSO_4$ (0.1 g, 5% $Pd/BaSO_4$) under $H_2$ atmosphere (15 psi). The reaction mixture was allowed to warm to 25° C. and stirred for 28 h. The resulting mixture was filtered and the filtrate was extracted with EtOAc (200 mL*3). The organic phase were washed with HCl (1 M, 100 mL*2), dried over anhydrous $Na_2SO_4$, filtered and concentrated in vacuo to give a crude product (Z)-undec-2-en-1-ol (900 mg, 5.29 mmol) which was used in subsequent chemistry without further purification.

$^1$H NMR (400 MHz, CHLOROFORM-d): δ=5.52-5.62 (m, 4H), 4.19 (d, J=6.00 Hz, 2H), 2.03-2.08 (m, 2H), 1.25-1.30 (m, 12H), 0.87 (t, J=6.80 Hz, 2H).

Intermediates 3, 4, 6, and 7: Synthesis of (Z)-non-2-en-1-ol, (Z)-tridec-2-en-1-ol, (Z)-oct-2-en-1-ol, (Z)-hept-2-en-1-ol INTERMEDIATES 3, 4, 6, and 7 were prepared using the same synthetic sequence as outlines for INTERMEDIATE 2 above replacing dec-1-yne with oct-1-yne, dodec-1-yne, hept-1-yne, or hex-1-yne, respectively.

Intermediate 8: Synthesis of 1-methoxy-4-((oct-7-yn-1-yloxy)methyl)benzene

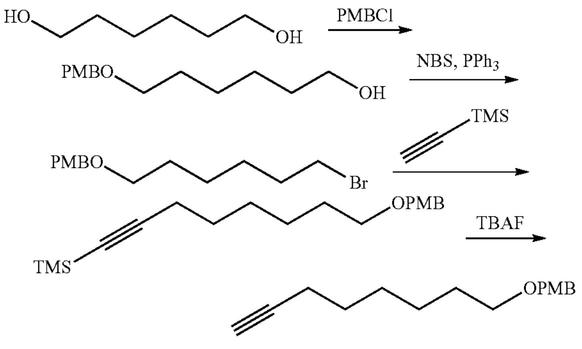

INTERMEDIATE 8

Step 1: Synthesis of 6-((4-methoxybenzyl)oxy)hexan-1-ol

To a solution of hexane-1,6-diol (31.7 g, 268 mmol) in anh. THF (500 mL) was added NaH (8.94 g, 223 mmol) at 0° C., and the mixture was stirred for 30 min at the same temp. Then 1-(chloromethyl)-4-methoxybenzene (35 g, 223 mmol) was added slowly at 0° C. The mixture was stirred at 50° C. for 16 h. After cooling to room temperature and then to 0° C., cold $H_2O$ was added at 0° C., the two layers were separated, and the aqueous phase was extracted with EtOAc (50 mL). The combined organic layers were washed with $H_2O$ and brine, dried over $Na_2SO_4$, filtered, and concentrated in vacuo. The residue was purified by column chromatography ($SiO_2$, Pet. ether:EtOAc=10:1 to 5:1) to give 6-((4-methoxybenzyl)oxy)hexan-1-ol (40 g, 159 mmol).

$^1$H NMR (400 MHz, CHLOROFORM-d): δ=7.24~7.30 (m, 2H), 6.86~6.88 (m, 2H), 4.43 (s, 2H), 3.80 (s, 3H), 3.61~3.66 (m, 3H), 3.44 (t, J=7.4 Hz, 2H), 1.50~1.70 (m, 8H).

Step 2: Synthesis of 1-(((6-bromohexyl)oxy)methyl)-4-methoxybenzene

To a solution of 6-((4-methoxybenzyl)oxy)hexan-1-ol (38 g, 159 mmol) and triphenylphosphine (84 g, 319 mmol) in anh. THF (200 mL) was added 1-bromopyrrolidine-2,5-dione (56.8 g, 319 mmol) at 25° C. in 6 portions and the mixture was stirred for 2 h at the same temp. Cold $H_2O$ was added, the two layers were separated, and the aqueous phase was extracted with EtOAc (500 mL). The combined organic layers were washed with $H_2O$ and brine, dried over $Na_2SO_4$, filtered, and concentrated in vacuo. The residue was purified by column chromatography ($SiO_2$, Pet. ether) to give 1-(((6-bromohexyl)oxy)methyl)-4-methoxybenzene (30 g, 95 mmol).

$^1$H NMR (400 MHz, CHLOROFORM-d): δ=7.24~7.28 (m, 2H), 6.86~6.89 (m, 2H), 4.43 (s, 2H), 3.80 (s, 3H), 3.38~3.43 (m, 4H), 1.83~1.89 (m, 3H), 1.60~1.70 (m, 2H), 1.40~1.50 (m, 3H).

Step 3: (8-((4-methoxybenzyl)oxy)oct-1-yn-1-yl)trimethylsilane

A solution of n-butyllithium in THF (1.592 mL, 3.98 mmol) was added dropwise to a solution of ethynyltrimethylsilane (0.391 g, 3.98 mmol) in THF (8 mL) at −60° C., and then the reaction was allowed to warm to 0° C. for 30 min. The reaction was then cooled to −20° C. and HMPA (2 mL) was added dropwise followed by 1-(((6-bromohexyl)oxy)methyl)-4-methoxybenzene (1.0 g, 3.32 mmol). The reaction was stirred for 5 h at 0° C. and then at 20° C. for an additional 14 h. The reaction was quenched with sat. aq. $NH_4Cl$ and extracted into EtOAc, washed with brine, dried over $Na_2SO_4$, filtered, and concentrated in vacuo. The residue was purified by column chromatography ($SiO_2$, Pet. ether:EtOAc=10:1) to give (8-((4-methoxybenzyl)oxy)oct-1-yn-1-yl)trimethylsilane (0.73 g, 2.177 mmol).

$^1$H NMR (400 MHz, CHLOROFORM-d): δ=7.10~7.20 (m, 2H), 6.73 (d, J=8.8 Hz, 2H), 4.29 (s, 2H), 3.66 (s, 3H), 3.29 (t, J=6.4 Hz, 2H), 2.07 (t, J=7.2 Hz, 2H), 1.22~1.51 (m, 8H), 0.00 (s, 9H).

Step 4: 1-methoxy-4-((oct-7-yn-1-yloxy)methyl)benzene (Intermediate 8)

A mixture of (8-((4-methoxybenzyl)oxy)oct-1-yn-1-yl)trimethylsilane (8 g, 25.1 mmol) and tetrabutylammonium fluoride (50.2 mL, 50.2 mmol) were stirred at 20° C. for 16 h. Then the mixture was extracted into EtOAc, washed with brine, dried over $Na_2SO_4$, filtered, and concentrated in vacuo. The residue was purified by column chromatography ($SiO_2$, Pet. ether:EtOAc=20:1) to give 1-methoxy-4-((oct-7-yn-1-yloxy)methyl)benzene (5.9 g, 22.75 mmol).

$^1$H NMR (400 MHz, CHLOROFORM-d): δ=7.26 (t, J=4.0 Hz, 2H), 6.87 (d, J=8.4 Hz, 2H), 4.40 (s, 2H), 3.80 (s, 3H), 3.43 (t, J=6.8 Hz, 2H), 2.17~2.20 (m, 2H), 1.93 (s, 1H), 1.35~1.40 (s, 8H).

Example 1: Synthesis of Lipid 1, (20Z,23Z)-nonacosa-20,23-dien-10-yl 3-(dimethylamino)-propanoate

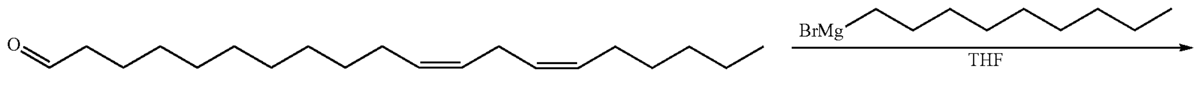

INTERMEDIATE 1

-continued

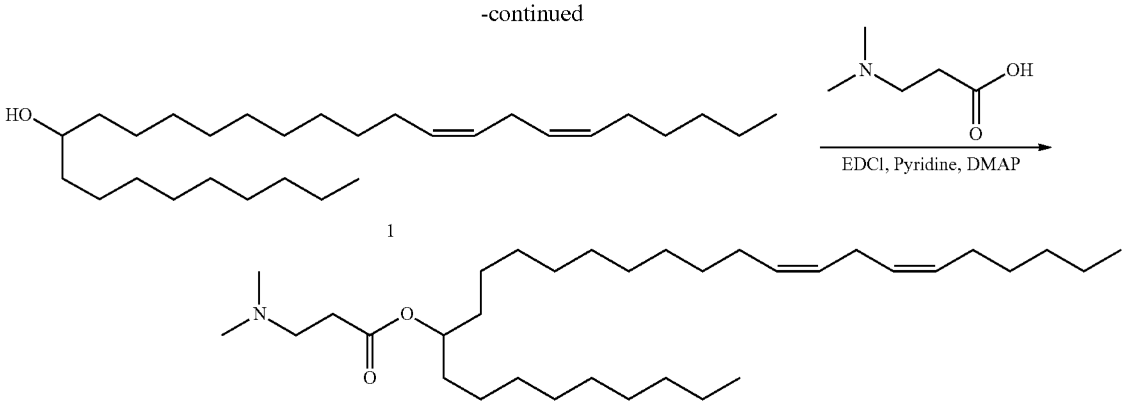

1

Lipid 1

Lipid 1, (20Z,23Z)-nonacosa-20,23-dien-10-yl 3-(dimethylamino)-propanoate, was formed according to the steps set forth below.

Step 1: Synthesis of (20Z,23Z)-nonacosa-20,23-dien-10-ol

A solution of freshly prepared nonylmagnesium bromide (14.19 mL, 6.84 mmol) solution was mixed with (11Z,14Z)-icosa-11,14-dienal (1.0 g, 3.42 mmol) in THF (2 mL) at 25° C. under $N_2$ balloon. The mixture was stirred at 25° C. for 2 h. The resulting mixture was cooled to 0° C. The resulting mixture was then quenched with sat. $NH_4Cl$ (10 mL) and the mixture was extracted with EtOAc (20 mL*2). The combined organic layers were washed with saturated aqueous NaCl solution (100 mL*2). The organic layers were then separated and dried over $Na_2SO_4$. The mixture was then filtered, and the filtrate was concentrated. The residue was then purified by column chromatography ($SiO_2$, Pet. ether: EtOAc=20:1) to form (20Z,23Z)-nonacosa-20,23-dien-10-ol) (1.1 g, 2.61 mmol).

$^1$H NMR (500 MHz, CHLOROFORM-d): δ=5.28~5.46 (m, 4H), 3.55~3.40 (m, 1H), 2.78 (t, J=7.0 Hz, 2H), 2.03~2.08 (m, 4H), 1.22~1.51 (m, 38H), 0.86~0.94 (m, 6H).

Step 2: Synthesis of (20Z,23Z)-nonacosa-20,23-dien-10-yl 3-(dimethylamino)propanoate A solution of (20Z,23Z)-nonacosa-20,23-dien-10-ol (1 g, 2.377 mmol), 3-(dimethylamino)propanoic acid hydrochloride (1.095 g, 7.13 mmol) in pyridine (30 mL) was mixed with EDC (1.822 g, 9.51 mmol) and DMAP (0.290 g, 2.377 mmol) at 0° C. The mixture was then warmed up to 40° C. and stirred for an additional 12 h. The resulting mixture was concentrated in vacuo. The residue was then diluted with water (20 mL) and extracted with DCM (50 mL*3). The organic layers were combined and washed with brine (100 mL*2). The organic layers were then separated, dried over $Na_2SO_4$, filtered and the filtrate was concentrated in vacuum. The residue was then purified by column chromatography ($SiO_2$, Pet. ether:EtOAc=5:1 to 1:1) to form the monoester cationic lipid of Lipid 1, having a structure as set forth below:

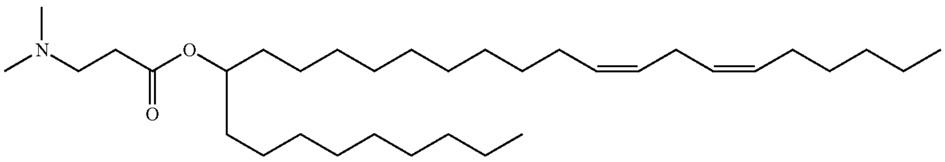 [SMILES: CCCCC/C=C\C/C=C\CCCCCCCCCC(CCCCCCCCC)OC(=O)CCN(C)C]

(20Z,23Z)-nonacosa-20,23-dien-10-yl 3-(dimethylamino)propanoate (400 mg, 0.769 mmol).

$^1$H NMR (500 MHz, CHLOROFORM-d): δ=5.21~5.47 (m, 4H), 4.86~4.92 (m, 1H), 3.38 (t, J=7.0 Hz, 2H), 2.82~2.90 (m, 8H), 2.78 (t, J=7.0 Hz, 2H), 2.03~2.08 (m, 4H), 1.45~1.55 (m, 4H), 1.19~1.41 (m, 34H), 0.86~0.92 (m, 6H). MS (ESI) m/z: 520.1 $[M+H]^+$.

Example 2: Synthesis of Lipid 2, (Z)-undec-2-en-1-yl 8-(2-(dimethylamino)ethyl)heptadecanoate

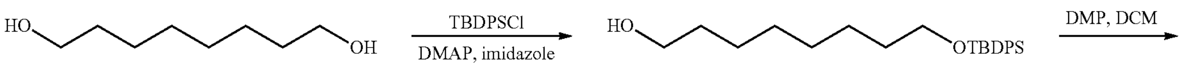

-continued

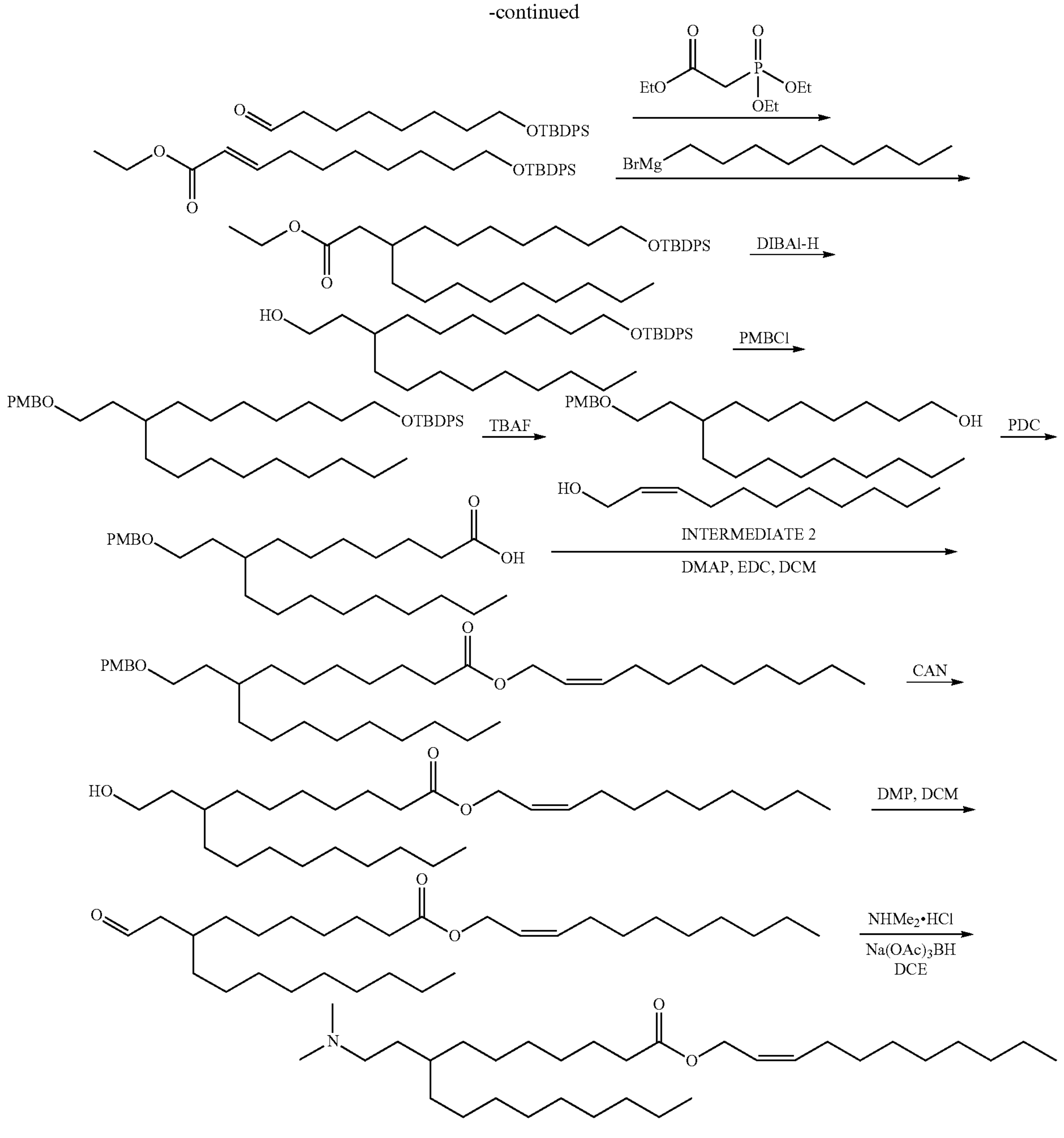

Lipid 2

Step 1: Synthesis of 8-((tert-butyldiphenylsilyl)oxy)octan-1-ol

A solution of octane-1,8-diol (25 g, 171 mmol) in THF (400 mL) was mixed with imidazole (23.28 g, 342 mmol) and DMAP (2.089 g, 17.10 mmol). Then TBDPSCl (43.5 ml, 169 mmol) was added to the above mixture at 0° C. The reaction mixture was heated to 25° C. and stirred for 16 h. The mixture was cooled to room temperature and water (500 mL) was added to it. The mixture was then extracted with EtOAc (500 mlx2). The combined organic layers were washed with brine (100 mL) and dried over anhydrous $Na_2SO_4$. The resulting mixture was filtered and concentrated in vacuo. The residue was purified by column chromatography ($SiO_2$, Pet. ether:EtOAc=20:1 to 5:1) to give 8-((tert-butyldiphenylsilyl)oxy)-octan-1-ol (35 g, 82 mmol).

$^1H$ NMR (500 MHz, CHLOROFORM-d): δ=7.67 (dd, J=1.8, 7.9 Hz, 4H), 7.50~7.31 (m, 6H), 3.68 (m, 4H), 1.69~1.48 (m, 4H), 1.41~1.23 (m, 8H), 1.04 (s, 9H).

Step 2: Synthesis of 8-((tert-butyldiphenylsilyl)oxy)octanal

A solution of 8-((tert-butyldiphenylsilyl)oxy)octan-1-ol (35 g, 91 mmol) in DCM (700 mL) was mixed with DMP (116 g, 273 mmol) at 0° C. The mixture was stirred at 15° C. for 3 h. Then the reaction was quenched by the addition of $NaHCO_3$ (1000 mL), filtered and extracted with DCM (1000 mL*2). Then the organic phase was washed with brine (1000 mL), dried over anhydrous $Na_2SO_4$, filtered and concentrated in vacuo. The residue was purified by column chromatography ($SiO_2$, Pet. Ether:EtOAc=20:1) to give 8-((tert-butyldiphenylsilyl)oxy)octanal (28 g, 65.9 mmol).

$^1H$ NMR (400 MHz, CHLOROFORM-d): δ=9.76 (t, J=1.8 Hz, 1H), 7.67 (dd, J=1.8, 7.9 Hz, 4H), 7.50~7.31 (m, 6H), 3.65 (t, J=6.4 Hz, 2H), 2.41 (dt, J=2.0, 7.3 Hz, 2H), 1.69~1.48 (m, 4H), 1.41~1.23 (m, 6H), 1.04 (s, 9H).

Step 3: Synthesis of ethyl (E)-10-((tert-butyldiphenylsilyl)oxy)dec-2-enoate

A solution of ethyl 2-(diethoxyphosphoryl)acetate (12.30 g, 54.9 mmol) in THF (250 mL) was mixed with NaH (1.903 g, 47.6 mmol) at 0° C. under $N_2$ balloon. The reaction mixture was stirred for 40 min at 0° C. Then the solution of 8-((tert-butyldiphenylsilyl)oxy)octanal (14 g, 36.6 mmol) in THF (50 mL) was added to the above mixture at 0° C. The reaction mixture was stirred at 15° C. for 16 h. The resulting mixture was quenched with sat. $NH_4Cl$ (aq. 100 mL), then water (200 mL) was added to the above mixture at 0° C., and the resulting mixture was extracted with EtOAc (2*500 mL). The combined organic extracts were washed with water (800 mL), brine (1000 mL), dried over anhydrous $Na_2SO_4$, and filtered. The filtrate was concentrated in vacuo and the residue was purified by column chromatography ($SiO_2$, Pet. Ether:EtOAc=50:1) to give (E)-ethyl 10-((tert-butyldiphenylsilyl)oxy)dec-2-enoate (14 g, 29.4 mmol).

$^1H$ NMR (500 MHz, CHLOROFORM-d): δ=7.67 (dd, J=1.8, 7.9 Hz, 4H), 7.50~7.31 (m, 6H), 7.15~6.90 (m, 1H), 5.83~5.77 (m, 1H), 4.19 (q, J=7.0 Hz, 2H), 3.65 (t, J=6.5 Hz, 2H), 2.19~2.16 (m, 2H), 1.57~1.24 (m, 13H), 1.05 (s, 9H).

Step 4: Synthesis of ethyl 3-(7-((tert-butyldiphenylsilyl)oxy)heptyl)dodecanoate In a round-bottom flask was added lithium chloride (0.112 g, 2.65 mmol) and copper (I) bromide (0.190 g, 1.325 mmol) and it was heated by blow drier and degassed for 30 min. Then it was cooled to 0° C. and added THF (20 mL) slowly. (E)-ethyl 10-((tert-butyldiphenylsilyl)oxy)dec-2-enoate (2 g, 4.42 mmol), chlorotrimethylsilane (0.576 g, 5.30 mmol) was added to the above reaction mixture at 0° C. and stirred at 0° C. for 30 min. Then the prepared nonylmagnesium bromide (53.0 ml, 26.5 mmol) was added to it at 0° C. slowly and the mixture was stirred at 0° C. for 30 min. Then the reaction mixture was quenched with sat. aq. $NH_4Cl$ (50 mL), diluted with ice water (50 mL), and extracted with EtOAc (50 mL*2). Then the combined organic layers were washed with brine (100 mL*2), dried over anhydrous $Na_2SO_4$, filtered and concentrated in vacuo. The residue was purified by column chromatography ($SiO_2$, Pet. Ether:EtOAc=40:1) to give the title product ethyl 3-(7-((tert-butyldiphenylsilyl)oxy)heptyl)dodecanoate (2 g, 3.27 mmol).

$^1H$ NMR (500 MHz, CHLOROFORM-d): δ=7.67 (d, J=6.6 Hz, 4H), 7.48~7.32 (m, 6H), 4.12 (q, J=7.0 Hz, 2H), 3.64 (t, J=6.5 Hz, 2H), 2.21 (d, J=6.9 Hz, 2H), 1.83 (br s, 1H), 1.55~1.49 (m, 2H), 1.39~1.16 (m, 29H), 1.04 (s, 9H), 0.88 (t, J=6.9 Hz, 3H).

Step 5: Synthesis of 3-(7-((tert-butyldiphenylsilyl)oxy)heptyl)dodecan-1-ol

To a solution of ethyl 3-(7-((tert-butyldiphenylsilyl)oxy)heptyl)dodecanoate (16 g, 27.5 mmol) in THF (160 mL) was slowly added diisobutylaluminum hydride (83 mL, 83 mmol) at 0° C. under $N_2$ balloon. The reaction mixture was stirred at 0° C. for 2 h. Then the mixture was quenched with sat. aq. sodium potassium tartrate tetrahydrate solution (200 ml) and the mixture was stirred for 1 h. Then it was extracted with EtOAc (200 ml×2). The organic layers were washed with brine (200 mL*2) separated and dried over $Na_2SO_4$, filtered and the filtrate was concentrated in vacuo. The residue was purified by column chromatography ($SiO_2$, Pet. Ether:EtOAc=20:1) to give the product 3-(7-((tert-butyldiphenylsilyl)oxy)-heptyl)dodecan-1-ol (12.4 g, 21.86 mmol).

$^1H$ NMR (500 MHz, CHLOROFORM-d): δ=7.67 (d, J=7.6 Hz, 4H), 7.51~7.31 (m, 6H), 3.65 (q, J=6.4 Hz, 4H), 1.55~1.48 (m, 4H), 1.40 (br s, 1H), 1.37~1.14 (m, 27H), 1.04 (s, 9H), 0.88 (t, J=6.9 Hz, 3H).

Step 6: Synthesis of tert-butyl((8-(2-((4-methoxybenzyl)oxy)ethyl)heptadecyl)oxy)-diphenylsilane To a solution of 3-(7-((tert-butyldiphenylsilyl)oxy)heptyl)dodecan-1-ol (11.3 g, 20.97 mmol) in DMF (110 mL) was added tetrabutylammonium iodide (7.74 g, 20.97 mmol). Then NaH (5.03 g, 126 mmol) was added at 0° C. The mixture was stirred at 0° C. for 30 min and 1-(chloromethyl)-4-methoxybenzene (17.06 ml, 126 mmol) was added. The mixture was stirred at 20° C. for 2 h. The reaction mixture was cooled to 0° C., quenched with sat. aq. $NH_4Cl$ (200 mL) at 0° C., diluted with water (100 mL), extracted with EtOAc (100 mL*2). The combined organic layers were washed with brine (200 mL*2), dried over anhydrous $Na_2SO_4$, filtered and the filtrate was concentrated in vacuo. The residue was purified by column chromatography ($SiO_2$, Pet. ether:EtOAc=40:1) to give the product tert-butyl((8-(2-((4-methoxybenzyl)oxy)-ethyl)heptadecyl)-oxy)diphenylsilane (9 g, 10.92 mmol).

$^1H$ NMR (500 MHz, CHLOROFORM-d): δ=7.67 (dd, J=1.5, 7.9 Hz, 4H), 7.45~7.29 (m, 8H), 6.94~6.79 (m, 2H), 4.42 (s, 2H), 3.79 (s, 3H), 3.65 (t, J=6.6 Hz, 2H), 3.45 (t, J=7.0 Hz, 2H), 1.36~1.17 (m, 32H), 1.04 (s, 9H), 0.94~0.77 (m, 3H).

Step 7: Synthesis of 8-(2-((4-methoxybenzyl)oxy)ethyl)heptadecan-1-ol

In a round-bottom flask, to a solution of tert-butyl((8-(2-((4-methoxybenzyl)oxy)ethyl)-heptadecyl)oxy)diphenylsilane (9 g, 13.66 mmol) in THF (10 mL) was added TBAF (41.0 mL, 41.0 mmol) at 15° C. The mixture was stirred at 15° C. for 16 h. Water (100 mL) was added and the reaction mixture was extracted with EtOAc (50 mL*2), the combined organic layers were washed with brine (saturated, 100 mL), dried over anh. $Na_2SO_4$, filtered and concentrated in vacuo. The residue was purified by preparative TLC ($SiO_2$, Pet. Ether:EtOAc=5:1) to give 8-(2-((4-methoxybenzyl)oxy)ethyl)heptadecan-1-ol (2.6 g, 5.87 mmol).

$^1H$ NMR (500 MHz, CHLOROFORM-d): δ=7.45~7.15 (m, 2H), 7.04~6.67 (m, 2H), 4.42 (s, 2H), 3.91~3.75 (m, 3H), 3.63 (t, J=6.6 Hz, 2H), 3.45 (t, J=7.0 Hz, 2H), 1.72~1.48 (m, 4H), 1.41 (br s, 1H), 1.39~1.10 (m, 27H), 0.88 (t, J=6.9 Hz, 3H).

Step 8: Synthesis of 8-(2-((4-methoxybenzyl)oxy)ethyl)heptadecanoic Acid

In a round-bottom flask, to a solution of 8-(2-((4-methoxybenzyl)oxy)ethyl)heptadecan-1-ol (2.6 g, 6.18 mmol) in DMF (26 ml) was added PDC (6.98 g, 18.54 mmol) at 0° C. The mixture was stirred at 20° C. for 12 h.

The reaction mixture was filtered by column chromatography ($SiO_2$, THF (200 ml)) and concentrated in vacuo to provide 8-(2-((4-methoxybenzyl)oxy)ethyl)heptadecanoic acid (2.5 g, 4.60 mmol). The material was moved forward without further purification.

$^1$H NMR (500 MHz, CHLOROFORM-d): δ=7.26~7.18 (m, 2H), 6.87 (d, J=8.5 Hz, 2H), 4.42 (s, 2H), 3.80 (s, 3H), 3.45 (t, J=6.9 Hz, 2H), 2.34 (t, J=7.5 Hz, 2H), 1.58~1.49 (m, 4H), 1.42 (br d, J=11.3 Hz, 2H), 1.35~1.08 (m, 23H), 0.88 (t, J=6.9 Hz, 3H).

Step 9: Synthesis of (Z)-undec-2-en-1-yl 8-(2-((4-methoxybenzyl)oxy)ethyl)heptadecanoate To a solution of 8-(2-((4-methoxybenzyl)oxy)ethyl)heptadecanoic acid (2.5 g, 5.75 mmol) in DCM (25 mL) was slowly (Z)-undec-2-en-1-ol (1.469 g, 8.63 mmol), DMAP (0.703 g, 5.75 mmol), DIEA (4.02 mL, 23.01 mmol) and EDC (2.205 g, 11.50 mmol) at 0° C. Then the mixture was stirred at 20° C. for 16 h. The resulting mixture was diluted with water (10 mL) and extracted with DCM (2*10 mL). The combined organic extracts were washed with brine (20 mL*2), and the organic layers were dried over anh. $Na_2SO_4$ and filtered. The filtrate was concentrated in vacuo and the residue was purified by column chromatography ($SiO_2$, Pet. ether:EtOAc=20:1) to give (Z)-undec-2-en-1-yl 8-(2-((4-methoxybenzyl)oxy)ethyl)heptadecanoate (2 g, 3.41 mmol).

$^1$H NMR (400 MHz, CHLOROFORM-d): δ=7.34~7.19 (m, 2H), 6.86 (d, J=8.6 Hz, 2H), 5.75~5.41 (m, 2H), 4.61 (d, J=6.8 Hz, 2H), 4.41 (s, 2H), 3.79 (s, 3H), 3.43 (t, J=7.0 Hz, 2H), 2.29 (t, J=7.6 Hz, 2H), 2.08 (q, J=7.2 Hz, 2H), 1.67~1.49 (m, 4H), 1.44~1.12 (m, 35H), 0.87 (br t, J=6.7 Hz, 6H).

Step 10: Synthesis of (Z)-undec-2-en-1-yl 8-(2-hydroxyethyl)heptadecanoate

To a solution of (Z)-undec-2-en-1-yl 8-(2-((4-methoxybenzyl)oxy)ethyl)heptadecanoate (2 g, 3.41 mmol) in ACN (20 mL) and water (5 mL) was slowly added CAN (7.47 g, 13.63 mmol) at 0° C., then the mixture was warmed up 25° C. and stirred for 2 h. The reaction mixture was quenched with sat. aq. $Na_2SO_3$ (10 mL), extracted with EtOAc (10 mL*2), the combined organic layers were washed with brine (saturated, 20 mL*2) dried over anhydrous $Na_2SO_4$ filtered and concentrated in vacuo. The residue was purified by column chromatography ($SiO_2$, Pet. ether:EtOAc=100:7.6) to give (Z)-undec-2-en-1-yl 8-(2-hydroxyethyl)heptadecanoate (2.1 g, 2.70 mmol).

$^1$H NMR (500 MHz, CHLOROFORM-d): δ=5.72~5.59 (m, 1H), 5.57~5.46 (m, 1H), 4.62 (d, J=6.9 Hz, 2H), 3.66 (t, J=7.0 Hz, 2H), 2.30 (t, J=7.5 Hz, 2H), 2.09 (q, J=7.4 Hz, 2H), 1.62 (td, J=7.5, 14.6 Hz, 4H), 1.51 (q, J=6.9 Hz, 2H), 1.45~1.18 (m, 36H), 0.92~0.83 (m, 6H).

Step 11: Synthesis of (Z)-undec-2-en-1-yl 8-(2-oxoethyl)heptadecanoate

To a solution of (Z)-undec-2-en-1-yl 8-(2-hydroxyethyl)heptadecanoate (1.2 g, 2.57 mmol) in DCM (24 mL) was added DMP (3.27 g, 7.71 mmol) at 0° C. The mixture was stirred at 25° C. for 3 h. The reaction mixture was diluted with ice water (50 mL) and quenched with saturated $NaHCO_3$ (20 mL). The resulting mixture was filtered, and the filtrate was extracted with DCM (50 mL*2). The combined organic layers washed with brine (40 mL*2), dried over anhydrous $Na_2SO_4$, filtered and concentrated. The residue was purified with reaction 1007182-071 by column chromatography ($SiO_2$, Pet. ether:EtOAc=20:1) to give (Z)-undec-2-en-1-yl 8-(2-oxoethyl)heptadecanoate (0.8 g, 1.377 mmol).

$^1$H NMR (500 MHz, CHLOROFORM-d): δ=9.75 (t, J=2.4 Hz, 1H), 5.73~5.59 (m, 1H), 5.58~5.47 (m, 1H), 4.62 (d, J=6.9 Hz, 2H), 2.37~2.25 (m, 4H), 2.09 (q, J=7.2 Hz, 2H), 1.93 (br s, 1H), 1.66~1.58 (m, 3H), 1.40~1.17 (m, 35H), 0.92~0.80 (m, 6H).

Step 12: Synthesis of (Z)-undec-2-en-1-yl 8-(2-(dimethylamino)ethyl)heptadecanoate To a solution of (Z)-undec-2-en-1-yl 8-(2-oxoethyl)heptadecanoate (1.9 g, 3.27 mmol) in DCE (19 mL) was added dimethylamine hydrochloride (0.800 g, 9.81 mmol), sodium triacetoxyhydroborate (2.079 g, 9.81 mmol) at 0° C. Then the mixture was warmed up to 20° C. and further stirred for 16 hours. LCMS showed the reaction was completed. The reaction mixture was diluted by ice-water (40 mL), the resulting mixture was extracted with DCM (30 mL*2), combined organic layers, washed with brine (50 mL*2), organic layers was dried over anhydrous $Na_2SO_4$ filtered and the filtrate was concentrated in vacuum. The reside was purified by preparative HPLC (Column YMC-Actus Pro C18, Condition 35% to 5% water (0.1% TFA)-ACN) to provide Lipid 2, having a structure as set forth below:

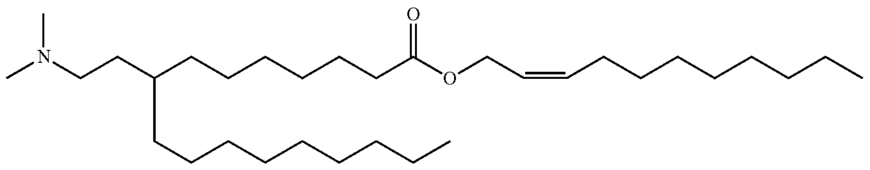 [SMILES: CCCCCCCC/C=C\COC(=O)CCCCCCC(CCCCCCCCC)CCN(C)C]

Lipid 2, i.e. (Z)-undec-2-en-1-yl 8-(2-(dimethylamino)ethyl)heptadecanoate (1187.35 mg, 2.404 mmol).

$^1$H NMR (500 MHz, CHLOROFORM-d): δ=11.74 (br s, 1H), 5.66~5.57 (m, 1H), 5.50 (td, J=6.8, 10.8 Hz, 1H), 4.60 (br d, J=6.7 Hz, 2H), 3.06~2.92 (m, 2H), 2.82 (br s, 6H), 2.28 (t, J=7.5 Hz, 2H), 2.07 (q, J=7.3 Hz, 2H), 1.70~1.54 (m, 4H), 1.39~1.15 (m, 37H), 0.86 (br t, J=6.7 Hz, 6H). MS (ESI) m/z: 494.5 $[M+H]^+$.

Example 3: Synthesis of Lipid 3, (Z)-non-2-en-1-yl 10-(2-(dimethylamino)ethyl)nonadecanoate
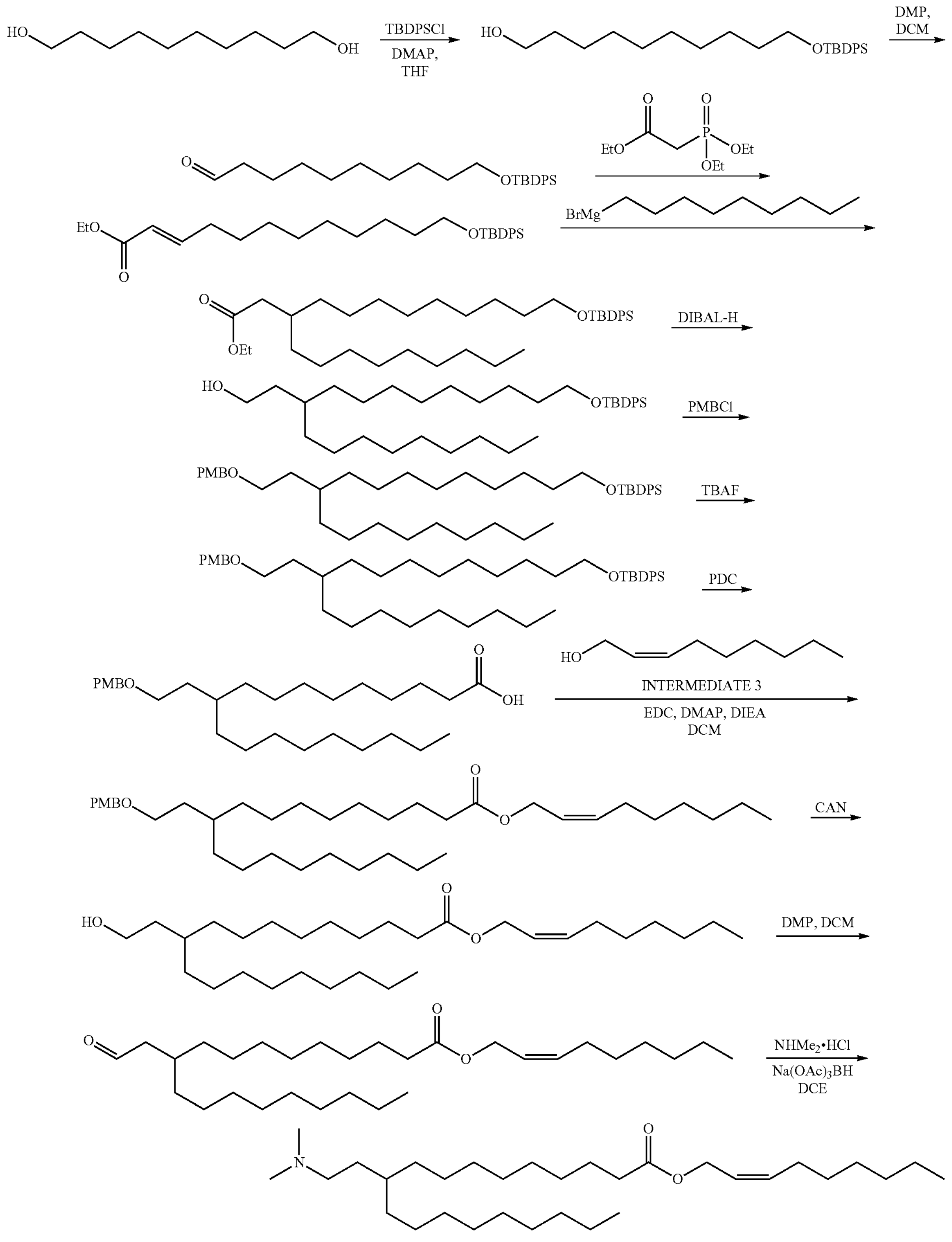
Lipid 3

Step 1: Synthesis of 10-((tert-butyldiphenylsilyl)oxy)decan-1-ol

To a solution of decane-1, 10-diol (25 g, 143 mmol) in THF (100 mL) was added imidazole (19.53 g, 287 mmol), DMAP (1.752 g, 14.34 mmol). Then TBDPSCl (36.5 ml, 142 mmol) was added to the above mixture at 0° C. and the reaction was heated to 25° C. and stirred for 16 h. The reaction was cooled to room temperature and water (100 mL) was added to it. Then it was extracted with EtOAc (100 mL*2), combined organic layers, washed with brine (100 mL*2), dried over anhydrous $Na_2SO_4$, filtered and concentrated in vacuo. The residue was purified by column chromatography ($SiO_2$, Pet. ether:EtOAc=20:1 to 5:1) to give 10-((tert-butyldiphenylsilyl)-oxy)decan-1-ol (30 g, 69.1 mmol).

$^1$H NMR (500 MHz, CHLOROFORM-d): δ=7.77~7.62 (m, 4H), 7.57~7.36 (m, 6H), 3.73~3.61 (m, 4H), 1.56 (qd, J=6.7, 13.7 Hz, 4H), 1.39~1.25 (m, 12H), 1.04 (s, 9H).

Step 2: Synthesis of 10-((tert-butyldiphenylsilyl)oxy)decanal

To a solution of 10-((tert-butyldiphenylsilyl)oxy)decan-1-ol (30 g, 72.7 mmol) in DCM (450 mL) was added DMP (77 g, 182 mmol) at 0° C. The mixture was stirred at 25° C. for 3 h. Then resulting mixture was quenched with $NaHCO_3$ (500 ml) at 0° C. Then the reaction mixture was filtered, and the filtrate was extracted with DCM (500 mL*2), combined organic layers, washed with brine (1000 mL), organic layer was separated and dried over anhydrous $Na_2SO_4$, filtered and concentrated in vacuo. The residue was purified by column chromatography ($SiO_2$, Pet. ether:EtOAc=20:1) to give the product 10-((tert-butyldiphenylsilyl)oxy)decanal (20 g, 46.3 mmol).

$^1$H NMR (500 MHz, CHLOROFORM-d): δ=9.76 (s, 1H), 7.67 (d, J=6.9 Hz, 4H), 7.45~7.34 (m, 6H), 3.65 (t, J=6.5 Hz, 2H), 2.42 (dt, J=1.4, 7.4 Hz, 2H), 1.67~1.55 (m, 4H), 1.38~1.21 (m, 10H), 1.05 (s, 9H).

Step 3: Synthesis of ethyl (E)-12-((tert-butyldiphenylsilyl)oxy)dodec-2-enoate

To a solution of ethyl 2-(diethoxyphosphoryl) acetate (15.29 g, 68.2 mmol) in THF (200 mL) was slowly added NaH (2.53 g, 63.3 mmol) at 0° C. under $N_2$ balloon. The reaction mixture was stirred at 0° C. for 40 min. Then 10-((tert-butyldiphenylsilyl)oxy)decanal (20 g, 48.7 mmol) was added to the above mixture at 0° C. The reaction mixture was stirred at 15° C. for 16 h. The resulting mixture was quenched with sat. aq. $NH_4Cl$ (300 mL), then water (200 mL) was added to the above mixture at 0° C. Then the resulting mixture was extracted with EtOAc (500 mL*2). The combined organic extracts were washed with brine (1000 mL), dried over anhydrous $Na_2SO_4$, and filtered. The filtrate was concentrated in vacuo and the residue was purified by column chromatography ($SiO_2$, Pet. ether:EtOAc 40:1) to give (E)-ethyl 12-((tert-butyldiphenylsilyl)oxy)dodec-2-enoate (15.5 g, 32.2 mmol).

$^1$H NMR (400 MHz, CHLOROFORM-d): δ=7.67 (dd, J=1.3, 7.9 Hz, 4H), 7.45~7.32 (m, 6H), 7.05~6.88 (m, 1H), 5.81 (d, J=15.8 Hz, 1H), 4.18 (q, J=7.0 Hz, 2H), 3.65 (t, J=6.4 Hz, 2H), 2.18 (q, J=6.7 Hz, 2H), 1.56~1.50 (m, 2H), 1.50~1.39 (m, 2H), 1.38~1.18 (m, 9H), 1.04 (s, 9H).

Step 4: Synthesis of ethyl 12-((tert-butyldiphenylsilyl)oxy)-3-nonyldodecanoate

To a round-bottom flask was added copper(I) bromide (1.074 g, 7.49 mmol) and LiCl (0.65 g, 15 mmol). Then THF (120 mL) was added. (E)-ethyl 12-((tert-butyldiphenylsilyl)oxy)dodec-2-enoate (12 g, 24.96 mmol) and chlorotrimethylsilane (3.83 mL, 30.0 mmol) were added to the above reaction mixture at 0° C. and stirred at 0° C. for 30 min. Then the freshly prepared nonylmagnesium bromide (300 mL, 150 mmol) was added to it at 0° C. slowly, and the mixture was stirred at 0° C. for 30 min. The reaction mixture was quenched with sat. aq. $NH_4Cl$ (500 mL), diluted with ice water (100 mL), extracted with EtOAc (500 mL*2). Then combined organic layers was washed with brine (500 mL*2), dried over anhydrous $Na_2SO_4$, filtered and concentrated in vacuo. The residue was purified by column chromatography ($SiO_2$, Pet. ether:EtOAc=20:1) to give the title product ethyl 12-((tert-butyldiphenylsilyl)oxy)-3-nonyldodecanoate (14 g, 21.84 mmol).

$^1$H NMR (500 MHz, CHLOROFORM-d): δ=7.71~7.63 (m, 4H), 7.44~7.34 (m, 6H), 4.12 (q, J=7.1 Hz, 2H), 3.65 (t, J=6.6 Hz, 2H), 2.22 (d, J=6.9 Hz, 2H), 1.84 (br s, 1H), 1.56~1.50 (m, 2H), 1.33~1.19 (m, 33H), 1.04 (s, 9H), 0.88 (t, J=6.9 Hz, 3H).

Step 5: Synthesis of 12-((tert-butyldiphenylsilyl)oxy)-3-nonyldodecan-1-ol

To a solution of ethyl 12-((tert-butyldiphenylsilyl)oxy)-3-nonyldodecanoate (34 g, 55.8 mmol) in THF (340 mL) was slowly added DIBAL-H (167 mL, 167 mmol) at 0° C. under $N_2$ balloon. The reaction mixture was stirred at 0° C. for 2 h. Then the mixture was quenched with sat. sodium potassium tartrate tetrahydrate solution (100 mL) and the mixture was stirred for 1 h. Then it was extracted with EtOAc (200 mL*2). The organic phase was washed with brine (200 mL*2) separated and dried over $Na_2SO_4$, filtered and the filtrate was concentrated. The residue was purified by column chromatography ($SiO_2$, Pet. ether:EtOAc=10:1) to give the product 12-((tert-butyldiphenylsilyl)oxy)-3-nonyldodecan-1-ol (22 g, 38.8 mmol).

$^1$H NMR (400 MHz, CHLOROFORM-d): δ=7.64~7.74 (m, 4H), 7.34~7.48 (m, 6H), 3.67 (q, J=6.4 Hz, 4H), 1.49~1.63 (m, 2H), 1.21~1.45 (m, 34H), 1.04 (s, 9H), 0.89 (t, J=6.7 Hz, 3H).

Step 6: Synthesis of tert-butyl((10-(2-((4-methoxybenzyl)oxy)ethyl)nonadecyl)oxy)-diphenylsilane To a solution of 12-((tert-butyldiphenylsilyl)oxy)-3-nonyldodecan-1-ol (15 g, 26.5 mmol) in DMF (150 mL) was added tetrabutylammonium iodide (9.77 g, 26.5 mmol) and NaH (6.35 g, 159 mmol) was added at 0° C. The mixture was stirred at 0° C. for 30 mins, then 1-(chloromethyl)-4-methoxybenzene (24.86 g, 159 mmol) was added to the above mixture. The mixture was stirred at 20° C. for 2 h. Then the mixture was cooled to 0° C., quenched with sat. aq., $NH_4Cl$ (200 mL), then diluted with water (100 mL), extracted with EtOAc (100 mL*2), organic layers were combined, washed with brine (200 mL*2), organic layer was dried over $Na_2SO_4$, filtered and the filtrate was concentrated in in vacuo. The resulting residue was purified by column chromatography ($SiO_2$, Pet. ether:EtOAc=40:1) to give the product tert-butyl((10-(2-((4-methoxybenzyl)oxy)ethyl)nonadecyl)-oxy)diphenylsilane (10 g, 14.55 mmol).

$^1$H NMR (500 MHz, CHLOROFORM-d): δ=7.66 (d, J=6.6 Hz, 4H), 7.45~7.34 (m, 6H), 7.25 (t, J=4.2 Hz, 2H), 6.87 (d, J=8.5 Hz, 2H), 4.42 (s, 2H), 3.79 (s, 3H), 3.64 (t, J=6.5 Hz, 2H), 3.45 (t, J=7.0 Hz, 2H), 1.56~1.50 (m, 2H), 1.28~1.20 (m, 33H), 1.04 (s, 9H), 0.87 (t, J=6.9 Hz, 3H).

Step 7: Synthesis of 10-(2-((4-methoxybenzyl)oxy)ethyl)nonadecan-1-ol

To a solution of tert-butyl((10-(2-((4-methoxybenzyl)oxy)ethyl)nonadecyl)oxy)diphenylsilane (6 g, 8.73 mmol) in THF (30 mL) was added TBAF (30 mL, 30.0 mmol) at 30° C., and the mixture was stirred at 30° C. for 12 hr. The resulting mixture was diluted with water (100 mL), extracted with EtOAc (200 mL*2), combined organic layer, washed with brine (500 mL), organic layer was dried over $Na_2SO_4$, filtered and the filtrate was concentrated in vacuo, the residue was purified by column chromatography ($SiO_2$, Pet. ether:EtOAc=5:1), to give the title product 10-(2-((4-methoxybenzyl)oxy)ethyl)nonadecan-1-ol (3 g, 6.35 mmol).

$^1$H NMR (500 MHz, CHLOROFORM-d): δ=7.29~7.25 (m, 2H), 6.95~6.76 (m, 2H), 4.42 (s, 2H), 3.79 (s, 3H), 3.64 (t, J=6.5 Hz, 2H), 3.45 (t, J=7.0 Hz, 2H), 1.56~1.50 (m, 2H), 1.28~1.20 (m, 32H), 0.87 (t, J=6.9 Hz, 3H).

Step 8: Synthesis of 10-(2-((4-methoxybenzyl)oxy)ethyl)nonadecanoic Acid

To a solution of 10-(2-((4-methoxybenzyl)oxy)ethyl)nonadecan-1-ol (5 g, 11.14 mmol) in DMF (60 mL) was added PDC (20.96 g, 55.7 mmol) at 0° C., then warmed up to 30° C. and stirred for 12 h. The reaction mixture was diluted with EtOAc (100 mL), filtered by column chromatography ($SiO_2$, EtOAc and THF) to give the product 10-(2-((4-methoxybenzyl)oxy)ethyl)nonadecanoic acid (5 g, 10.27 mmol).

$^1$H NMR (500 MHz, CHLOROFORM-d): δ=7.29~7.25 (m, 2H), 6.89~6.76 (m, 2H), 4.42 (s, 2H), 3.79 (s, 3H), 3.45 (t, J=6.4 Hz, 2H), 2.35 (t, J=7.6 Hz, 2H), 1.71~1.50 (m, 2H), 1.28~1.20 (m, 32H), 0.90~0.86 (m, 3H).

Step 9: Synthesis of (Z)-non-2-en-1-yl 10-(2-((4-methoxybenzyl)oxy)ethyl)nonadecanoate To a solution of 10-(2-((4-methoxybenzyl)oxy)ethyl)nonadecanoic acid (11 g, 23.77 mmol) in DCM (110 mL) was slowly (Z)-non-2-en-1-ol (5.18 g, 35.7 mmol), DMAP (2.90 g, 23.77 mmol), DIEA (16.61 mL, 95 mmol) and EDC (9.11 g, 47.5 mmol) at 0° C. Then the mixture was stirred at 20° C. for 16 h. The resulting mixture was diluted with water (100 mL) and extracted with DCM (2*100 mL). The combined organic extracts were washed with brine (00 mL*2), and the organic layers were dried over anhydrous $Na_2SO_4$ and filtered. The filtrate was concentrated in vacuo and the residue was purified by column chromatography ($SiO_2$, Pet. ether:EtOAc=20:1) to give (Z)-non-2-en-1-yl 10-(2-((4-methoxybenzyl)oxy)ethyl)nonadecanoate (8.3 g, 13.43 mmol).

$^1$H NMR (500 MHz, CHLOROFORM-d): δ=7.35~7.16 (m, 2H), 6.95~6.76 (m, 2H), 5.78~5.59 (m, 1H), 5.55~5.43 (m, 1H), 4.62 (d, J=6.9 Hz, 2H), 4.47~4.38 (m, 2H), 3.80 (s, 3H), 3.45 (t, J=7.0 Hz, 2H), 2.30 (t, J=7.6 Hz, 2H), 2.09 (q, J=7.0 Hz, 2H), 2.04 (m, 1H), 1.58~1.48 (m, 2H), 1.32~1.14 (m, 38H), 0.88 (t, J=6.9 Hz, 6H).

Step 10: Synthesis of (Z)-non-2-en-1-yl 10-(2-hydroxyethyl)nonadecanoate

To a solution of (Z)-non-2-en-1-yl 10-(2-((4-methoxybenzyl)oxy)ethyl)nonadecanoate (7 g, 11.93 mmol) in ACN (70 mL) and water (17.5 mL) was slowly added CAN (26.2 g, 47.7 mmol) at 0° C. Then the mixture was warmed up 25° C. and stirred for 2 h. The resulting mixture was diluted with water (100 mL) and extracted with DCM (100 mL*2). The combined organic extracts were washed with brine (100 mL*2), and the organic layers were dried over anh. $Na_2SO_4$ and filtered. The filtrate was concentrated in vacuo and the residue was purified by column chromatography ($SiO_2$, Pet. ether:EtOAc=10:1) to give (Z)-non-2-en-1-yl 10-(2-hydroxyethyl)nonadecanoate (4.4 g, 8.95 mmol).

$^1$H NMR (400 MHz, CHLOROFORM-d): δ=5.76~5.39 (m, 2H), 4.62 (d, J=6.6 Hz, 2H), 3.66 (t, J=7.0 Hz, 2H), 2.30 (t, J=7.6 Hz, 2H), 2.09 (q, J=6.9 Hz, 2H), 1.57~1.47 (m, 2H), 1.37~1.19 (m, 40H), 0.92~0.79 (m, 6H).

Step 11: Synthesis of (Z)-non-2-en-1-yl 10-(2-oxoethyl)nonadecanoate

To a solution of (Z)-non-2-en-1-yl 10-(2-hydroxyethyl)nonadecanoate (2 g, 4.28 mmol) in DCM (20 mL) was added DMP (5.45 g, 12.85 mmol) at 0° C. The mixture was stirred at 25° C. for 3 h.

The reaction mixture was diluted with ice-water (500 ml), quenched with sat. $NaHCO_3$ to adjust pH to 7, the resulting mixture was filtered and the filtrate was extracted with DCM (20 mL*2), combined organic layers, washed with brine (40 mL*2), organic layers was concentrated in vacuum, the residue was purified by column chromatography ($SiO_2$, Pet. ether:EtOAc=40:1 to 20:1) to give (Z)-non-2-en-1-yl 10-(2-hydroxyethyl)nonadecanoate (1.3 g, 2.79 mmol).

$^1$H NMR (500 MHz, CHLOROFORM-d): δ=9.75 (t, J=2.4 Hz, 1H), 5.71~5.45 (m, 2H), 4.62 (d, J=6.9 Hz, 2H), 2.38~2.21 (m, 4H), 2.09 (q, J=7.0 Hz, 2H), 1.93 (br s, 1H), 1.67~1.59 (m, 2H), 1.43~1.14 (m, 36H), 0.88 (t, J=6.9 Hz, 6H).

Step 12: (Z)-non-2-en-1-yl 10-(2-(dimethylamino)ethyl)nonadecanoate

To a solution of (Z)-non-2-en-1-yl 10-(2-oxoethyl)nonadecanoate (2.6 g, 5.59 mmol) in DCE (40 mL) was added dimethylamine hydrochloride (1.369 g, 16.78 mmol), sodium triacetoxyhydroborate (3.56 g, 16.78 mmol) at 0° C. Then the mixture was warmed up to 30° C. and further stirred for 12 h. The reaction mixture was diluted by ice water (20 mL), the resulting mixture was extracted with DCM (30 mL*2), combined organic layers, washed with brine (50 mL*2), organic layers was dried over $Na_2SO_4$, filtered and the filtrate was concentrated in vacuo, the reside was purified by preparative HPLC (Column YMC-Actus Pro C18; Condition 30% to 10% water (0.1% TFA)-ACN) to form a brown liquid, which is the monoester cationic lipid of Lipid 3, having a structure as set forth below:

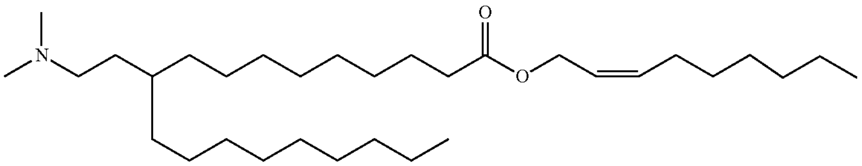 [SMILES: CCCCCC/C=C\COC(=O)CCCCCCCCC(CCCCCCCCC)CCN(C)C]
Lipid 3,
i.e. (Z)-non-2-en-1-yl 10-(2-(dimethylamino)ethyl)-nonadecanoate (1154.14 mg, 2.313 mmol).
$^1$H NMR (500 MHz, CHLOROFORM-d): δ=5.64 (td, J=7.6, 10.8 Hz, 1H), 5.57~5.39 (m, 1H), 4.61 (d, J=6.9 Hz, 2H), 3.07~2.95 (m, 2H), 2.82 (d, J=4.6 Hz, 6H), 2.30 (t, J=7.6 Hz, 2H), 2.09 (q, J=7.5 Hz, 2H), 1.70~1.57 (m, 4H), 1.41~1.31 (m, 4H), 1.30~1.21 (m, 33H), 0.88 (t, J=6.9 Hz, 6H). MS (ESI) m/z: 494.5 [M+H]+.
Example 4: Synthesis of Lipid 4, (Z)-tridec-2-en-1-yl 6-(2-(dimethylamino)ethyl)pentadecanoate
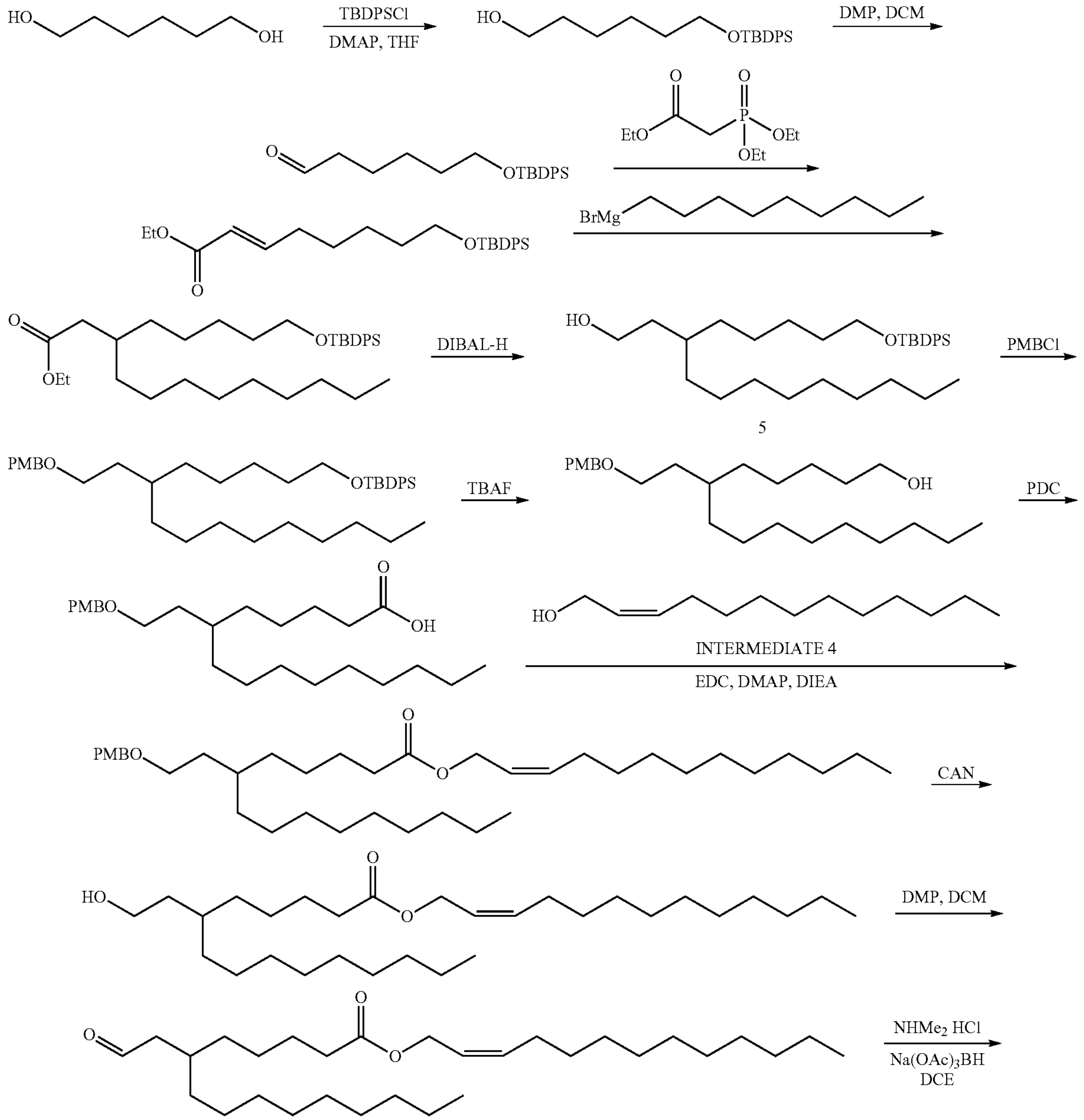

-continued

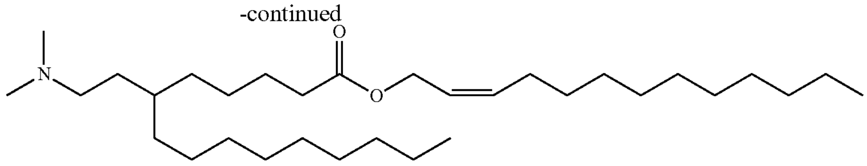

Lipid 4

Step 1: Synthesis of 6-((tert-butyldiphenylsilyl)oxy)hexan-1-ol

To a solution of hexane-1,6-diol (45 g, 381 mmol) in THF (500 mL) was added imidazole (51.8 g, 762 mmol), DMAP (4.65 g, 38.1 mmol). Then TBDPSCl (93 mL, 362 mmol) was added to the above mixture at 0° C. and the reaction was heated to 25° C. and stirred for 16 h under $N_2$ balloon. The progress of the reaction was monitored by TLC. The reaction was cooled to room temperature and water (500 mL) was added to it. Then it was extracted with EtOAc (500 mL*2), combined organic layers, washed with brine (500 mL), dried over anhydrous $Na_2SO_4$, filtered and concentrated. The residue was purified by column chromatography ($SiO_2$, Pet. ether:EtOAc=20:1 to 5:1) to give 6-((tert-butyldiphenylsilyl)oxy)hexan-1-ol (45 g, 101 mmol).

$^1$H NMR (400 MHz, CHLOROFORM-d): δ=7.68 (dd, J=7.6, 1.6 Hz, 4H), 7.36~7.46 (m, 6H), 3.65 (dt, J=19.6, 6.4 Hz, 4H), 1.51~1.64 (m, 4H), 1.32~1.42 (m, 4H), 1.06 (s, 9H).

Step 2: Synthesis of 6-((tert-butyldiphenylsilyl)oxy)hexanal

To a solution of 6-((tert-butyldiphenylsilyl)oxy)hexan-1-ol (45 g, 126 mmol) in DCM (500 mL) was added DMP (161 g, 379 mmol) at 0° C. The mixture was stirred at 25° C. for 4 h under $N_2$ balloon. The resulting mixture was diluted with ice-water (500 mL) and quenched with $NaHCO_3$ (sat.) to adjust pH to 7. The resulting mixture was filtered and the filtrate was extracted with DCM (1 L*2). The combined organic extracts were washed with brine (1 L), dried over anhydrous $Na_2SO_4$, and filtered. The filtrated was concentrated in vacuo, and the residue was purified by column chromatography ($SiO_2$, Pet. ether:EtOAc=99:1 to 20:1) to give 6-((tert-butyldiphenylsilyl)oxy)hexanal (31 g, 69.9 mmol).

$^1$H NMR (400 MHz, CHLOROFORM-d): δ=9.75 (d, J=1.6 Hz, 1H), 7.67 (d, J=7.6 Hz, 4H), 7.35~7.47 (m, 6H), 3.67 (t, J=6.4 Hz, 2H), 2.41 (t, J=7.2 Hz, 2H), 1.60 (tt, J=14.4, 7.2 Hz, 4H), 1.35~1.47 (m, 2H), 1.06 (s, 9H).

Step 3: Synthesis of (E)-ethyl 8-((tert-butyldiphenylsilyl)oxy)oct-2-enoate

To a solution of ethyl 2-(diethoxyphosphoryl)acetate (27.4 g, 122 mmol) in THF (500 mL) was slowly added NaH (4.55 g, 114 mmol) at 0° C. under $N_2$ balloon. The reaction mixture was stirred for 40 min at 0° C. Then the solution of 6-((tert-butyldiphenylsilyl)oxy)hexanal (31 g, 87 mmol) in THF (100 mL) was added to the above mixture at 0° C. The reaction mixture was stirred at 25° C. for 16 h. The resulting mixture was quenched with sat. aq. $NH_4Cl$ (300 mL). Then water (200 mL) was added to the above mixture at 0° C., and the resulting mixture was extracted with EtOAc (500 mL*2). The combined organic extracts were washed with water (800 mL), brine (1000 mL), dried over anhydrous $Na_2SO_4$, and filtered. The filtrate was concentrated in vacuo and the residue was purified by column chromatography ($SiO_2$, Pet. ether:EtOAc=50:1 to 20:1) to give (E)-ethyl 8-((tert-butyldiphenylsilyl)oxy)oct-2-enoate (27 g, 52.1 mmol).

$^1$H NMR (500 MHz, CHLOROFORM-d): δ=7.62~7.70 (m, 4H), 7.34~7.45 (m, 6H), 6.90~7.00 (m, 1H), 5.80 (d, J=16.0 Hz, 1H), 4.15~4.23 (m, 2H), 3.65 (t, J=6.5 Hz, 2H), 2.17 (q, J=7.0 Hz, 2H), 1.52~1.59 (m, 2H), 1.36~1.45 (m, 4H), 1.29 (t, J=7.0 Hz, 3H), 1.05 (s, 9H).

Step 4: Synthesis of ethyl 3-(5-((tert-butyldiphenylsilyl)oxy)pentyl)dodecanoate A solution of copper(I) bromide (2.230 g, 15.54 mmol) and lithium chloride (1.318 g, 31.1 mmol) [dried under high heated gun and cooled to room temperature] in THF (220 mL) was prepared and stirred for 10 min. Next, (E)-ethyl 8-((tert-butyldiphenylsilyl)oxy)oct-2-enoate (22 g, 51.8 mmol) and TMSCl (7.95 mL, 62.2 mmol) were slowly added to the above mixture at 0° C. under $N_2$, and the mixture was stirred for 30 min. Then fresh prepared nonylmagnesium bromide (71.9 g, 311 mmol) was added to the above mixture, and the mixture was stirred for 2 h at 0° C. The resulting mixture was quenched with sat. aq. $NH_4Cl$ (300 mL), and water (40 mL) was added to the above mixture. Then it was extracted with EtOAc (300 mL*2). The combined organic extracts were washed with brine (360 mL), dried over anhydrous $Na_2SO_4$, and filtered. The filtrate was concentrated in vacuo, and the residue was purified by column chromatography ($SiO_2$, Pet. ether:EtOAc=99:1 to 20:1) to give the product ethyl 3-(5-((tert-butyldiphenylsilyl)-oxy)-pentyl)dodecanoate (24 g, 34.7 mmol).

$^1$H NMR (400 MHz, CHLOROFORM-d): δ=7.67 (dd, J=8.0, 1.6 Hz, 4H), 7.34~7.45 (m, 6H), 4.12 (q, J=7.2 Hz, 2H), 3.65 (t, J=6.4 Hz, 2H), 2.21 (d, J=7.2 Hz, 2H), 1.54~1.60 (m, 2H), 1.21~1.38 (m, 26H), 1.05 (s, 9H), 0.88 (t, J=6.8 Hz, 3H).

Step 5: Synthesis of 3-(5-((tert-butyldiphenylsilyl)oxy)pentyl)dodecan-1-ol

To a solution of ethyl 3-(5-((tert-butyldiphenylsilyl)oxy)pentyl)dodecanoate (29 g, 52.5 mmol) in THF (290 mL) was slowly added DIBAL-H (157 mL, 157 mmol) at 0° C. under $N_2$ balloon, and the mixture was stirred for 2 h at 0° C. Then the mixture was quenched with sat. aq. sodium potassium tartrate tetrahydrate solution (200 mL), and the mixture was stirred for 1 h. Then it was extracted with EtOAc (200 mL*2). The combined organic extracts were washed with brine (260 mL), dried over anh. $Na_2SO_4$, and filtered. The filtrate was concentrated in vacuo, and the residue was purified by column chromatography ($SiO_2$, Pet. ether:EtOAc=10:1) to give the product 3-(5-((tert-butyldiphenylsilyl)oxy)pentyl)dodecan-1-ol (21 g, 32.9 mmol).

$^1$H NMR (400 MHz, CHLOROFORM-d): δ=7.67 (dd, J=7.6, 1.2 Hz, 4H), 7.34~7.46 (m, 6H), 3.65 (t, J=6.8 Hz, 4H), 1.48~1.59 (m, 4H), 1.23~1.41 (m, 23H), 1.05 (s, 9H), 0.88 (t, J=6.8 Hz, 3H).

Step 6: Synthesis of tert-butyl((6-(2-((4-methoxybenzyl)oxy)ethyl)pentadecyl)oxy)-diphenylsilane To a solution of 3-(5-((tert-butyldiphenylsilyl)oxy)pentyl) dodecan-1-ol (7.5 g, 14.68 mmol) in DMF (50 mL) was added TBAI (5.42 g, 14.68 mmol) and NaH (3.52 g, 88 mmol) at 0° C. under $N_2$ balloon, and the mixture was stirred at 0° C. for 30 min. Then 4-methoxybenzyl chloride (12.00 mL, 88 mmol) was added to the above mixture, and the mixture was stirred at 25° C. for 2 h. Then the mixture was quenched with sat. aq. $NH_4Cl$ solution (160 mL) at 0° C., and the resulting mixture was extracted with EtOAc (200 mL*2). The combined organic extracts were washed with brine (260 mL*2), dried over anhydrous $Na_2SO_4$, and filtered. The filtrate was concentrated in vacuo and the residue was purified by column chromatography ($SiO_2$, Pet. ether: EtOAc=100:1.25) to give the product tert-butyl((6-(2-((4-methoxybenzyl)oxy)ethyl)-pentadecyl)oxy)diphenylsilane (5.5 g, 6.97 mmol).

$^1$H NMR (400 MHz, CHLOROFORM-d): δ=7.66 (dd, J=7.6, 1.6 Hz, 4H), 7.34~7.43 (m, 6H), 7.23~7.26 (m, 2H), 6.86 (d, J=8.8 Hz, 2H), 4.41 (s, 2H), 3.78 (s, 3H), 3.64 (t, J=6.4 Hz, 2H), 3.44 (t, J=7.2 Hz, 2H), 1.52~1.58 (m, 4H), 1.19~1.34 (m, 23H), 1.04 (s, 9H), 0.87 (t, J=6.8 Hz, 3H).

Step 7: Synthesis of 6-(2-((4-methoxybenzyl)oxy) ethyl)pentadecan-1-ol

To a solution of tert-butyl((6-(2-((4-methoxybenzyl)oxy) ethyl)pentadecyl)oxy)diphenylsilane (5 g, 7.92 mmol) in THF (50 mL) was added TBAF (39.6 mL, 39.6 mmol) at 0° C., and the mixture was stirred for 12 h at 25° C. The resulting mixture was quenched with $H_2O$ (200 mL) at 0° C., and the resulting mixture was extracted with EtOAc (200 mL*2). The combined organic extracts were washed with brine (200 mL), dried over anhydrous $Na_2SO_4$, and filtered. The filtrate was concentrated in vacuo and the residue was purified by column chromatography ($SiO_2$, Pet. ether:EtOAc=20:1 to 10:1) to give the product 6-(2-((4-methoxybenzyl)oxy)ethyl)pentadecan-1-ol (2.3 g, 4.69 mmol).

$^1$H NMR (400 MHz, CHLOROFORM-d): δ=7.24~7.28 (m, 2H), 6.87 (d, J=8.8 Hz, 2H), 4.42 (s, 2H), 3.80~3.81 (m, 1H), 3.80 (s, 1H), 3.79~3.81 (m, 1H), 3.62 (t, J=6.8 Hz, 2H), 3.45 (t, J=7.2 Hz, 2H), 1.50~1.58 (m, 4H), 1.21~1.44 (m, 24H), 0.88 (t, J=6.8 Hz, 3H).

Step 8: Synthesis of 6-(2-((4-methoxybenzyl)oxy)ethyl)pentadecanoic Acid

To a solution of 6-(2-((4-methoxybenzyl)oxy)ethyl)pentadecan-1-ol (6.6 g, 16.81 mmol) in DMF (70 mL) was slowly added PDC (31.6 g, 84 mmol) at 0° C. The reaction mixture was stirred at 25° C. for 14 h under $N_2$ balloon. The resulting mixture was diluted with EtOAc (200 mL), the mixture was filtered with $SiO_2$ (300 g), the mixture was washed with EtOAc (700 mL) and THE (900 mL), and the organic layers were concentrated in vacuo to give the crude product 6-(2-((4-methoxybenzyl)oxy)ethyl)pentadecanoic acid (6.7 g, 12.36 mmol), which was used in the next step without further purification.

$^1$H NMR (400 MHz, DMSO-d6): δ=11.99 (s, 1H), 7.16~7.27 (m, 2H), 6.88 (d, J=8.8 Hz, 2H), 4.34 (s, 2H), 3.70~3.77 (m, 3H), 2.17 (t, J=7.2 Hz, 2H), 1.40~1.48 (m, 4H), 1.12~1.32 (m, 23H), 0.85 (t, J=6.8 Hz, 3H).

Step 9: Synthesis of (Z)-tridec-2-en-1-yl 6-(2-((4-methoxybenzyl)oxy)ethyl)pentadecanoate To a solution of 6-(2-((4-methoxybenzyl)oxy)ethyl)pentadecanoic acid (6.7 g, 16.48 mmol) in DCM (70 mL) was slowly added (Z)-tridec-2-en-1-ol (4.90 g, 24.72 mmol), DIEA (11.51 mL, 65.9 mmol), DMAP (2.013 g, 16.48 mmol) and EDC (6.32 g, 33.0 mmol) at 0° C., then the mixture was warmed to 25° C. and stirred for 12 h under $N_2$ balloon. The mixture was diluted with water (100 mL) and extracted with DCM (100 mL*2). The combined organic extracts were washed with brine (100*2 mL), and the organic layers were dried over anh. $Na_2SO_4$ and filtered. The filtrate was concentrated in vacuo and the residue was purified by column chromatography ($SiO_2$, Pet. ether:EtOAc=100:1) to give (Z)-tridec-2-en-1-yl 6-(2-((4-methoxybenzyl)oxy)ethyl)pentadecanoate (5 g, 6.82 mmol).

$^1$H NMR (400 MHz, CHLOROFORM-d): δ=7.23~7.27 (m, 2H), 6.87 (d, J=8.8 Hz, 2H), 5.59~5.69 (m, 1H), 5.47~5.56 (m, 1H), 4.61 (d, J=6.8 Hz, 2H), 4.41 (s, 2H), 3.80 (s, 3H), 3.43 (t, J=7.2 Hz, 2H), 2.29 (t, J=7.6 Hz, 2H), 2.09 (q, J=7.2 Hz, 2H), 1.51~1.59 (m, 4H), 1.21~1.36 (m, 37H), 0.87 (t, J=6.8 Hz, 6H). MS (ESI) m/z: 609.5 [M+Na]+.

Step 10: Synthesis of (Z)-tridec-2-en-1-yl 6-(2-hydroxyethyl)pentadecanoate

To a solution of (Z)-tridec-2-en-1-yl 6-(2-((4-methoxybenzyl)oxy)ethyl)pentadecanoate (5 g, 8.52 mmol) in ACN (70 mL) and water (17.5 mL) was slowly added CAN (18.68 g, 34.1 mmol) at 0° C. Then the mixture was warmed up 25° C. and stirred for 3 h under $N_2$ balloon. The resulting mixture was quenched with sat. aq. $Na_2SO_3$ (100 mL) and extracted with EtOAc (100 mL*2). The combined organic extracts were washed with brine (100 mL*2), and the organic layers were dried over anh. $Na_2SO_4$ and filtered. The filtrate was concentrated in vacuo and the residue was purified by column chromatography ($SiO_2$, Pet. ether:EtOAc=25:1 to 10:1) to give (Z)-tridec-2-en-1-yl 6-(2-hydroxyethyl)pentadecanoate (3.5 g, 6.00 mmol).

$^1$H NMR (400 MHz, CHLOROFORM-d): δ=5.59~5.68 (m, 1H), 5.45~5.55 (m, 1H), 4.62 (d, J=7.2 Hz, 2H), 3.65 (t, J=7.2 Hz, 2H), 2.31 (t, J=7.6 Hz, 2H), 2.09 (q, J=7.2 Hz, 2H), 1.59~1.65 (m, 2H), 1.48~1.55 (m, 2H), 1.24~1.39 (m, 37H), 0.88 (t, J=6.8 Hz, 6H).

Step 11: Synthesis of (Z)-tridec-2-en-1-yl 6-(2-oxoethyl)pentadecanoate

To a solution of (Z)-tridec-2-en-1-yl 6-(2-hydroxyethyl) pentadecanoate (3.7 g, 7.93 mmol) in DCM (40 mL) was added DMP (9.54 g, 22.49 mmol) at 0° C. The mixture was stirred at 25° C. for 3 h under $N_2$ balloon. The resulting mixture was diluted with ice water (50 mL) and quenched with sat. aq. $NaHCO_3$ to adjust pH to 7. The resulting mixture was filtered and the filtrate was extracted with DCM (50 mL*2). The combined organic extracts were washed with brine (60 mL), dried over anhydrous $Na_2SO_4$, and filtered. The filtrate was concentrated in vacuo and the residue was purified by column chromatography ($SiO_2$, Pet. ether:EtOAc=100:1 to 20:1) to give (Z)-tridec-2-en-1-yl 6-(2-oxoethyl)pentadecanoate (2.6 g, 4.48 mmol).

$^1$H NMR (400 MHz, CHLOROFORM-d): δ=9.75 (s, 1H), 5.58~5.68 (m, 1H), 5.46~5.53 (m, 1H), 4.61 (d, J=6.8 Hz, 2H), 2.27~2.35 (m, 4H), 2.09 (q, J=7.2 Hz, 2H), 1.95 (s, 1H), 1.62 (s, 2H), 1.24~1.36 (m, 36H), 0.87 (t, J=6.4 Hz, 6H).

Step 12: Synthesis of (Z)-tridec-2-en-1-yl 6-(2-(dimethylamino)ethyl)pentadecanoate To a solution of (Z)-tridec-2-en-1-yl 6-(2-oxoethyl)pentadecanoate (2.6 g, 5.59 mmol) in DCE (40 mL) was added dimethylamine hydrochloride (1.369 g, 16.78 mmol) and sodium triacetoxyhydroborate (3.56 g, 16.78 mmol) at 0° C. Then the mixture was warmed up to 25° C. and stirred for 12 h under $N_2$ balloon. The resulting mixture was diluted by ice water (20 mL), and the resulting mixture was extracted with DCM (40 mL*3). The combined organic extracts were washed with brine (60 mL), dried over anhydrous $Na_2SO_4$, and filtered. The filtrate was concentrated in vacuo and the residue was purified by preparative HPLC (YMC-Actus Pro C18; Condition 35% to 5% water (0.1% TFA)-ACN) to the monoester cationic lipid of Lipid 4, having a structure as set forth below:

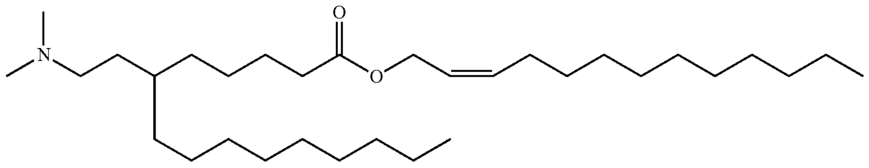 [SMILES: CCCCCCCCCC/C=C\COC(=O)CCCCC(CCCCCCCCC)CCN(C)C]

Lipid 4 i.e., (Z)-tridec-2-en-1-yl 6-(2-(dimethylamino)ethyl)pentadecanoate (1.4 g, 2.83 mmol).

$^1$H NMR (400 MHz, CHLOROFORM-d): δ=5.59~5.68 (m, 1H), 5.46~5.55 (m, 1H), 4.61 (d, J=6.8 Hz, 2H), 2.99 (d, J=4.8 Hz, 2H), 2.83 (s, 6H), 2.31 (t, J=7.6 Hz, 2H), 2.08 (q, J=7.2 Hz, 2H), 1.57~1.69 (m, 4H), 1.22~1.39 (m, 37H), 0.87 (t, J=6.8 Hz, 6H). MS (ESI) m/z: 494.9 [M+H]+.

Example 5: Synthesis of Lipid 5, pentyl (14Z,17Z)-4-(2-(dimethylamino)ethyl)tricosa-14,17-dienoate

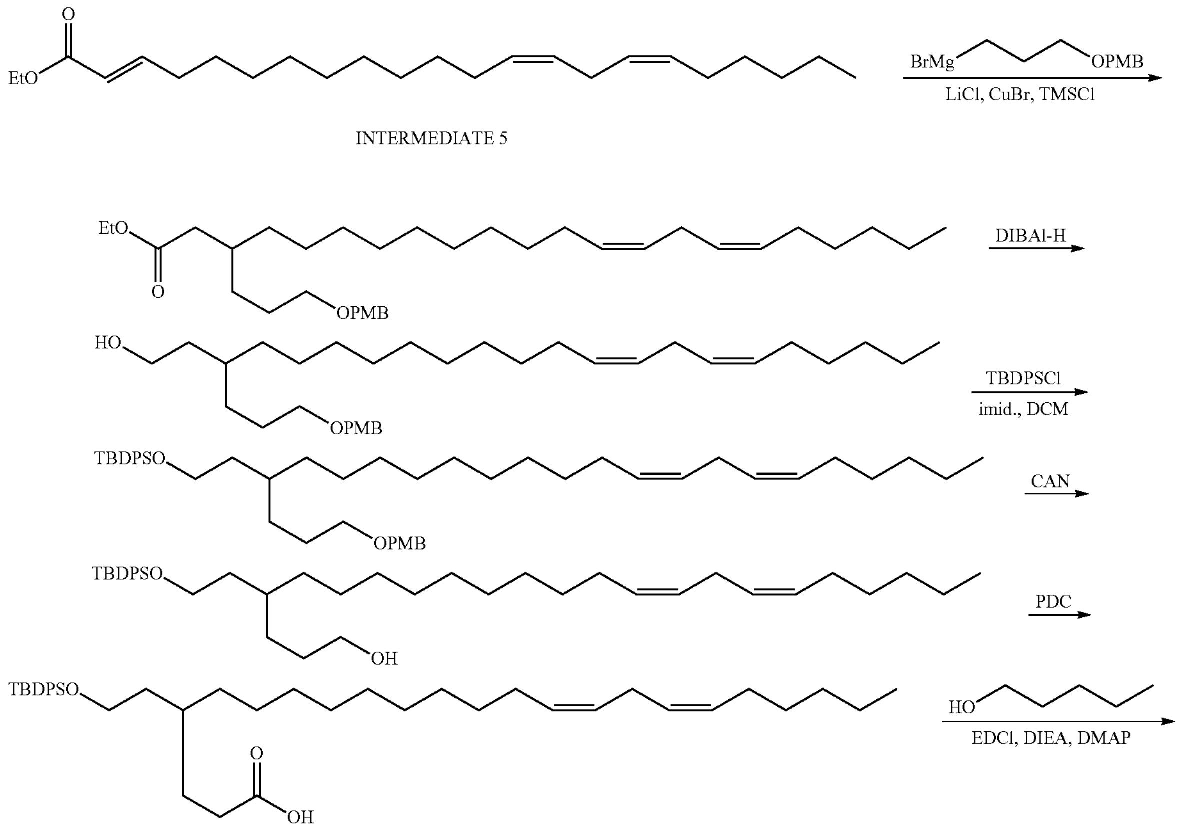

-continued

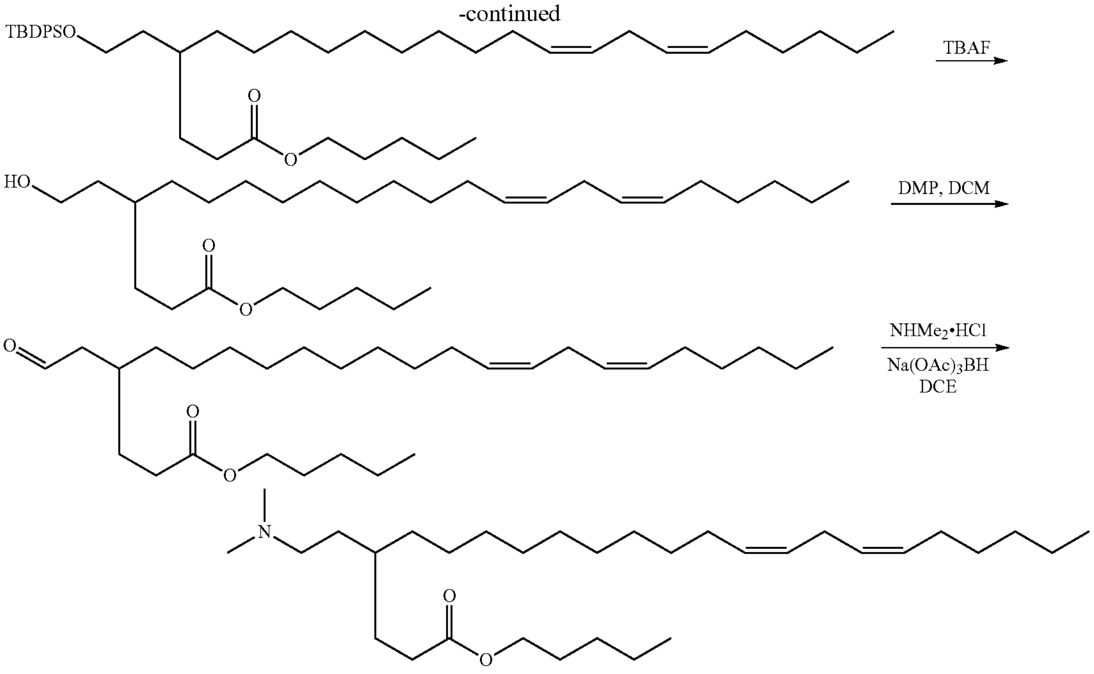

Lipid 5

Step 1: Synthesis of (13Z, 16Z)-ethyl-3-(3-((4-methoxybenzyl)oxy)propyl)docosa-13,16-dienoate To a solution of copper(I) bromide (0.831 g, 5.79 mmol), lithium chloride (0.491 g, 11.58 mmol) [dried under high heated gun, and cool to room temperature], in THF (20 mL) the solution was prepared and stirred for 5 min, then was slowly added (2E,13Z,16Z)-ethyl docosa-2,13,16-trienoate (7 g, 19.31 mmol), TMSCl (2.96 mL, 23.17 mmol) to the above mixture at 0° C. and the mixture was stirred for 15 min, then (3-((4-methoxybenzyl)oxy)propyl)magnesium bromide (300 mL, 116 mmol) THE solution was added to the above mixture, and the mixture was stirred for 2 h at 0° C. The resulting mixture was quenched with sat. aq. $NH_4Cl$ (50 mL), diluted with water (50 mL), and extracted with EtOAc (100 mL*3). The combined organic layers were washed with brine (500 mL), organic layers were separated, dried over $Na_2SO_4$, filtered and the filtrate was concentrated in vacuo. The residue was purified by column chromatography ($SiO_2$, Pet. ether:EtOAc=10:1) to give the title product (13Z,16Z)-ethyl 3-(3-((4-methoxybenzyl)oxy)propyl)docosa-13,16-dienoate (10 g, 16.58 mmol).

$^1H$ NMR (500 MHz, CHLOROFORM-d): δ=7.26 (d, J=8.5 Hz, 2H), 6.88 (d, J=8.5 Hz, 2H), 5.28~5.49 (m, 4H), 4.43 (s, 3H), 4.12 (q, J=7.0 Hz, 2H), 3.81 (s, 3H), 3.43 (t, J=6.5 Hz, 2H), 2.78 (t, J=7.0 Hz, 2H), 2.23 (d, J=6.5 Hz, 2H), 2.06 (q, J=7.0 Hz, 4H), 1.79~1.92 (m, 1H), 1.54~1.67 (m, 4H), 1.21~1.44 (m, 27H), 0.90 (t, J=7.0 Hz, 3H). MS (ESI) m/z: 565.4 [M+Na]+.

Step 2: Synthesis of (13Z,16Z)-3-(3-((4-methoxybenzyl)oxy)propyl)docosa-13,16-dien-1-ol To a solution of (13Z,16Z)-ethyl 3-(3-((4-methoxybenzyl)oxy)propyl)docosa-13,16-dienoate (9 g, 14.92 mmol) in THF (90 mL) was added DIBAL-H (44.8 mL, 44.8 mmol) under $N_2$ protection at 0° C., then the mixture was at 0° C. and stirred for 1 h. The resulting mixture was then quenched with sat. aq. sodium potassium tartrate tetrahydrate solution (200 mL), extracted with EtOAc (300 mL*3), combined organic layers, washed with brine (1000 mL), organic layer was separated and dried over $Na_2SO_4$, filtered and the filtrate was concentrated in vacuo, the residue was purified by column chromatography ($SiO_2$, Pet. ether:EtOAc=5:1 to 3:1) to give the title product (13Z,16Z)-3-(3-((4-methoxybenzyl)oxy)propyl)docosa-13,16-dien-1-ol (6.4 g, 12.78 mmol).

$^1H$ NMR (400 MHz, CHLOROFORM-d): δ=7.26 (d, J=8.4 Hz, 2H), 6.88 (d, J=8.4 Hz, 2H), 5.28~5.49 (m, 4H), 4.43 (s, 3H), 3.81 (s, 3H), 3.66 (t, J=6.4 Hz, 2H), 3.43 (t, J=6.4 Hz, 2H), 2.77 (t, J=6.4 Hz, 2H), 2.05 (q, J=6.8 Hz, 4H), 1.18~1.73 (m, 29H), 0.90 (t, J=7.0 Hz, 3H).

Step 3: Synthesis of tert-butyl(((13Z,16Z)-3-(3-((4-methoxybenzyl)oxy)propyl)docosa-13,16-dien-1-yl)oxy)diphenylsilane To a solution of 1H-imidazole (1.903 g, 28.0 mmol), (13Z,16Z)-3-(3-((4-methoxybenzyl)oxy)-propyl)docosa-13,16-dien-1-ol (7 g, 13.98 mmol) in DCM (70 mL) was slowly added tert-butylchlorodiphenylsilane (4.69 ml, 20.97 mmol) at 0° C. under $N_2$ balloon. The reaction mixture was allowed to warm to 20° C. and stirred for 12 h. The reaction was quenched with sat. aq. $NH_4Cl$ solution (100 mL) at 0° C., and the resulting mixture was extracted with DCM (300 mL*2). The combined organic extracts were washed with brine (1200 mL), dried over anh. $Na_2SO_4$, and filtered. The filtrate was concentrated in vacuo and the residue was purified by column chromatography ($SiO_2$, Pet. ether:EtOAc=20:1) to give tert-butyl(((13Z,16Z)-3-(3-((4-methoxybenzyl)oxy)propyl)docosa-13,16-dien-1-yl)oxy)diphenylsilane (10 g, 12.85 mmol).

$^1H$ NMR (500 MHz, CHLOROFORM-d): δ=7.68 (d, J=7.0 Hz, 4H), 7.33~7.46 (m, 6H), 7.26 (d, J=8.5 Hz, 2H), 6.88 (d, J=8.5 Hz, 2H), 5.28~5.49 (m, 4H), 4.43 (s, 3H), 3.81 (s, 3H), 3.68 (t, J=6.5 Hz, 2H), 3.43 (t, J=6.4 Hz, 2H), 2.77 (t, J=6.4 Hz, 2H), 2.05 (q, J=6.8 Hz, 4H), 1.15~1.60 (m, 29H), 1.05 (s, 9H), 0.90 (t, J=7.0 Hz, 3H).

Step 4: Synthesis of (14Z,17Z)-4-(2-((tert-butyldiphenylsilyl)oxy)ethyl)tricosa-14,17-dien-1-olnylsilane To a solution of tert-butyl(((13Z,16Z)-3-(3-((4-methoxybenzyl)oxy)propyl)docosa-13,16-dien-1-yl)oxy)diphenylsilane (8 g, 10.82 mmol) in ACN (96 mL), water (32 mL) solution was added CAN (23.73 g, 43.3 mmol) at 0° C., then the mixture was warmed up to 30° C. and further stirred for 4 h. The resulting mixture was quenched with sat. aq. $Na_2SO_3$ (50 mL), ice water (50 mL) was diluted, the resulting mixture was extracted with EtOAc (300 mL*2), combined organic layers were washed with brine (500 mL*2), organic layers were dried over $Na_2SO_4$, filtered and the filtrate was concentrated in vacuo. The reside was purified by p-TLC ($SiO_2$, Pet. ether:EtOAc=50:1, 10:1) to give the title product (14Z,17Z)-4-(2-((tert-butyldiphenylsilyl)-oxy)ethyl)tricosa-14,17-dien-1-ol (3.5 g, 5.65 mmol).

$^1$H NMR (500 MHz, CHLOROFORM-d): δ=7.68 (d, J=7.0 Hz, 4H), 7.33~7.46 (m, 6H), 5.28~5.49 (m, 4H), 3.68 (t, J=6.5 Hz, 2H), 3.58 (t, J=6.5 Hz, 2H), 2.77 (t, J=6.4 Hz, 2H), 2.05 (q, J=6.8 Hz, 4H), 1.15~1.60 (m, 29H), 1.05 (s, 9H), 0.90 (t, J=7.0 Hz, 3H).

Step 5: Synthesis of (14Z,17Z)-4-(2-((tert-butyldiphenylsilyl)oxy)ethyl)tricosa-14,17-dienoic Acid To a solution of (14Z,17Z)-4-(2-((tert-butyldiphenylsilyl)oxy)ethyl)tricosa-14,17-dien-1-ol (2.5 g, 4.04 mmol) in DMF (60 mL) was added PDC (7.60 g, 20.19 mmol) at 0° C., and the mixture was stirred at 0° C. for 30 min, then warmed up to 30° C. and stirred for 12 h. The mixture was diluted with EtOAc (300 mL), filtered by column chromatography ($SiO_2$, EtOAc to THF), and then the filtrate was concentrated in vacuo to give the crude product (14Z,17Z)-4-(2-((tert-butyldiphenylsilyl)oxy)ethyl)tricosa-14,17-dienoic acid (2.8 g, 2.65 mmol), which was directly used in the subsequent step without further purification.

$^1$H NMR (500 MHz, CHLOROFORM-d): δ=7.68 (d, J=7.0 Hz, 4H), 7.33~7.46 (m, 6H), 5.28~5.49 (m, 4H), 3.68 (t, J=6.5 Hz, 1H), 2.77 (t, J=6.4 Hz, 2H), 2.28 (t, J=8.0 Hz, 2H), 2.05 (q, J=6.8 Hz, 4H), 1.15~1.60 (m, 27H), 1.05 (s, 9H), 0.90 (t, J=7.0 Hz, 3H).

Step 6: Synthesis of (14Z,17Z)-pentyl 4-(2-((tert-butyldiphenylsilyl)oxy)ethyl)tricosa-14,17-dienoate To a solution of (14Z,17Z)-4-(2-((tert-butyldiphenylsilyl)oxy)ethyl)tricosa-14,17-dienoic acid (2.8 g, 2.65 mmol) in DCM (30 mL) was added pentan-1-ol (0.702 g, 7.96 mmol), EDC (1.526 g, 7.96 mmol), DMAP (0.324 g, 2.65 mmol), DIEA (1.854 mL, 10.62 mmol) at 0° C., then the mixture was warmed to 30° C., and the mixture was stirred at 30° C. for 12 h. The resulting mixture was directly purified by column chromatography ($SiO_2$, Pet. ether:EtOAc=20:1) to give the title product (14Z,17Z)-pentyl 4-(2-((tert-butyldiphenylsilyl)oxy)ethyl)tricosa-14,17-dienoate (1.1 g, 1.486 mmol).

$^1$H NMR (500 MHz, CHLOROFORM-d): δ=7.68 (d, J=7.0 Hz, 4H), 7.33~7.46 (m, 6H), 5.28~5.49 (m, 4H), 4.04 (t, J=6.5 Hz, 2H), 3.68 (t, J=6.5 Hz, 2H), 2.77 (t, J=6.4 Hz, 2H), 2.23 (t, J=8.0 Hz, 2H), 2.05 (q, J=6.8 Hz, 4H), 1.15~1.65 (m, 33H), 1.05 (s, 9H), 0.88~0.92 (m, 6H).

Step 7: Synthesis of (14Z,17Z)-pentyl 4-(2-hydroxyethyl)tricosa-14,17-dienoate To a solution of (14Z,17Z)-pentyl 4-(2-((tert-butyldiphenylsilyl)oxy)ethyl)tricosa-14,17-dienoate (1.1 g, 1.564 mmol) in THF (10 mL) was added TBAF (10 mL, 10.00 mmol) at 0° C., and the mixture was stirred at 0° C. for 30 min, then warmed up to 30° C. and stirred for 12 h. The mixture was diluted with water (10 mL) and extracted with EtOAc (20 mL*2). The combined organic layers were washed with brine (40 mL), the organic layer was separated and dried over $Na_2SO_4$, filtered, and concentrated in vacuo. The residue was purified by column chromatography ($SiO_2$, Pet. ether:EtOAc=10:1) to give the product (14Z,17Z)-pentyl 4-(2-hydroxyethyl)tricosa-14,17-dienoate (600 mg, 1.226 mmol).

$^1$H NMR (500 MHz, CHLOROFORM-d): δ=5.28~5.42 (m, 4H), 4.07 (t, J=6.5 Hz, 2H), 3.70 (t, J=6.5 Hz, 2H), 2.77 (t, J=6.5 Hz, 2H), 2.30 (t, J=8.0 Hz, 2H), 2.05 (q, J=6.5 Hz, 4H), 1.15~1.65 (m, 33H), 0.88~0.92 (m, 6H).

Step 8: Synthesis of (14Z,17Z)-pentyl 4-(2-oxoethyl)tricosa-14,17-dienoate

To a solution of (14Z,17Z)-pentyl 4-(2-hydroxyethyl) tricosa-14,17-dienoate (600 mg, 1.291 mmol) in DCM (18 mL) was added DMP (1643 mg, 3.87 mmol) at 0° C., then the mixture was warmed to 30° C. and further stirred for 4 h. The resulting mixture was diluted with ice water (20 mL), and the resulting mixture was extracted with DCM (30 mL*2), organic layers were combined, washed with brine (50 mL*2), and the organic layers were dried over $Na_2SO_4$, filtered and the filtrate was concentrated in vacuo. The residue was purified by column chromatography ($SiO_2$, Pet. ether:EtOAc=5:1) to give the title product (14Z,17Z)-pentyl 4-(2-oxoethyl)tricosa-14,17-dienoate (400 mg, 0.864 mmol).

$^1$H NMR (500 MHz, CHLOROFORM-d): δ=9.77 (s, 1H), 5.28~5.42 (m, 4H), 4.07 (t, J=6.5 Hz, 2H), 3.70 (t, J=6.5 Hz, 2H), 2.77 (t, J=6.5 Hz, 2H), 2.31 (t, J=7.5 Hz, 2H), 2.05 (q, J=6.5 Hz, 4H), 1.15~1.65 (m, 31H), 0.88~0.92 (m, 6H).

Step 9: Synthesis of pentyl (14Z,17Z)-4-(2-(dimethylamino)ethyl)tricosa-14,17-dienoate To a solution of (14Z,17Z)-pentyl 4-(2-oxoethyl)tricosa-14,17-dienoate (400 mg, 0.864 mmol) in DCE (10 mL) was added dimethylamine hydrochloride (211 mg, 2.59 mmol), sodium triacetoxyhydroborate (550 mg, 2.59 mmol) at 0° C., then the mixture was warmed to 30° C. and further stirred for 12 h. The resulting mixture was diluted with ice water (10 mL), and the mixture was extracted with DCM (20 mL*2), organic layers were combined, washed with brine (50 mL*2), and organic layers were dried over $Na_2SO_4$, filtered and the filtrate was concentrated in vacuo. The residue was purified by preparative HPLC (YMC-Actus Pro C18; Condition 35% to 5% water (0.1% TFA)-ACN), which is the monoester cationic lipid of Lipid 5, having a structure as set forth below:

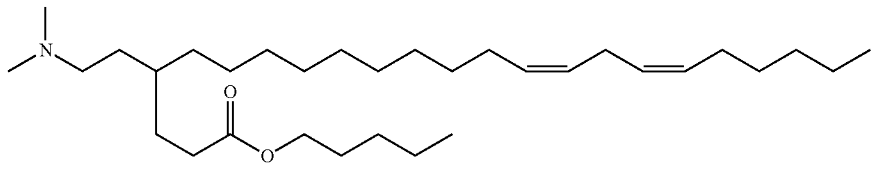 [SMILES: CCCCC/C=C\C/C=C\CCCCCCCCCC(CCC(=O)OCCCCC)CCN(C)C]
Lipid 5
(14Z,17Z)-pentyl 4-(2-(dimethylamino)ethyl)tricosa-14,17-dienoate (226.68 mg, 0.461 mmol).
$^1$H NMR (500 MHz, CHLOROFORM-d): δ=9.77 (s, 1H), 5.28~5.42 (m, 4H), 4.06 (t, J=6.5 Hz, 2H), 3.00~3.13 (m, 2H), 2.84 (s, 6H), 2.77 (t, J=6.5 Hz, 2H), 2.31 (t, J=7.5 Hz, 2H), 2.05 (q, J=7.0 Hz, 4H), 1.15~1.72 (m, 33H), 0.88~0.92 (m, 6H). MS (ESI) m/z: 492.5 [M+H]+.
Example 6: Synthesis of Lipid 6, (Z)-oct-2-en-1-yl 11-(2-(dimethylamino)-ethyl)icosanoate
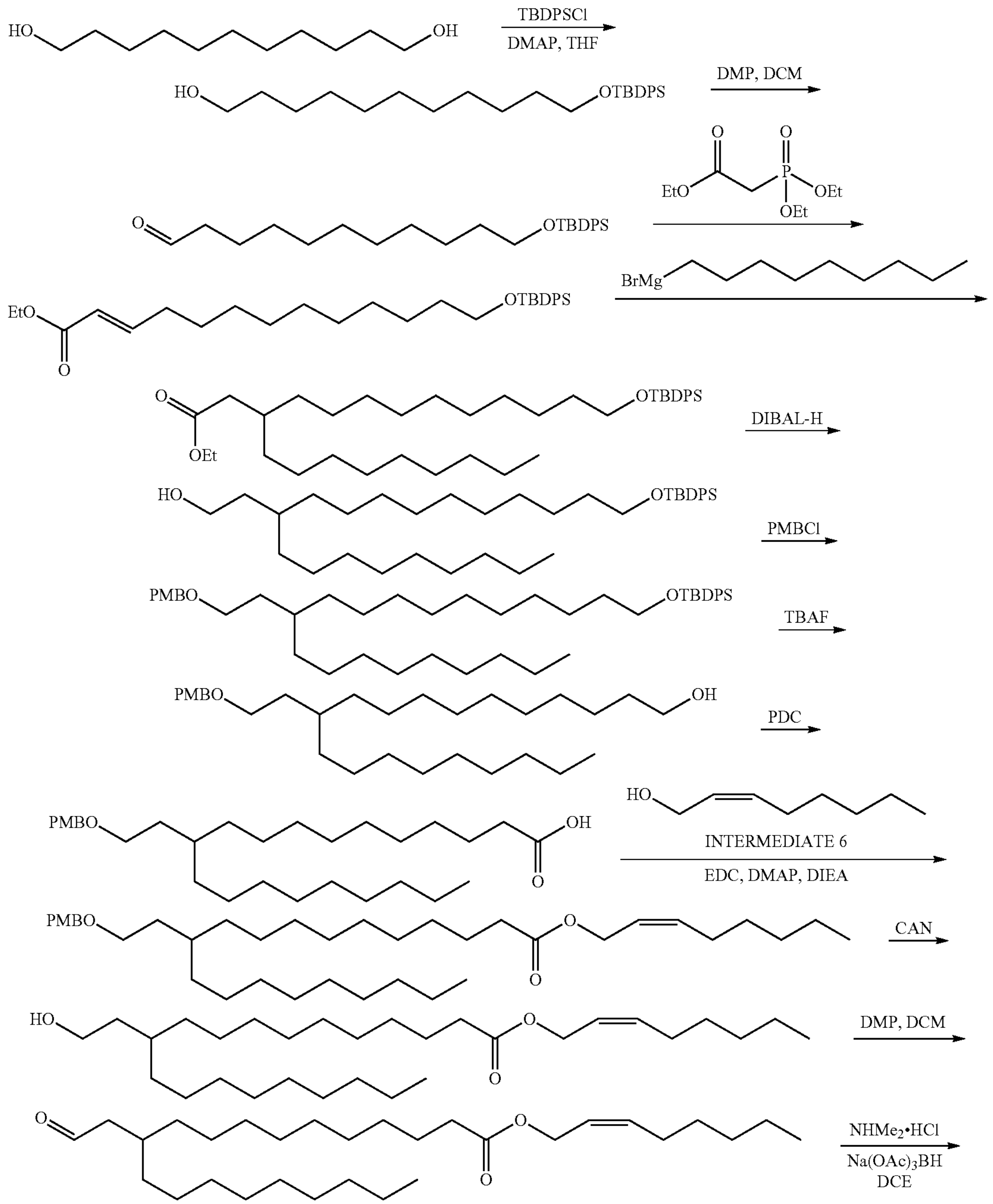

-continued

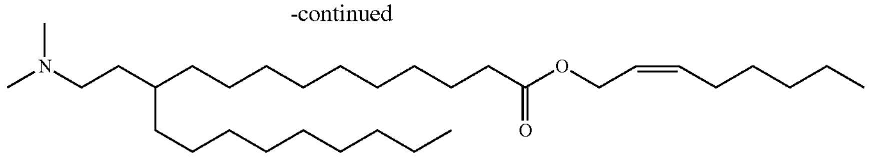

Lipid 6

Step 1: Synthesis of 11-((tert-butyldiphenylsilyl)oxy)undecan-1-ol

To a solution of undecane-1,11-diol (25 g, 133 mmol) in THF (250 mL) was added imidazole (18.08 g, 266 mmol), DMAP (1.622 g, 13.28 mmol). Then TBDPSCl (33.8 ml, 131 mmol) was added to the above mixture at 0° C. and the reaction was heated to 25° C. and stirred for 16 h. The reaction was cooled to 0° C. and water (200 mL) was added. Then it was extracted with EtOAc (200 mL*2), combined organic layers, washed with brine (100 mL*2), dried over anhydrous $Na_2SO_4$, filtered, and concentrated in vacuo. The residue was purified by column chromatography ($SiO_2$, Pet. ether:EtOAc=20:1 to 5:1) to give 11-((tert-butyldiphenylsilyl)oxy)undecan-1-ol (30 g, 70.3 mmol).

$^1H$ NMR (500 MHz, CHLOROFORM-d): δ 7.68 (d, J=7.0 Hz, 4H), 7.37~7.44 (m, 6H), 3.64~3.67 (m, 4H), 1.53~1.59 (m, 4H), 1.26~1.35 (m, 14H), 1.05 (s, 9H).

Step 2: Synthesis of 11-((tert-butyldiphenylsilyl)oxy)undecanal

To a solution of 11-((tert-butyldiphenylsilyl)oxy)undecan-1-ol (30 g, 70.3 mmol) in DCM (300 mL) was added DMP (74.5 g, 176 mmol) at 0° C., then the mixture was stirred at 25° C. for 3 h. The resulting mixture was quenched with ice water (500 mL) and filtered. The filtrate was extracted with DCM (500 mL*3), combined organic layers were washed with brine (1000 mL), and organic layer was separated and dried over $Na_2SO_4$, filtered, and concentrated in vacuo. The residue was purified by column chromatography ($SiO_2$, Pet. ether:EtOAc=20:1) to give 11-((tert-butyldiphenylsilyl)oxy)undecanal (21 g, 47.0 mmol).

$^1H$ NMR (500 MHz, CHLOROFORM-d): δ 9.77 (s, 1H), 7.68 (d, J=7.0 Hz, 4H), 7.37~7.44 (m, 6H), 3.66 (d, J=6.5 Hz, 2H), 2.42~2.44 (m, 2H), 1.56~1.63 (m, 4H), 1.26~1.34 (m, 12H), 1.05 (s, 9H).

Step 3: Synthesis of (E)-ethyl 13-((tert-butyldiphenylsilyl)oxy)tridec-2-enoate To a solution of ethyl 2-(diethoxyphosphoryl)acetate (15.52 g, 69.2 mmol) in THF (210 mL) was slowly added NaH (2.57 g, 64.3 mmol) at 0° C. under $N_2$ balloon. The reaction mixture was stirred for 40 min at 0° C. Then the solution of 11-((tert-butyldiphenylsilyl)oxy)undecanal (21 g, 49.4 mmol) in THF (20 mL) was added to the above mixture at 0° C. The reaction mixture was stirred at 20° C. for 4 h. The resulting mixture was quenched with sat. aq. $NH_4Cl$ (100 mL), then water (100 mL) was added to the above mixture at 0° C., and the resulting mixture was extracted with EtOAc (200 mL*2). The combined organic extracts were washed with brine (500 mL), dried over anh. $Na_2SO_4$, and filtered. The filtrate was concentrated and the residue was purified by column chromatography ($SiO_2$, Pet. ether:EtOAc=100:1) to give (E)-ethyl 13-((tert-butyldiphenylsilyl)oxy)tridec-2-enoate (21 g, 40.3 mmol).

$^1H$ NMR (500 MHz, CHLOROFORM-d): δ 7.68 (d, J=7.0 Hz, 4H), 7.37~7.43 (m, 6H), 6.96~6.99 (m, 1H), 5.78~5.86 (m, 1H), 4.16~4.23 (m, 2H), 3.67 (d, J=5.5, 12.5 Hz, 2H), 2.19~2.21 (m, 2H), 1.44~1.59 (m, 4H), 1.26~1.31 (m, 15H), 1.05 (s, 9H).

Step 4: Synthesis of Ethyl 13-((tert-butyldiphenylsilyl)oxy)-3-nonyltridecanoate A solution of copper(I) bromide (1.305 g, 9.09 mmol), lithium chloride (0.771 g, 18.19 mmol) in THF (20 mL) was stirred for 10 min, then (E)-ethyl 13-((tert-butyldiphenylsilyl)oxy)tridec-2-enoate (15 g, 30.3 mmol), TMSCl (4.65 mL, 36.4 mmol) was slowly added to the above mixture at 0° C. under $N_2$ balloon. The mixture was stirred for 30 min. Then freshly prepared nonylmagnesium bromide (42.1 g, 182 mmol) was added to the above mixture, and the mixture was stirred for 2 h at 0° C. The resulting mixture was quenched with sat. aq. $NH_4Cl$ (150 mL), and water (40 mL) was added to the above mixture. The reaction mixture was extracted with EtOAc (200 mL*2). The combined organic extracts were washed with brine (260 mL), dried over anhydrous $Na_2SO_4$ and filtered. The filtrate was concentrated in vacuo and the residue was purified by column chromatography ($SiO_2$, Pet. ether:EtOAc=100:1 to 20:1) to give the product ethyl 13-((tert-butyldiphenylsilyl)oxy)-3-nonyltridecanoate (15 g, 19.26 mmol).

$^1H$ NMR (400 MHz, CHLOROFORM-d): δ 7.63~7.70 (m, 4H), 7.34~7.46 (m, 6H), 4.13 (q, J=7.2 Hz, 2H), 3.65 (t, J=6.8 Hz, 2H), 2.22 (d, J=7.2 Hz, 2H), 1.85 (s, 1H), 1.52~1.59 (m, 2H), 1.26 (d, J=2.4 Hz, 35H), 1.05 (s, 9H), 0.88 (t, J=6.8 Hz, 3H).

Step 5: Synthesis of 13-((tert-butyldiphenylsilyl)oxy)-3-nonyltridecan-1-ol

To a solution of ethyl 13-((tert-butyldiphenylsilyl)oxy)-3-nonyltridecanoate (21 g, 33.7 mmol) in THF (210 mL) was slowly added DIBAL-H (101 mL, 101 mmol) at 0° C., and the mixture was stirred for 2 h at 0° C. Then the mixture was quenched with sat. aq. sodium potassium tartrate tetrahydrate (200 mL). The mixture was extracted with EtOAc (200 mL*2). The combined organic extracts were washed with brine (260 mL), dried over anhydrous $Na_2SO_4$, and filtered. The filtrate was concentrated in vacuo. The residue was purified by column chromatography ($SiO_2$, Pet. ether: EtOAc=10:1) to give 13-((tert-butyldiphenylsilyl)oxy)-3-nonyltridecan-1-ol (18 g, 24.78 mmol).

$^1H$ NMR (400 MHz, CHLOROFORM-d): δ 7.68 (dd, J=8.0, 1.2 Hz, 4H), 7.35~7.45 (m, 6H), 3.64~3.68 (m, 4H), 1.50~1.60 (m, 4H), 1.24~1.37 (m, 33H), 1.05 (s, 9H), 0.89 (t, J=6.8 Hz, 3H).

Step 6: Synthesis of tert-butyl((11-(2-((4-methoxybenzyl)oxy)ethyl)icosyl)oxy)-diphenylsilane To a solution of 13-((tert-butyldiphenylsilyl)oxy)-3-nonyltridecan-1-ol (11 g, 18.93 mmol) in DMF (150 mL) was added TBAI (6.99 g, 18.93 mmol) and NaH (4.54 g, 114 mmol) at 0° C. under $N_2$ balloon. The mixture was stirred at 0° C. for 30 min. Then 4-methoxybezyl chloride (15.34 mL, 114 mmol) was added to the above mixture and stirred at 25° C. for 2 h. The mixture was quenched with sat. aq. $NH_4Cl$ solution (160 mL) at 0° C. and extracted with EtOAc (200 mL*2). The combined organic extracts were washed with brine (260 mL*2), dried over anhydrous $Na_2SO_4$, and filtered. The filtrate was concentrated and the residue was purified by column chromatography ($SiO_2$, Pet. ether:EtOAc=5:1) to give the product tert-butyl((11-(2-((4-methoxybenzyl)-oxy)ethyl)icosyl)oxy)diphenylsilane (10 g, 11.41 mmol).

$^1H$ NMR (400 MHz, CHLOROFORM-d): δ 7.67 (dd, J=7.6, 1.6 Hz, 4H), 7.34~7.44 (m, 6H), 7.26~7.29 (m, 2H), 6.85~6.89 (m, 2H), 4.43 (s, 2H), 3.78~3.82 (m, 5H), 3.45 (t, J=7.0 Hz, 2H), 1.52~1.57 (m, 4H), 1.22~1.34 (m, 33H), 1.05 (s, 9H), 0.86~0.90 (m, 3H).

Step 7: Synthesis of 11-(2-((4-methoxybenzyl)oxy) ethyl)icosan-1-ol

To a solution of tert-butyl((11-(2-((4-methoxybenzyl) oxy)ethyl)icosyl)oxy)diphenylsilane (15 g, 21.39 mmol) in THF (70 mL) was added TBAF (107 mL, 107 mmol) at 0° C. and the mixture was stirred for 12 h at 25° C. The resulting mixture was quenched with $H_2O$ (200 mL) at 0° C. and the resulting mixture was extracted with EtOAc (200 mL*2). The combined organic extracts were washed with brine (200 mL), dried over anh. $Na_2SO_4$, and filtered. The filtrate was concentrated in vacuo and the residue was purified by column chromatography ($SiO_2$, Pet. ether:EtOAc=20:1 to 10:1) to give the product 11-(2-((4-methoxybenzyl)oxy)ethyl)icosan-1-ol (8 g, 13.83 mmol).

$^1H$ NMR (400 MHz, CHLOROFORM-d): δ 7.25 (d, J=4.4 Hz, 2H), 6.87 (d, J=8.8 Hz, 2H), 4.43 (s, 2H), 3.80 (s, 3H), 3.64 (t, J=6.8 Hz, 2H), 3.45 (t, J=7.2 Hz, 2H), 1.53~1.59 (m, 4H), 1.21~1.35 (m, 33H), 0.86~0.90 (m, 3H).

Step 8: Synthesis of 11-(2-((4-methoxybenzyl)oxy)ethyl)icosanoic Acid

To a solution of 11-(2-((4-methoxybenzyl)oxy)ethyl) icosan-1-ol (8 g, 17.29 mmol) in DMF (70 mL) was slowly added PDC (32.5 g, 86 mmol) at 0° C. The reaction mixture was stirred at 25° C. for 14 h under $N_2$ balloon. The resulting mixture was diluted with EtOAc (200 mL), the mixture was filtered with $SiO_2$ (300 g), the mixture was washed with EtOAc (700 mL) and THE (900 mL), and the organic layers were concentrated in vacuo to give the crude product 11-(2-((4-methoxybenzyl)oxy)ethyl)icosanoic acid (8 g, 12.59 mmol), which was used in the subsequent step without further purification.

$^1H$ NMR (500 MHz, DMSO-d6): δ 11.99 (s, 1H), 7.14~7.25 (m, 2H), 6.87 (d, J=5.8 Hz, 2H), 4.34 (s, 2H), 3.73 (s, 3H), 2.17 (s, 2H), 1.45 (s, 4H), 1.22 (s, 33H), 0.85 (s, 3H).

Step 9: Synthesis of (Z)-oct-2-en-1-yl 11-(2-((4-methoxybenzyl)oxy)ethyl)icosanoate To a solution of 11-(2-((4-methoxybenzyl)oxy)ethyl)icosanoic acid (8 g, 16.78 mmol) in DCM (150 mL) was slowly added (Z)-oct-2-en-1-ol (2.367 g, 18.46 mmol), DIEA (11.72 mL, 67.1 mmol), DMAP (2.050 g, 16.78 mmol) and EDC (6.43 g, 33.6 mmol) at 0° C. Then the mixture was warmed to 25° C. and stirred for 16 h under $N_2$ balloon. The resulting mixture was diluted with water (100 mL) and extracted with DCM (100 mL*2). The combined organic extracts were washed with brine (100 mL*2), and the organic layers were dried over anhydrous $Na_2SO_4$ and filtered. The filtrate was concentrated under reduced pressure and the residue was purified by column chromatography ($SiO_2$, Pet. ether:EtOAc=100:1 to 20:1) to give (Z)-oct-2-en-1-yl 11-(2-((4-methoxybenzyl)oxy)ethyl)icosanoate (5 g, 6.82 mmol).

$^1H$ NMR (500 MHz, CHLOROFORM-d): δ 7.25~7.26 (m, 2H), 6.85~6.89 (m, 2H), 5.61~5.68 (m, 1H), 5.49~5.56 (m, 1H), 4.62 (d, J=7.0 Hz, 2H), 4.42 (s, 2H), 3.80 (s, 3H), 3.45 (t, J=7.5 Hz, 2H), 2.30 (t, J=7.5 Hz, 2H), 2.09 (q, J=7.0 Hz, 2H), 1.59~1.65 (m, 2H), 1.52~1.55 (m, 2H), 1.34~1.39 (m, 2H), 1.21~1.31 (m, 35H), 0.8~090 (m, 6H).

Step 10: Synthesis of (Z)-oct-2-en-1-yl 11-(2-hydroxyethyl)icosanoate

To a solution of (Z)-oct-2-en-1-yl 11-(2-((4-methoxybenzyl)oxy)ethyl)icosanoate (5 g, 8.52 mmol) in ACN (70 mL) and water (17.5 mL) was slowly added CAN (18.68 g, 34.1 mmol) at 0° C. Then the mixture was warmed to 25° C. and stirred for 3 h under $N_2$ balloon. The resulting mixture was quenched with sat. aq. $Na_2SO_3$ (100 mL) and extracted with EtOAc (100 mL*2). The combined organic extracts were washed with brine (100 mL*2), and the organic layers were dried over anhydrous $Na_2SO_4$ and filtered. The filtrate was concentrated in vacuo and the residue was purified by column chromatography ($SiO_2$, Pet. ether:EtOAc=25:1 to 10:1) to give (Z)-oct-2-en-1-yl 11-(2-hydroxyethyl)icosanoate (3.5 g, 6.00 mmol).

$^1H$ NMR (500 MHz, CHLOROFORM-d): δ 5.59~5.69 (m, 1H), 5.48~5.55 (m, 1H), 4.62 (d, J=6.5 Hz, 2H), 3.66 (t, J=7.0 Hz, 2H), 2.30 (t, J=7.5 Hz, 2H), 2.09 (q, J=7.0 Hz, 2H), 1.55~1.65 (m, 4H), 1.52 (q, J=6.9 Hz, 2H), 1.35~1.40 (m, 2H), 1.23~1.31 (m, 33H), 0.88 (td, J=7.0, 2.5 Hz, 6H).

Step 11: Synthesis of (Z)-oct-2-en-1-yl 11-(2-hydroxyethyl)icosanoate

To a solution of (Z)-oct-2-en-1-yl 11-(2-hydroxyethyl) icosanoate (3.5 g, 7.50 mmol) in DCM (40 mL) was added DMP (9.54 g, 22.49 mmol) at 0° C. The mixture was stirred at 25° C. for 3 h under $N_2$ balloon. The resulting mixture was diluted with ice water (50 mL) and quenched with sat. aq. $NaHCO_3$ to adjust pH to 7. The resulting mixture was filtered and the filtrate was extracted with DCM (50 mL*2). The combined organic extracts were washed with brine (60 mL), dried over anhydrous $Na_2SO_4$, and filtered. The filtrate was concentrated in vacuo and the residue was purified by column chromatography ($SiO_2$, Pet. ether:EtOAc=100:1 to 20:1) to give (Z)-oct-2-en-1-yl 11-(2-oxoethyl)icosanoate (2.6 g, 4.48 mmol).

$^1H$ NMR (500 MHz, CHLOROFORM-d): δ 9.75 (t, J=2.5 Hz, 1H), 5.61~5.68 (m, 1H), 5.48~5.56 (m, 1H), 4.61 (d, J=6.5 Hz, 2H), 2.28~2.34 (m, 4H), 2.09 (q, J=7.0 Hz, 2H), 1.59~1.65 (m, 2H), 1.23~1.38 (m, 37H), 0.85~0.89 (m, 6H).

Step 12: Synthesis of (Z)-oct-2-en-1-yl 11-(2-hydroxyethyl)icosanoate

To a solution of (Z)-oct-2-en-1-yl 11-(2-oxoethyl)icosanoate (2.6 g, 5.59 mmol) in DCE (40 mL) was added dimethylamine hydrochloride (1.369 g, 16.78 mmol) and sodium triacetoxyhydroborate (3.56 g, 16.78 mmol) at 0° C. Then the mixture was warmed to 25° C. and stirred for 12 h under $N_2$ balloon. The resulting mixture was diluted with ice water (20 mL) and t extracted with DCM (40 mL*3). The combined organic extracts were washed with brine (60 mL), dried over anhydrous $Na_2SO_4$, and filtered. The filtrate was concentrated in vacuo and the residue was purified by preparative HPLC (Y Agela DuraShell; Condition Isocratic 12% water (0.1% TFA)-ACN) to provide a monoester cationic lipid of Lipid 6, having a structure as set forth below:

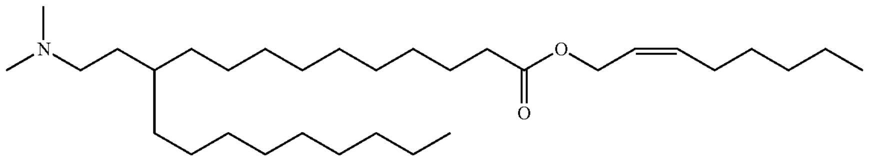 [SMILES: CCCCC/C=C\COC(=O)CCCCCCCCCC(CCCCCCCCC)CCN(C)C]

Lipid 6

(Z)-oct-2-en-1-yl 11-(2-(dimethylamino)ethyl)icosanoate (1.5 g, 3.04 mmol).

$^1H$ NMR (500 MHz, CHLOROFORM-d): δ 5.61~5.68 (m, 1H), 5.45~5.55 (m, 1H), 4.61 (d, J=7.0 Hz, 2H), 2.30 (t, J=7.5 Hz, 2H), 2.20~2.24 (m, 7H), 2.06~2.13 (m, 2H), 1.59~1.64 (m, 2H), 1.33~1.42 (m, 5H), 1.21~1.30 (m, 35H), 0.88 (td, J=7.0, 3.0 Hz, 6H). MS (ESI) m/z: 494.3 [M+H]+.

Example 7: Synthesis of Lipid 7, (Z)-hept-2-en-1-yl 12-(2-(dimethylamino)ethyl)-henicosanoate

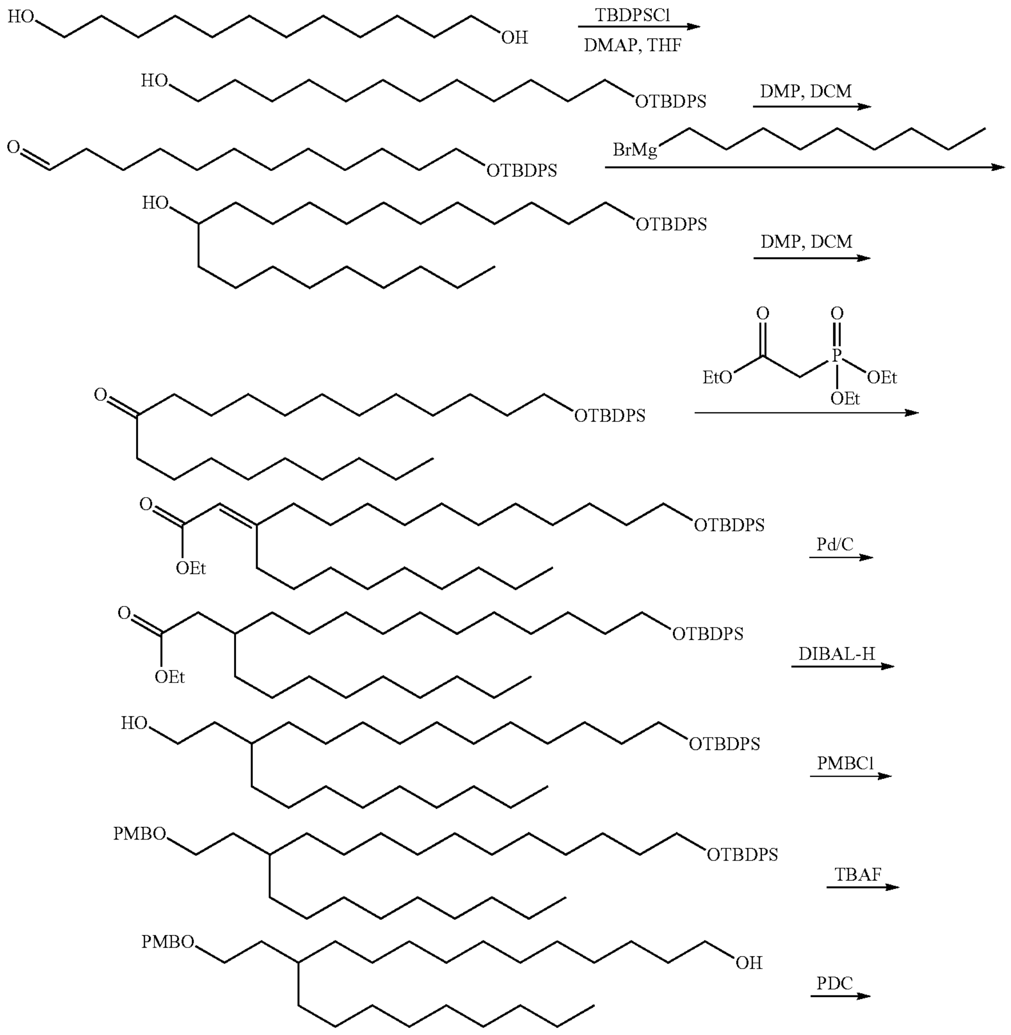

-continued

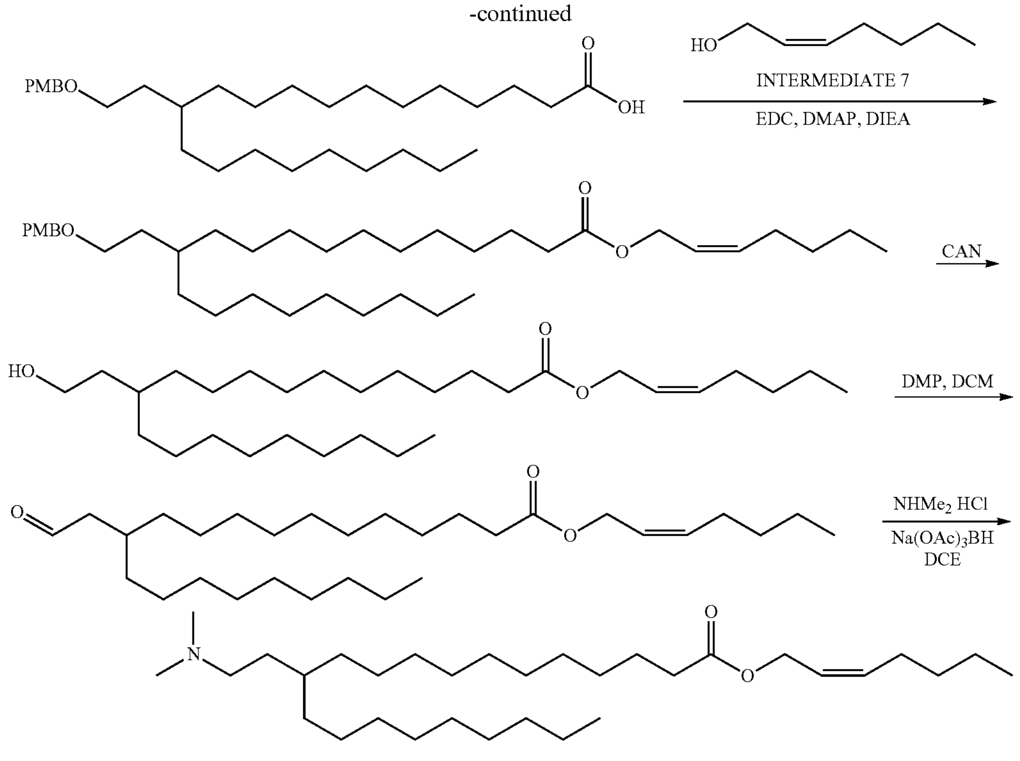

Lipid 7

Step 1: Synthesis of 12-((tert-butyldiphenylsilyl)oxy)dodecan-1-ol

To a solution of dodecane-1, 12-diol (15 g, 74.1 mmol) in THF (500 mL) was added imidazole (10.09 g, 148 mmol), DMAP (0.906 g, 7.41 mmol). Then TBDPSCl (18.09 mL, 70.4 mmol) was added to the above mixture at 0° C. and the reaction was heated to 25° C. and stirred for 16 h. The reaction was cooled to 0° C. and water (500 mL) was added. Then the resulting mixture was extracted with EtOAc (500 mL*2), combined organic layers, washed with brine (500 mL*2), dried over anhydrous $Na_2SO_4$, filtered and concentrated. The residue was purified by column chromatography ($SiO_2$, Pet. ether:EtOAc=20:1 to 5:1) to give 12-((tert-butyldiphenylsilyl)oxy)dodecan-1-ol (16 g, 32.7 mmol).

$^1$H NMR (400 MHz, CHLOROFORM-d): δ 7.66~7.72 (m, 4H), 7.36~7.42 (m, 6H), 3.63~3.66 (m, 4H), 1.55~1.70 (m, 4H), 1.20~1.31 (m, 16H), 1.04 (s, 9H).

Step 2: Synthesis of 12-((tert-butyldiphenylsilyl)oxy)dodecanal

To a solution of 12-((tert-butyldiphenylsilyl)oxy)dodecan-1-ol (27 g, 61.3 mmol) in DCM (500 mL) was added DMP (78 g, 184 mmol) at 0° C. The mixture was stirred at 15° C. for 4 h. The resulting mixture was diluted with ice water (500 mL), quenched with sat. $NaHCO_3$, the resulting mixture was filtered and the filtrate was extracted with DCM (1 L*2). The combined organic layers, washed with brine (2 L*2), were concentrated in vacuo, the residue was purified by column chromatography ($SiO_2$, Pet. ether:EtOAc=40:1 to 20:1) to give 12-((tert-butyldiphenylsilyl)oxy)dodecanal (16 g, 34.6 mmol).

$^1$H NMR (400 MHz, CHLOROFORM-d): δ 9.80 (s, 1H), 7.43~7.69 (m, 4H), 7.37~7.43 (m, 6H), 3.66 (t, J=6.4 Hz, 2H), 2.41~2.45 (m, 4H), 1.60~1.70 (m, 4H), 1.20~1.40 (m, 14H), 1.06 (s, 9H).

Step 3: Synthesis of 21-((tert-butyldiphenylsilyl)oxy)henicosan-10-ol

In a round-bottom flask, to a solution of fresh prepared nonylmagnesium bromide (100 mL, 58.0 mmol) was added 12-((tert-butyldiphenylsilyl)oxy)dodecanal (16 g, 36.5 mmol) at 0° C. The mixture was stirred at 15° C. for 1 h. The reaction mixture was quenched with sat. aq. $NH_4Cl$ (100 mL), extracted with EtOAc (100 mL*2), the combined organic layers were washed with brine (saturated, 200 mL*2) dried over anhydrous $Na_2SO_4$ filtered and concentrated. The reaction mixture was filtered and the solvent was concentrated in vacuo. The residue was purified by column chromatography ($SiO_2$, Pet. ether:EtOAc=20:1) to give 21-((tert-butyldiphenylsilyl)-oxy)henicosan-10-ol (17 g, 28.5 mmol).

$^1$H NMR (500 MHz, CHLOROFORM-d): δ 7.66~7.70 (m, 4H), 7.36~7.42 (m, 6H), 3.65 (t, J=6.5 Hz, 2H), 3.57~3.62 (m, 1H), 1.24~1.46 (m, 36H), 1.04 (s, 9H), 0.88 (t, J=6.5 Hz, 3H).

Step 4: Synthesis of 21-((tert-butyldiphenylsilyl)oxy)henicosan-10-one

To a solution of 21-((tert-butyldiphenylsilyl)oxy)henicosan-10-ol (29 g, 51.1 mmol) in DCM (500 mL) was added DMP (65.1 g, 153 mmol) at 0° C. The mixture was stirred at 25° C. for 6 h. The reaction mixture was quenched with sat. aq. $NH_4Cl$ (500 mL), extracted with EtOAc (500 mL*2), the combined organic layers were washed with brine (500 mL*2), dried over anh. $Na_2SO_4$ filtered and concentrated in vacuo. The reaction mixture was filtered and the solvent was concentrated under reduced pressure. The residue was purified by column chromatography ($SiO_2$, Pet. ether: EtOAc=20:1) to give 21-((tert-butyldiphenylsilyl)oxy)henicosan-10-one (22 g, 38.9 mmol).

$^1$H NMR (400 MHz, CHLOROFORM-d): δ 7.62~7.67 (m, 4H), 7.33~7.40 (m, 6H), 3.60 (t, J=6.8 Hz, 2H), 2.32~2.37 (m, 4H), 1.50~1.65 (m, 6H), 1.20~1.40 (m, 26H), 1.04 (s, 9H), 0.88 (t, J=6.5 Hz, 3H).

Step 5: Synthesis of (E)-ethyl 14-((tert-butyldiphenylsilyl)oxy)-3-nonyltetradec-2-enoate To a solution of ethyl 2-(diethoxyphosphoryl)acetate (23.81 g, 106 mmol) in THF (240 mL) was slowly added NaH (4.25 g, 106 mmol) at 0° C. under $N_2$ balloon. The reaction mixture was stirred at 15° C. for 0.5 h. Then the reaction mixture was slowly added 21-((tert-butyldiphenylsilyl)oxy)henicosan-10-one (12 g, 21.24 mmol) at 0° C. The reaction mixture was allowed to warm to 50° C. and stirred for 12 h. Then it was quenched with saturated aqueous $NH_4Cl$ (200 mL) at 0° C., and the resulting mixture was extracted EtOAc (200 mL*2). The combined organic extracts were washed with brine, dried over anhydrous $Na_2SO_4$, and filtered. The filtrate was concentrated in vacuo and the residue was purified by column chromatography ($SiO_2$, Pet. ether:EtOAc=50:1) to give (E)-ethyl 14-((tert-butyldiphenylsilyl)oxy)-3-nonyltetradec-2-enoate (12 g, 17.95 mmol).

$^1$H NMR (400 MHz, CHLOROFORM-d): δ 7.62~7.70 (m, 4H), 7.37~7.44 (m, 6H), 5.62 (s, 1H), 4.11~4.17 (m, 2H), 3.66 (t, J=6.5 Hz, 2H), 2.57~2.60 (m, 2H), 2.11~2.14 (m, 2H), 1.26~1.65 (m, 35H), 1.05 (s, 9H), 0.89 (t, J=6.5 Hz, 3H).

Step 6: Synthesis of ethyl 14-((tert-butyldiphenylsilyl)oxy)-3-nonyltetradecanoate To a solution of (E)-ethyl 14-((tert-butyldiphenylsilyl)oxy)-3-nonyltetradec-2-enoate (13 g, 20.47 mmol) in EtOAc (200 mL) was slowly added Pd/C (2.179 g, 20.47 mmol) at 20° C. under $N_2$ balloon. The reaction mixture was purged for 3 times under $H_2$ atmosphere, and then the mixture was warmed up to 20° C., and further stirred at 20° C. for 12 h. The reaction was filtered and the filtrate was concentrated in vacuo to give the crude product ethyl 14-((tert-butyldiphenylsilyl)oxy)-3-nonyltetradecanoate (12 g, 17.89 mmol), which was directly used for next step without further purification.

$^1$H NMR (500 MHz, CHLOROFORM-d): δ 7.66~7.71 (m, 4H), 7.35~7.47 (m, 6H), 4.08~4.18 (m, 2H), 3.64~3.68 (m, 2H), 2.22 (d, J=7.0 Hz, 2H), 1.22~1.43 (m, 39H), 1.06 (s, 9H), 0.88 (t, J=7.0 Hz, 3H).

Step 7: Synthesis of 14-((tert-butyldiphenylsilyl)oxy)-3-nonyltetradecan-1-ol To a solution of ethyl 14-((tert-butyldiphenylsilyl)oxy)-3-nonyltetradecanoate (12.5 g, 19.62 mmol) in THF (200 mL) was slowly added DIBAL-H (58.9 mL, 58.9 mmol) at 0° C. under $N_2$ balloon. The reaction mixture was stirred at 0° C. for 2 h. The mixture was quenched with sat. sodium potassium tartrate tetrahydrate solution (100 mL), and the mixture was stirred for 1 h, the mixture was extracted with EtOAc (200 mL*2), combined organic layers, washed with brine (1 L*2), organic layers was separated and dried over $Na_2SO_4$, filtered and the filtrate was concentrated. The residue was purified by column chromatography ($SiO_2$, Pet. ether:EtOAc=10:1) to give the product 14-((tert-butyldiphenylsilyl)oxy)-3-nonyltetradecan-1-ol (9.5 g, 15.17 mmol).

$^1$H NMR (400 MHz, CHLOROFORM-d): δ 7.60~7.70 (m, 4H), 7.37~7.44 (m, 6H), 3.64~3.73 (m, 4H), 1.50~1.58 (m, 4H), 1.21~1.45 (m, 35H), 1.05 (s, 9H), 0.90 (t, J=6.4 Hz, 3H).

Step 8: Synthesis of tert-butyl((12-(2-((4-methoxybenzyl)oxy)ethyl)henicosyl)oxy)-diphenylsilane To a solution of 14-((tert-butyldiphenylsilyl)oxy)-3-nonyltetradecan-1-ol (16 g, 26.9 mmol) in DMF (180 mL) was added TBAI (9.93 g, 26.9 mmol), NaH (6.45 g, 161 mmol) at 0° C., and the mixture was stirred at 0° C. for 30 min, then 1-(chloromethyl)-4-methoxybenzene (17.19 ml, 161 mmol) was added to the above mixture, then warmed to 30° C. and stirred for 2 h. Then the mixture was cooled to 0° C., quenched with sat. aq. $NH_4Cl$. (150 mL), then diluted with water (100 mL), extracted with EtOAc (300 mL*2), combined organic layers, washed with brine (500 mL*2), organic layer was dried over $Na_2SO_4$, filtered and the filtrate was concentrated in vacuo to give a residue, which was further purified by column chromatography ($SiO_2$, Pet. ether:EtOAc=100:1 to 80:1), to give the product tert-butyl ((12-(2-((4-methoxybenzyl)oxy)ethyl)henicosyl)oxy)diphenylsilane (10 g, 11.89 mmol).

$^1$H NMR (400 MHz. CHLOROFORM-d): δ 7.65~7.72 (m, 4H), 7.26~7.44 (m, 8H), 6.87~6.89 (m, 2H), 4.44 (s, 2H), 3.80 (s, 3H), 3.66 (t, J=6.4 Hz, 2H), 3.46 (t, J=6.8 Hz, 2H), 1.50~1.58 (m, 4H), 1.21~1.60 (m, 35H), 1.05 (s, 9H), 0.89 (t, J=6.4 Hz, 3H).

Step 9: Synthesis of 12-(2-((4-methoxybenzyl)oxy)ethyl)henicosan-1-ol

To a solution of tert-butyl((12-(2-((4-methoxybenzyl)oxy)ethyl)henicosyl)oxy)diphenylsilane (10 g, 11.89 mmol) in THF (50 mL) was added TBAF (50 mL, 50.0 mmol) at 20° C., and the mixture was stirred at 30° C. for 12 h. The reaction was diluted with water (100 mL), extracted with EtOAc (300 mL*2), combined organic layers, washed with brine (500 mL*2). The organic layers were dried over $Na_2SO_4$, filtered and the filtrate was concentrated in vacuo to give a residue, which was further purified by column chromatography ($SiO_2$, Pet. ether:EtOAc=5:1), to give the product 12-(2-((4-methoxybenzyl)oxy)ethyl)henicosan-1-ol (5.5 g, 10.96 mmol).

$^1$H NMR (500 MHz, CHLOROFORM-d): δ 7.24~7.29 (m, 2H), 6.84~6.91 (m, 2H), 4.44 (s, 2H), 3.81 (s, 3H), 3.65 (t, J=6.6 Hz, 2H), 3.46 (t, J=7.2 Hz, 2H), 1.51~1.64 (m, 4H), 1.17~1.48 (m, 35H), 0.89 (t, J=6.5 Hz, 3H).

Step 10: Synthesis of 12-(2-((4-methoxybenzyl)oxy)ethyl)henicosanoic Acid

To a solution of 12-(2-((4-methoxybenzyl)oxy)ethyl)henicosan-1-ol (5 g, 10.49 mmol) in DMF (90 mL) was added PDC (19.73 g, 52.4 mmol) at 0° C., and the mixture was stirred at 0° C. for 30 min, then warmed up to 30° C. and stirred for 12 h. Then the mixture was diluted with EtOAc (800 mL), filtered by column ($SiO_2$, EtOAc and THF), and then the filtrate was concentrated in vacuo to give the crude product 12-(2-((4-methoxybenzyl)oxy)ethyl)henicosanoic acid (5 g, 9.68 mmol), which was used in the subsequent step without further purification.

$^1$H NMR (400 MHz, CHLOROFORM-d): δ 7.25 (J=8.4 Hz, 2H), 6.86 (d, J=8.4 Hz, 2H), 4.42 (s, 2H), 3.80 (s, 3H), 3.44 (t, J=7.0 Hz, 2H), 2.33 (t, J=7.2 Hz, 2H), 1.55~1.66 (m, 4H), 1.12~1.45 (m, 33H), 0.87 (t, J=6.4 Hz, 3H).

Step 11: Synthesis of (Z)-hept-2-en-1-yl 12-(2-((4-methoxybenzyl)oxy)ethyl)henicosanoate To a solution of 12-(2-((4-methoxybenzyl)oxy)ethyl)henicosanoic acid (5.0 g, 10.19 mmol) in DCM (50 mL) was added (Z)-hept-2-en-1-ol (1.280 g, 11.21 mmol), EDC (3.91 g, 20.38 mmol), DMAP (1.245 g, 10.19 mmol), DIEA (7.12 ml, 40.8 mmol) at 0° C., then the mixture was warmed to 30° C., and the mixture was stirred at 30° C. for 12 h. The resulting mixture was directly purified by column chromatography ($SiO_2$, Pet. ether:EtOAc=20:1) to give the title product (Z)-hept-2-en-1-yl 12-(2-((4-methoxybenzyl)oxy)ethyl)henicosanoate (4 g, 6.47 mmol).

$^1$H NMR (400 MHz, CHLOROFORM-d): δ 7.25 (J=8.5 Hz, 2H), 6.87 (d, J=8.5 Hz, 2H), 5.51~5.67 (m, 2H), 4.62 (d, J=6.7 Hz, 2H), 4.42 (s, 2H), 3.80 (s, 3H), 3.45 (t, J=7.2 Hz, 2H), 2.30 (t, J=7.6 Hz, 2H), 2.10 (q, J=7.1 Hz, 2H), 1.54~1.62 (m, 4H), 1.12~1.45 (m, 37H), 0.86~0.91 (m, 6H).

Step 12: Synthesis of (Z)-hept-2-en-1-yl 12-(2-hydroxyethyl)henicosanoate

To a solution of (Z)-hept-2-en-1-yl 12-(2-((4-methoxybenzyl)oxy)ethyl)henicosanoate (1.0 g, 1.704 mmol) in ACN (8 mL) was added a water (2 mL) solution of CAN (3.74 g, 6.82 mmol) at 0° C., and then the mixture was warmed to 30° C. and further stirred for 2 h. The resulting mixture was quenched with sat. aq. $Na_2SO_3$ (10 mL) and ice water (20 mL) was added. The resulting mixture was extracted with EtOAc (30 mL*2), combined organic layers, washed with brine (50 mL*2), and the organic layers were dried over $Na_2SO_4$, filtered and the filtrate was concentrated in vacuum, the reside was purified by preparative TLC ($SiO_2$, Pet. ether:EtOAc=10:1) to give the title product (Z)-hept-2-en-1-yl 12-(2-hydroxyethyl)henicosanoate (0.7 g, 1.275 mmol).

$^1$H NMR (500 MHz, CHLOROFORM-d): δ 5.51~5.67 (m, 2H), 4.63 (d, J=7.0 Hz, 2H), 3.67 (t, J=7.0 Hz, 2H), 2.31 (t, J=7.0 Hz, 2H), 2.11 (q, J=7.1 Hz, 2H), 1.54~1.62 (m, 4H), 1.12~1.45 (m, 37H), 0.86~0.91 (m, 6H).

Step 13: Synthesis of (Z)-hept-2-en-1-yl 12-(2-oxoethyl)henicosanoate

To a solution of (Z)-hept-2-en-1-yl 12-(2-hydroxyethyl)henicosanoate (0.7 g, 1.275 mmol) in DCM (10 mL) solution was added DMP (1.622 g, 3.82 mmol) at 0° C., then the mixture was warmed to 30° C. and further stirred for 3 h, TLC showed the reaction was completed, the resulting mixture was quenched with sat. aq. $NaHCO_3$ (10 mL), ice water (20 mL) was diluted, the resulting mixture was extracted with DCM (30 mL*2), combined organic layers, washed with brine (50 mL*2), and organic layers were dried over $Na_2SO_4$. The reaction was filtered and the filtrate was concentrated in vacuo. The reside was purified by column chromatography ($SiO_2$, Pet. ether:EtOAc=40:1) to give the title product (Z)-hept-2-en-1-yl 12-(2-oxoethyl)henicosanoate (600 mg, 1.097 mmol).

$^1$H NMR (500 MHz, CHLOROFORM-d): δ 9.78 (s, 1H), 5.51~5.67 (m, 2H), 4.63 (d, J=6.7 Hz, 2H), 2.29~2.34 (m, 4H), 2.11 (q, J=7.1 Hz, 2H), 1.90~2.00 (m, 1H), 1.61~1.69 (m, 2H), 1.12~1.45 (m, 36H), 0.86~0.91 (m, 6H).

Step 14: Synthesis of (Z)-hept-2-en-1-yl 12-(2-(dimethylamino)ethyl)henicosanoate To a solution of (Z)-hept-2-en-1-yl 12-(2-oxoethyl)henicosanoate (450 mg, 0.968 mmol) in DCE (10 mL) solution was added dimethylamine hydrochloride (237 mg, 2.90 mmol), sodium triacetoxyhydroborate (616 mg, 2.90 mmol) at 0° C., then the mixture was warmed to 30° C. and further stirred for 12 h. The resulting mixture was quenched with ice water (20 mL) and diluted, and the resulting mixture was extracted with DCM (30 mL*2). The combined organic layers were washed with brine (50 mL*2), and organic layers was dried over $Na_2SO_4$. The reaction mixture was filtered and the filtrate was concentrated in vacuo. The reside was purified by preparative HPLC (YMC Actus Pro C18; Condition Isocratic 40% to 10% water (0.1% TFA)-ACN) to provide the monoester cationic lipid of Lipid 7, having a structure as set forth below:

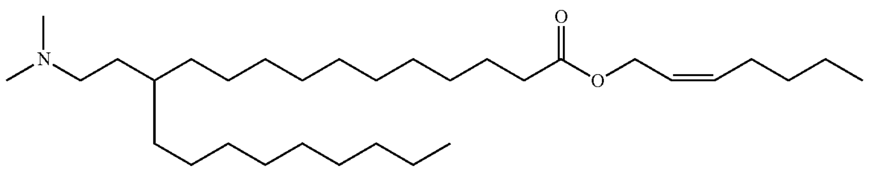 [SMILES: CCCC/C=C\COC(=O)CCCCCCCCCCC(CCCCCCCCC)CCN(C)C]

Lipid 7 i.e. (Z)-hept-2-en-1-yl 12-(2-(dimethylamino)ethyl)henicosanoate (300 mg, 0.607 mmol).

$^1$H NMR (500 MHz, CHLOROFORM-d): δ=5.51~5.67 (m, 2H), 4.63 (d, J=6.7 Hz, 2H), 2.98~3.02 (m, 2H), 2.82 (d, J=4.3 Hz, 6H), 2.31 (t, J=7.5 Hz, 2H), 2.11 (q, J=7.5 Hz, 2H), 1.60~1.70 (m, 4H), 1.12~1.45 (m, 37H), 0.85~0.92 (m, 6H). MS (ESI) m/z: 494.9 [M+H]+.

Example 8: Synthesis of Lipid 8, methyl (Z)-18-(2-(dimethylamino)-ethyl)heptacos-7-enoate
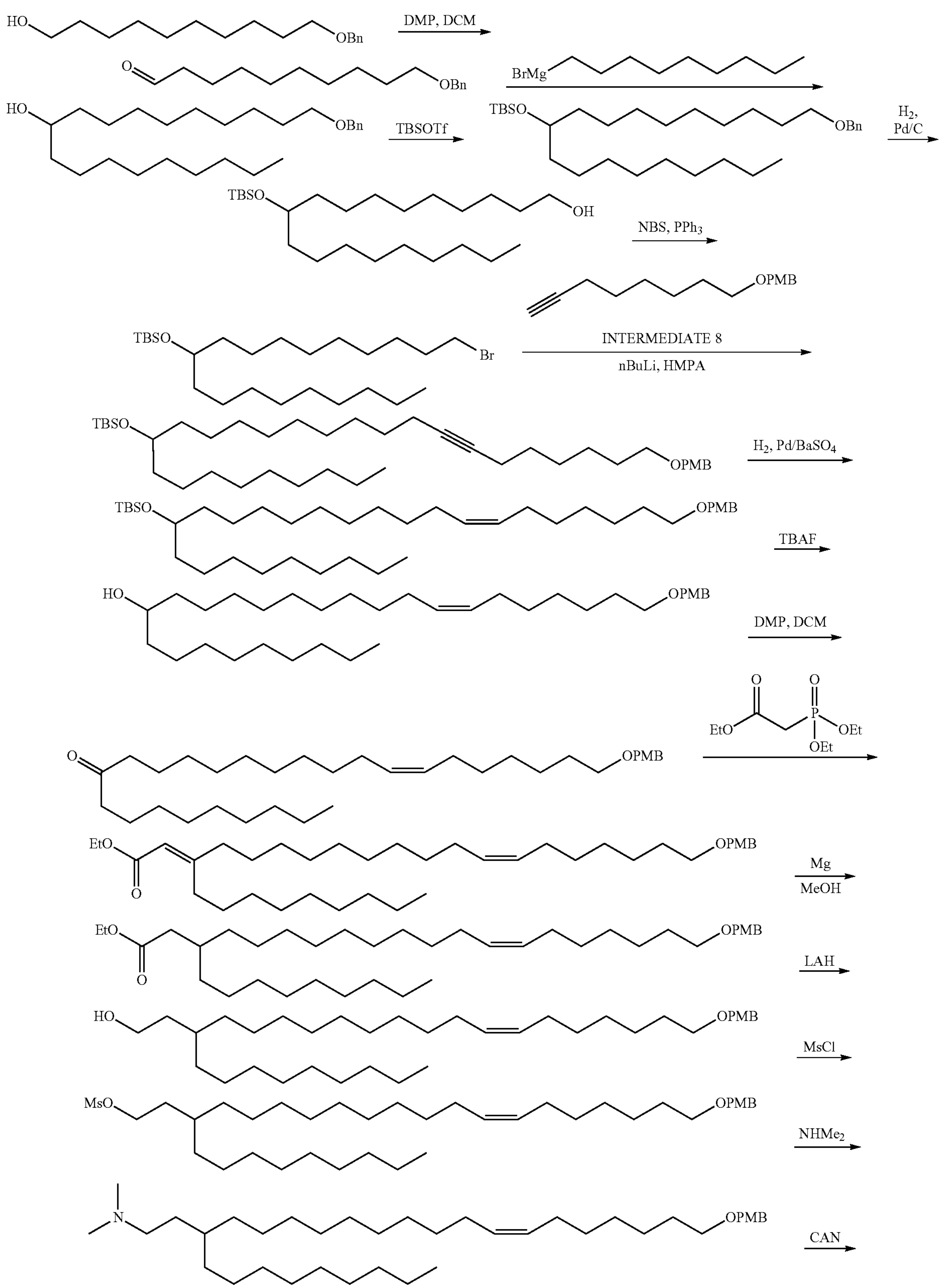

-continued

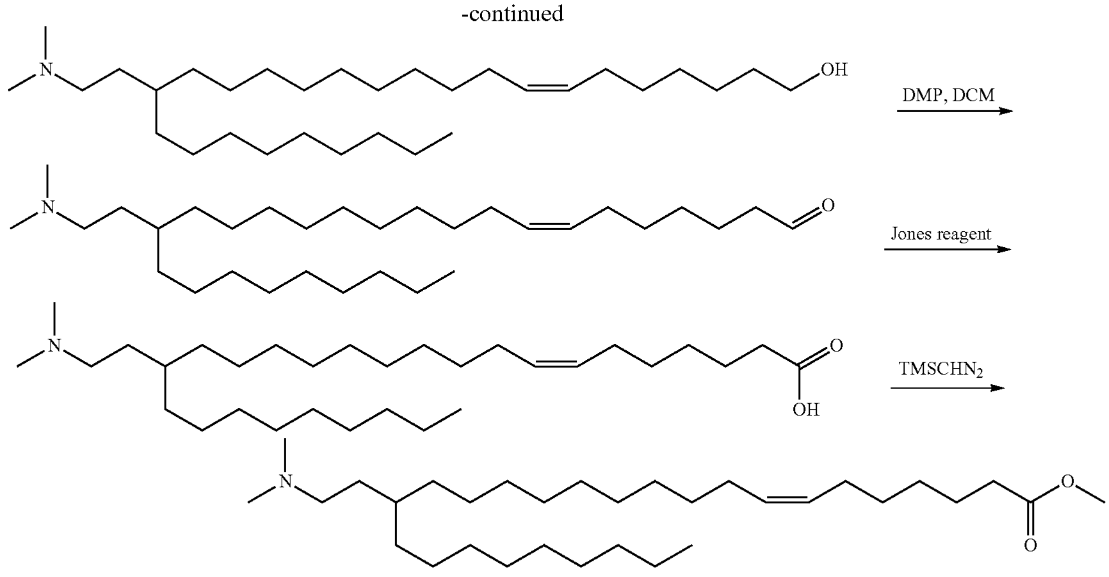

Lipid 8

Step 1: Synthesis of 10-(benzyloxy)decanal

In a round-bottom flask, to a solution of 10-(benzyloxy)decan-1-ol (10 g, 37.8 mmol) in DCM (100 mL) was added DMP (32.1 g, 76 mmol) in batch at 0° C. The mixture was stirred at 15° C. for 1.5 h. The reaction was quenched with sat. aq. $NaHCO_3$ solution (100 mL) and the resulting mixture was extracted with DCM (2*100 mL). The combined organic extracts were washed with brine, dried over anhydrous $Na_2SO_4$, and filtered. The residue was purified by column chromatography ($SiO_2$, Pet. ether:EtOAc=40:1) to give 10-(benzyloxy)decanal (6.6 g, 25.2 mmol).

$^1$H NMR (400 MHz, CHLOROFORM-d): δ=9.76 (s, 1H), 7.27~7.40 (m, 5H), 4.50 (s, 2H), 3.46 (t, J=6.4 Hz, 2H), 2.41 (dd, J=5.6 Hz, 7.2 Hz, 2H), 1.58~1.64 (m, 4H), 1.29~1.35 (m, 10H).

Step 2: Synthesis of 1-(benzyloxy)nonadecan-10-ol

To a solution of magnesium (14.52 g, 598 mmol) in THF (650 mL) was slowly added 1-bromononane (61.9 g, 299 mmol) in THF (50 mL) at 25° C. under $N_2$ balloon. The reaction mixture was allowed to warm to 40° C. and stirred for 2 h. Then the reaction mixture was cooled to 25° C. The solution was transferred to another bottle and 10-(benzyloxy)decanal (39.2 g, 149 mmol) in THF (50 mL) was added. The reaction mixture was stirred at 20° C. for 12 h. MeOH (250 mL) was added to mixture and the mixture was stirred at 25° C. for 10 h. The reaction was then quenched by the addition of 1 N HCl to adjust pH to 2~3. The resulting solution was extracted with EtOAc (3*200 mL) and the organic layers was dried over anhydrous $Na_2SO_4$, filtered and concentrated. The residue was purified by column chromatography ($SiO_2$, Pet. ether:EtOAc=10:1) to give 1-(benzyloxy)nonadecan-10-ol (40 g, 97 mmol).

$^1$H NMR (400 MHz, CHLOROFORM-d): δ=7.29~7.40 (m, 5H), 4.53 (s, 2H), 3.55~3.70 (m, 1H), 3.49 (t, J=6.8 Hz, 2H), 1.61~1.67 (m, 2H), 1.26~1.45 (m, 32H), 0.90 (t, J=6.8 Hz, 3H).

Step 3: Synthesis of ((1-(benzyloxy)nonadecan-10-yl)oxy)(tert-butyl)dimethylsilane tert-Butyldimethylsilyl trifluoromethanesulfonate (81 g, 307 mmol) was added dropwise to a solution of 2,6-dimethylpyridine (65.8 g, 614 mmol) and 1-(benzyloxy)nonadecan-10-ol (40 g, 102 mmol) in DCM (500 mL) at 20° C., then the reaction was stirred for 12 h at 20° C. Then the mixture was extracted with EtOAc (3*200 mL), washed with brine, and dried over $Na_2SO_4$. The mixture was filtered and concentrated in vacuo. The residue was purified by column chromatography ($SiO_2$, Pet. ether) to give ((1-(benzyloxy)-nonadecan-10-yl)oxy)(tert-butyl)dimethylsilane (48 g, 90 mmol).

$^1$H NMR (400 MHz, CHLOROFORM-d): δ=7.29~7.40 (m, 5H), 4.50 (s, 2H), 3.57~3.70 (m, 1H), 3.46 (t, J=7.2 Hz, 2H), 1.59~1.64 (m, 2H), 1.26~1.40 (m, 32H), 0.87~0.89 (m, 12H), 0.05 (s, 6H).

Step 4: Synthesis of 10-((tert-butyldimethylsilyl)oxy)nonadecan-1-ol

A mixture of ((1-(benzyloxy)nonadecan-10-yl)oxy)(tert-butyl)dimethylsilane (47 g, 93 mmol), Pd/C (cat.), and EtOAc (500 mL) was stirred for 16 h at 50° C. under $H_2$ atmosphere (50 psi). Then the mixture was concentrated in vacuo to give 10-((tert-butyldimethylsilyl)oxy)nonadecan-1-ol (38 g, 87 mmol), which was used directly in the subsequent step without further purification.

$^1$H NMR (400 MHz, CHLOROFORM-d): δ=3.58~3.63 (m, 3H), 1.20~1.40 (m, 32H), 0.75~0.90 (m, 12H), 0.02 (s, 6H).

Step 5: Synthesis of ((1-bromononadecan-10-yl)oxy)(tert-butyl)dimethylsilane

A solution of 10-((tert-butyldimethylsilyl)oxy)nonadecan-1-ol (10 g, 24.11 mmol) and triphenylphosphine (9.49 g, 36.2 mmol) in DCM (150 mL) was added 1-bromopyrrolidine-2,5-dione (5.58 g, 31.3 mmol). The mixture was stirred at 25° C. for 1 h. The reaction mixture was diluted with DCM, dried over $Na_2SO_4$, filtered, and concentrated in vacuo. The residue was purified by column chromatography ($SiO_2$, Pet. ether) to give ((1-bromononadecan-10-yl)oxy)(tert-butyl)dimethylsilane (12 g, 23.87 mmol).

Step 6: Synthesis of tetraethyl tert-butyl((27-((4-methoxybenzyl)oxy)heptacos-20-yn-10-yl)oxy)dimethylsilane n-Butyllithium (5.02 mL, 12.56 mmol) was added dropwise to a solution of 1-methoxy-4-((oct-7-yn-1-yloxy)methyl)benzene (2.58 g, 10.47 mmol) in THF (50 mL) at −60° C., then the reaction was allowed to warm to −20° C. for 30 min. HMPA (10 mL) was added dropwise followed by ((1-bromononadecan-10-yl)oxy)(tert-butyl)dimethylsilane (5 g, 10.47 mmol). The reaction was stirred for 5 h at 0° C., and then warmed to 20° C. for an additional 14 h. Then reaction was quenched with sat. aq. $NH_4Cl$ and extracted into EtOAc (3*100 mL), washed with brine, dried over $Na_2SO_4$, filtered, and concentrated in vacuo. The residue was purified by column chromatography ($SiO_2$, Pet. ether: EtOAc=10:1) to give tetraethyl tert-butyl((27-((4-methoxybenzyl)oxy)heptacos-20-yn-10-yl)oxy)dimethylsilane (3.9 g, 5.76 mmol).

$^1$H NMR (400 MHz, CHLOROFORM-d): δ=7.22 (d, J=6.8 Hz, 2H), 6.84 (d, J=6.8 Hz, 2H), 4.39 (s, 2H), 3.77 (s, 3H), 3.54~3.59 (m, 1H), 3.40 (t, J=6.4 Hz, 2H), 2.10 (t, J=6.0 Hz, 2H), 1.22~1.60 (m, 42H), 0.85 (m, 12H), 0.00 (s, 6H).

Step 7: Synthesis of (Z)-tert-butyl((27-((4-methoxybenzyl)oxy)heptacos-20-en-10-yl)oxy)dimethylsilane In a round-bottom flask, to a solution of tert-butyl((27-((4-methoxybenzyl)oxy)heptacos-20-yn-10-yl)oxy)dimethylsilane (1.8 g, 2.80 mmol) in pyridine (50 mL) was added Lindlar Catalyst (180 mg, 0.085 mmol) at 15° C. The mixture was stirred at $H_2$ for 10 h. Then the reaction was filtrated and concentrated to give (Z)-tert-butyl((27-((4-methoxybenzyl)oxy)heptacos-20-en-10-yl)oxy)dimethylsilane (1.8 g, 2.79 mmol), which was used in the subsequent step without further purification.

$^1$H NMR (400 MHz, CHLOROFORM-d): δ=7.28 (d, J=8.8 Hz, 2H), 6.88 (d, J=8.8 Hz, 2H), 5.36 (s, 2H), 4.44 (s, 2H), 3.81 (s, 3H), 3.58~3.65 (m, 1H), 3.44 (t, J=6.4 Hz, 2H), 2.00~2.02 (m, 4H), 1.20~1.40 (m, 40H), 0.87~0.89 (m, 12H), 0.04 (s, 6H).

Step 8: Synthesis of (Z)-27-((4-methoxybenzyl)oxy)heptacos-20-en-10-ol

In a round-bottom flask, to (Z)-tert-butyl((27-((4-methoxybenzyl)-oxy)heptacos-20-en-10-yl)oxy)dimethylsilane (1.8 g, 2.79 mmol) was added TBAF (8.37 mL, 8.37 mmol) at 20° C. The mixture was stirred at 50° C. for 16 h. The reaction was concentrated, water (20 mL) was added to the residue and it was extracted with EtOAc (20 mL*3), washed with brine, dried over anhydrous $Na_2SO_4$, filtrated and concentrated in vacuo. The residue was purified by column chromatography ($SiO_2$, Pet. ether:EtOAc=20:1 to 1:1) to give (Z)-27-((4-methoxybenzyl)oxy)heptacos-20-en-10-ol (1.3 g, 2.449 mmol).

$^1$H NMR (400 MHz, CHLOROFORM-d): δ=7.28 (d, J=8.8 Hz, 2H), 6.88 (d, J=8.8 Hz, 2H), 5.35 (s, 2H), 4.44 (s, 2H), 3.81 (s, 3H), 3.55~3.63 (m, 1H), 3.44 (t, J=6.4 Hz, 2H), 2.00~2.02 (m, 4H), 1.20~1.40 (m, 40H), 0.89 (t, J=6.8 Hz, 3H).

Step 9: Synthesis of (Z)-27-((4-methoxybenzyl)oxy)heptacos-20-en-10-one

In a round-bottom flask, to a solution of (Z)-27-((4-methoxybenzyl)oxy)heptacos-20-en-10-ol (1.3 g, 2.449 mmol) in DCM (20 mL) was added DMP (3.12 g, 7.35 mmol) at 0° C. The mixture was stirred at 20° C. for 2 h. The reaction was filtered. The filtrate was quenched with sat. aq. $NaHCO_3$ (50 mL) and it was filtered again. Then the resulting mixture was extracted with DCM (20 mL*2). The combined organic extracts were washed with brine, dried over anhydrous $Na_2SO_4$, filtered, and concentrated in vacuo. The residue was purified by column chromatography ($SiO_2$, Pet. ether:EtOAc=80:1) to give (Z)-27-((4-methoxybenzyl)oxy)heptacos-20-en-10-one (1.1 g, 2.080 mmol).

$^1$H NMR (400 MHz, CHLOROFORM-d): δ=7.28 (d, J=8.8 Hz, 2H), 6.88 (d, J=8.8 Hz, 2H), 5.35 (d, J=5.2 Hz, 2H), 2.02 (s, 2H), 3.81 (s, 3H), 3.44 (t, J=6.8 Hz, 2H), 2.38 (t, J=7.2 Hz, 4H), 2.00~2.02 (m, 4H), 1.20~1.40 (m, 36H), 0.88 (t, J=6.8 Hz, 3H).

Step 10: Synthesis of (2E,13Z)-ethyl 20-((4-methoxybenzyl)oxy)-3-nonylicosa-2,13-dienoate To a solution of ethyl 2-(diethoxyphosphoryl)acetate (4.66 g, 20.80 mmol) in THF (11 mL) was slowly added NaH (0.832 g, 20.80 mmol) at 0° C. under $N_2$ balloon. The reaction mixture was stirred at 15° C. for 0.5 h. Then t (Z)-27-((4-methoxybenzyl)oxy)heptacos-20-en-10-one (1.1 g, 2.080 mmol) was slowly added to the reaction mixture at 0° C. The reaction mixture was warmed to 55° C. and stirred for 12 h. The reaction was quenched with water (100 mL) at 0° C., and the resulting mixture was extracted EtOAc (100 mL*2). The combined organic extracts were washed with water and brine (100 mL*2), dried over anhydrous $Na_2SO_4$, and filtered. The filtrate was concentrated in vacuo and the residue was purified by column chromatography ($SiO_2$, Hexanes:EtOAc=50:1) to give (2E,13Z)-ethyl 20-((4-methoxybenzyl)oxy)-3-nonylicosa-2,13-dienoate (1.1 g, 1.837 mmol).

$^1$H NMR (400 MHz, CHLOROFORM-d): δ=7.28 (d, J=8.8 Hz, 2H), 6.88 (d, J=8.8 Hz, 2H), 5.61 (s, 1H), 5.36 (s, 2H), 4.44 (s, 2H), 4.14 (q, J=6.8 Hz, 2H), 3.81 (s, 3H), 3.44 (t, J=6.4 Hz, 2H), 2.58 (t, J=8.0 Hz, 2H), 2.12 (t, J=8.0 Hz, 2H), 1.90~2.05 (m, 4H), 1.25~1.50 (m, 39H), 0.86~0.90 (m, 3H). MS (ESI) m/z: 621.5 [M+Na]*.

Step 11: Synthesis of (Z)-methyl 20-((4-methoxybenzyl)oxy)-3-nonylicos-13-enoate A mixture of (2E,13Z)-ethyl 20-((4-methoxybenzyl)oxy)-3-nonylicosa-2,13-dienoate (50 mg, 5 mmol), Mg (81 mg, 3.34 mmol) and MeOH (5 mL) was warmed to 70° C. The reaction mixture was stirred at 70° C. for 2 h. The resulting mixture was quenched with water (20 mL), extracted with DCM (10 mL*3), washed with brine (20 mL), dried over $Na_2SO_4$, and filtered. The filtrate was concentrated in vacuo to give (Z)-methyl 20-((4-methoxybenzyl)oxy)-3-nonylicos-13-enoate (44 mg), which was used in the subsequent step without further purification.

$^1$H NMR (400 MHz, CHLOROFORM-d): δ=7.27 (d, J=8.8 Hz, 2H), 6.87 (d, J=8.8 Hz, 2H), 5.33~5.38 (m, 2H), 4.23 (s, 2H), 3.80 (s, 3H), 3.67 (s, 3H), 3.42 (t, J=6.8 Hz, 2H), 2.22 (d, J=6.8 Hz, 2H), 2.00~2.10 (m, 4H), 1.25~1.40 (m, 43H), 0.88 (t, J=6.8 Hz, 3H).

Step 12: Synthesis of (Z)-20-((4-methoxybenzyl)oxy)-3-nonylicos-13-en-1-ol

A mixture of (Z)-methyl 20-((4-methoxybenzyl)oxy)-3-nonylicos-13-enoate (2.8 g, 4.67 mmol), LAH (1.77 g, 46.75 mmol) and THF (15 mL) was stirred at 0° C. Then the mixture was stirred at 0° C. for 2 h. The resulting mixture was quenched with water (20 mL), extracted with DCM (10 mL*3), washed with brine (20 mL), dried over $Na_2SO_4$, and filtered. The filtrate was concentrated in vacuo to give (Z)-20-((4-methoxybenzyl)oxy)-3-nonylicos-13-en-1-ol (2.5 g), which was used in the subsequent step without further purification.

$^1$H NMR (400 MHz, CHLOROFORM-d): δ=7.26 (d, J=8.8 Hz, 2H), 6.87 (d, J=8.8 Hz, 2H), 5.30~5.35 (m, 2H), 4.43 (s, 2H), 3.80 (s, 3H), 3.66 (d, J=7.2 Hz, 2H), 3.43 (t, J=6.4 Hz, 2H), 1.90~2.00 (m, 5H), 1.19~1.52 (m, 43H), 0.88 (t, J=6.8 Hz, 3H).

Step 13: Synthesis of (Z)-20-((4-methoxybenzyl)oxy)-3-nonylicos-13-en-1-yl methanesulfonate A mixture of (Z)-20-((4-methoxybenzyl)oxy)-3-nonylicos-13-en-1-ol (2.4 g, 4.1 mmol), MsCl (1.41 g, 12.31 mmol) and Et3N (2.18 g, 21.55 mmol) and THF (15 mL) was stirred at 0° C. Then the mixture was stirred at 0° C. for 2 h. The resulting mixture was quenched with water (20 mL) and stirred at 0° C. for 2 h. The resulting mixture was diluted with water (20 mL), extracted with DCM (20 mL*3), washed with brine (20 mL), dried over $Na_2SO_4$, and filtered. The filtrate was concentrated in vacuo to give (Z)-20-((4-methoxybenzyl)oxy)-3-nonylicos-13-en-1-yl methanesulfonate (2.6 g), which was used in the subsequent step without further purification.

$^1$H NMR (400 MHz, CHLOROFORM-d): δ=7.27 (d, J=8.8 Hz, 2H), 6.87 (d, J=8.8 Hz, 2H), 5.32~5.34 (m, 2H), 4.23 (s, 2H), 4.24 (t, J=6.4 Hz, 1H), 3.80 (s, 3H), 3.43 (t, J=6.8 Hz, 2H), 3.00 (s, 3H), 2.00~2.10 (m, 4H), 1.25~1.40 (m, 42H), 0.88 (t, J=6.8 Hz, 3H).

Step 14: Synthesis of (Z)-20-((4-methoxybenzyl)oxy)-N,N-dimethyl-3-nonylicos-13-en-1-amine A mixture of (Z)-20-((4-methoxybenzyl)oxy)-3-nonylicos-13-en-1-yl methanesulfonate (2.4 g, 3.77 mmol) and $NHMe_2$ (29.25 g, 20% in THF, 188.38 mmol) was stirred at 0° C. Then the mixture was warmed to 30° C. and stirred for 20 h. The resulting mixture was concentrated in vacuo to give (Z)-20-((4-methoxybenzyl)oxy)-N,N-dimethyl-3-nonylicos-13-en-1-amine (2.0 g), which was used in the subsequent step without further purification.

$^1$H NMR (400 MHz, CHLOROFORM-d): δ=7.25 (d, J=8.8 Hz, 2H), 6.87 (d, J=8.8 Hz, 2H), 5.34 (s, 2H), 4.43 (s, 2H), 3.80 (s, 3H), 3.42 (t, J=6.4 Hz, 2H), 2.23~2.28 (m, 8H), 1.80~2.10 (m, 5H), 1.20~1.40 (m, 42H), 0.87 (t, J=6.8 Hz, 3H).

Step 15: Synthesis of (Z)-18-(2-(dimethylamino)ethyl)heptacos-7-en-1-ol

A mixture of (Z)-20-((4-methoxybenzyl)oxy)-N,N-dimethyl-3-nonylicos-13-en-1-amine (1.9 g, 3.24 mmol), ACN (40 mL) and water (5 mL) was stirred at 30° C. Then CAN (5.4 g, 12.97 mmol) was added in portions. The mixture was stirred at 30° C. for 4 h. The reaction mixture was quenched with sat. $NH_4Cl$ and concentrated in vacuo. The residue was by column chromatography ($SiO_2$, EtOAc) to give (Z)-18-(2-(dimethylamino)ethyl)heptacos-7-en-1-ol (2.0 g).

$^1$H NMR (400 MHz, CHLOROFORM-d): δ=5.26~5.31 (m, 2H), 3.56 (t, J=6.8 Hz, 2H), 2.17~2.20 (m, 8H), 1.80~2.00 (m, 4H), 1.15~1.30 (m, 43H), 0.81 (t, J=6.8 Hz, 3H).

Step 16: Synthesis of (Z)-18-(2-(dimethylamino)ethyl)heptacos-7-enal

A mixture of (Z)-18-(2-(dimethylamino)ethyl)heptacos-7-en-1-ol (200 mg, 0.429 mmol), DMP (364 mg, 0.859 mmol) and DCM (10 mL) was stirred at 30° C. for 2 h. Then reaction mixture was filtered, concentrated in vacuo, and purified with preparative TLC (DCM:MeOH=10:1) to give (Z)-18-(2-(dimethylamino)ethyl)heptacos-7-enal (200 mg, 0.345 mmol).

$^1$H NMR (400 MHz, CHLOROFORM-d): δ=5.26~5.39 (m, 2H), 2.42 (t, J=7.6 Hz, 2H), 2.20~2.30 (m, 10H), 1.80~2.10 (m, 6H), 1.15~1.30 (m, 37H), 0.88 (t, J=6.8 Hz, 3H).

Step 17: Synthesis of (Z)-18-(2-(dimethylamino)ethyl)heptacos-7-enoic Acid

The (Z)-18-(2-(dimethylamino)ethyl)heptacos-7-enal (1.5 g, 3.23 mmol) was dissolved in acetone (2 mL) and cooled to 0° C. Jones reagent (50 mg, 0.500 mmol), and water (0.4 mL) were added, and sulfuric acid (50 mg, 0.510 mmol) was added dropwise. The reaction was warmed to 30° C. and stirred for 1 h. The reaction mixture was purified directly by preparative HPLC to give (Z)-18-(2-(dimethylamino)ethyl)heptacos-7-enoic acid (500 mg, 0.834 mmol) as a clear oil. MS (ESI) m/z: 480.5 $[M+H]^+$.

Step 18: Synthesis of (Z)-methyl 18-(2-(dimethylamino)ethyl)heptacos-7-enoate (Z)-18-(2-(dimethylamino)ethyl)heptacos-7-enoic acid (500 mg, 1.042 mmol) was dissolved in DCM (10 mL) and MeOH (1.00 mL). (Diazomethyl)trimethylsilane (2.61 mL, 5.21 mmol) was added to the reaction mixture. The reaction was warmed to 30° C. and stirred for 16 h. The reaction mixture was concentrated in vacuo and the resulting residue was purified directly by preparative HPLC (acid) to provide the monoester cationic lipid of Lipid 8, having a structure as set forth below:

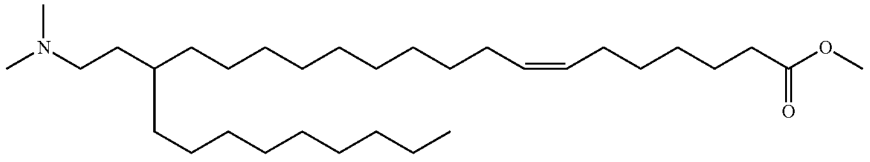

Lipid 8 i.e. (Z)-methyl 18-(2-(dimethylamino)ethyl)heptacos-7-enoate (388.70 mg, 0.787 mmol).

$^{1}$H NMR (400 MHz, CHLOROFORM-d): δ=5.26~5.39 (m, 2H), 3.65 (s, 3H), 3.12 (t, J=7.6 Hz, 2H), 2.88 (s, 6H), 2.31 (t, J=7.2 Hz, 2H), 1.95~2.10 (m, 5H), 1.58~1.67 (m, 4H), 1.30~1.40 (m, 36H), 0.90 (t, J=6.8 Hz, 3H). MS (ESI) m/z: 494.5 [M+H]$^{+}$.

Example 9: Preparation of Lipid Nanoparticle Compositions

The lipid nanoparticle (LNP) compositions of Table II were prepared as described in detail below.

TABLE II

| LNP Number* | Cationic Lipid Structure | Chemical Name |
|---|---|---|
| 1 | 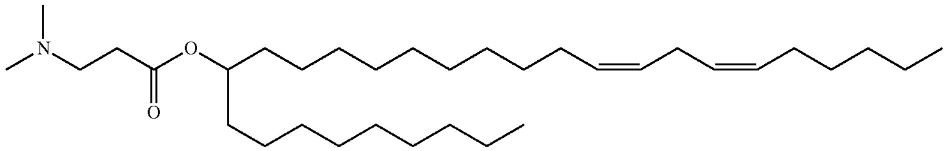 [SMILES: CCCCC/C=C\C/C=C\CCCCCCCCCC(CCCCCCCCC)OC(=O)CCN(C)C] | (20Z, 23Z)-nonacosa-20,23-dien-10-yl 3-(dimethylamino)-propanoate |
| 2 | 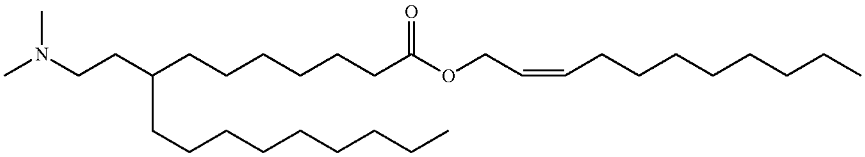 [SMILES: CCCCCCCC/C=C\COC(=O)CCCCCCC(CCCCCCCCC)CCN(C)C] | (Z)-undec-2-en-1-yl 8-(2-(dimethylamino) ethyl) heptadecanoate |
| 3 | 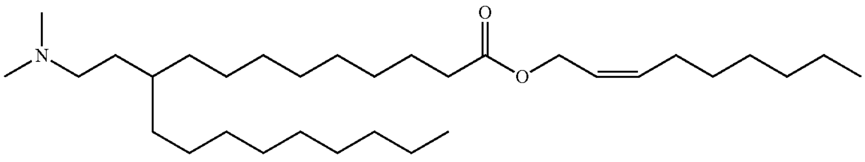 [SMILES: CCCCCC/C=C\COC(=O)CCCCCCCCC(CCCCCCCCC)CCN(C)C] | (Z)-non-2-en-1-yl 10-(2-(dimethylamino) ethyl) nonadecanoate |
| 4 | 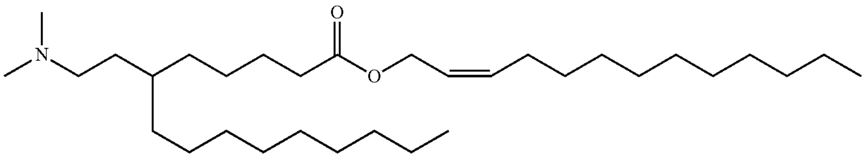 [SMILES: CCCCCCCCCC/C=C\COC(=O)CCCCC(CCCCCCCCC)CCN(C)C] | (Z)-tridec-2-en-1-yl 6-(2-(dimethylamino) ethyl) pentadecanoate |
| 5 | 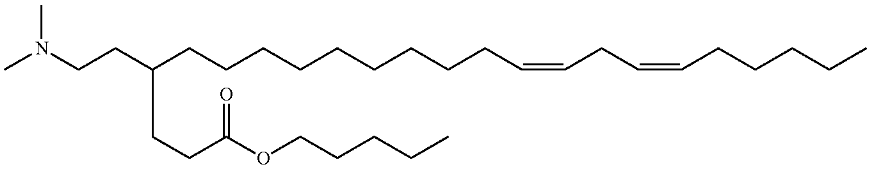 [SMILES: CCCCC/C=C\C/C=C\CCCCCCCCCC(CCC(=O)OCCCCC)CCN(C)C] | pentyl (14Z, 17Z)-4-(2-(dimethylamino) ethyl) tricosa-14,17-dienoate |

TABLE II-continued

| LNP Number* | Cationic Lipid Structure | Chemical Name |
|---|---|---|
| 6 | 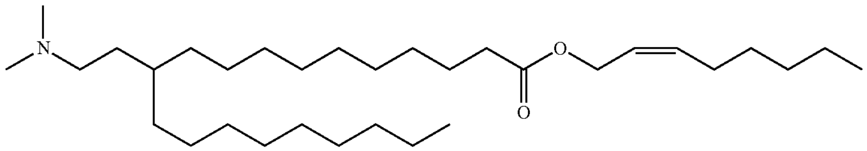 [SMILES: CCCCC/C=C\COC(=O)CCCCCCCCCC(CCCCCCCCC)CCN(C)C] | (Z)-oct-2-en-1-yl 11-(2-(dimethylamino)ethyl)icosanoate |
| 7 | 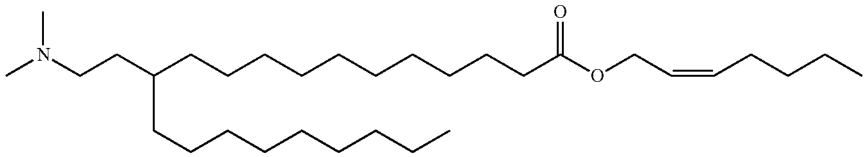 [SMILES: CCCC/C=C\COC(=O)CCCCCCCCCCC(CCCCCCCCC)CCN(C)C] | (Z)-hept-2-en-1-yl 12-(2-(dimethylamino)ethyl)henicosanoate |
| 8 | 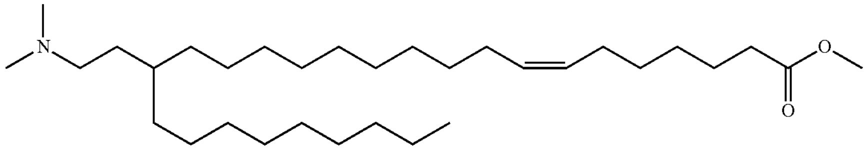 | methyl (Z)-18-(2-(dimethylamino)ethyl)heptacos-7-enoate |
| 9 | 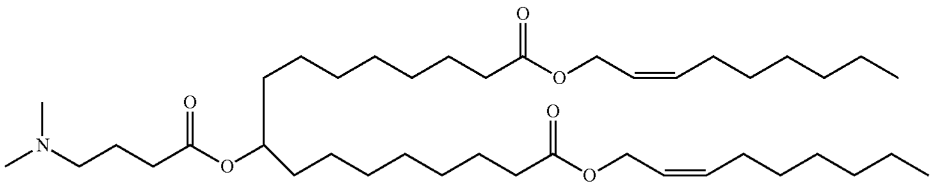 [SMILES: CCCCCC/C=C\COC(=O)CCCCCCCC(CCCCCCCC(=O)OC/C=C\CCCCCC)OC(=O)CCCN(C)C] | di((Z)-non-2-en-1-yl) 9-((4-(dimethylamino)butanoyl)oxy)heptadecanedioate |
| 10 | 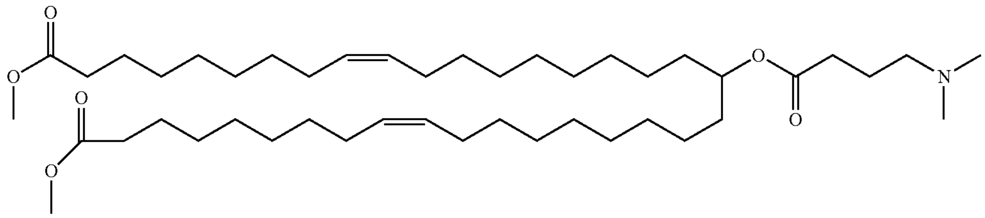 [SMILES: COC(=O)CCCCCCC/C=C\CCCCCCCCC(CCCCCCCC/C=C\CCCCCCCC(=O)OC)OC(=O)CCCN(C)C] | dimethyl (9Z,28Z)-19-((4-(dimethylamino)butanoyl)oxy)heptatriaconta-9,28-dienedioate |
| 11 | 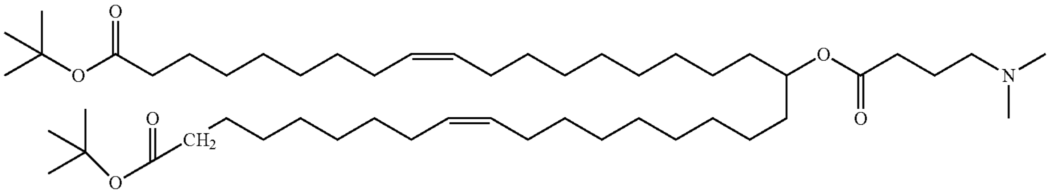 [SMILES: CN(C)CCCC(=O)OC(CCCCCCCC/C=C\CCCCCCCC(=O)OC(C)(C)C)CCCCCCCC/C=C\CCCCCCCC(=O)OC(C)(C)C] | di-tert-butyl (9Z,28Z)-19-((4-(dimethylamino)butanoyl)oxy) |

TABLE II-continued

| LNP Number* | Cationic Lipid Structure | Chemical Name |
|---|---|---|
| | | heptatriaconta-9,28-dienedioate |
| 12 | 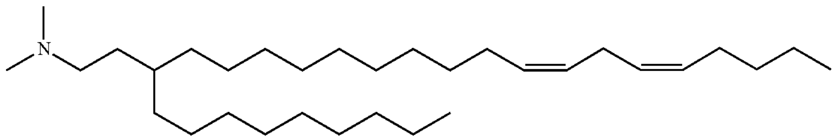 [SMILES: CCCC/C=C\C/C=C\CCCCCCCCCC(CCCCCCCCC)CCN(C)C] | (13Z,16Z)-N,N-dimethyl-3-nonyldocosa-13,16-dien-1-amine |
| 13 | 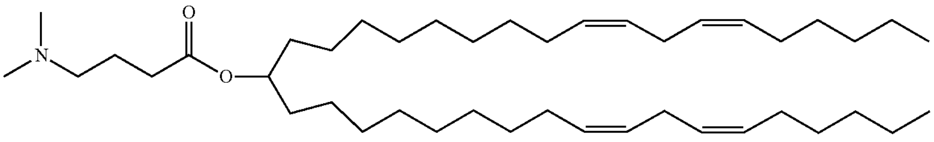 [SMILES: CCCCC/C=C\C/C=C\CCCCCCCCC(CCCCCCCC/C=C\C/C=C\CCCCC)OC(=O)CCCN(C)C] | (6Z,9Z,28Z,31Z)-heptatriaconta-6,9,28,31-tetraen-19-yl 4-(dimethylamino)butanoate |

*All LNP compositions consisted of cationic lipid (as indicated in Table II), plus cholesterol, a DSPC (1,2-Distearoyl-sn-glycero-3-phosphocholine), and a PEG- lipid (α-[8'-(1,2-Dimyristoyl-3-propanoxy)-carboxamide-3',6'-Dioxaoctanyl]carbamoyl-ω-methyl-poly(ethylene glycol), also known as PEG2000-DMG) at molar ratio of 58:30:10:2, respectively.

Process of Making Lipid Nanoparticle Composition

LNP compositions of the present invention were made according to the following method. First, the lipid components were dissolved in ethanol to form an organic solution. The lipid/ethanol solution was mixed with an aqueous solution of mRNA dissolved in a sodium citrate buffered salt solution having a pH of about 2-6 using a confined volume mixing T-mixer.

The organic and aqueous solutions were delivered to the inlet of the T-mixer using programmable syringe pumps and with a total flow rate from 10 mL/min-600 L/minute. The aqueous and organic solutions were combined with a ratio in the range of about 1:1 to 4:1 vol:vol. Mixing of the lipid/ethanal and mRNA/aqueous solutions forms the LNP. The resulting LNP suspension was twice diluted with a citrate buffered solution having a pH of about 6-8 in a sequential, in-line mixing process. For the first dilution, the LNP suspension was mixed with a buffered solution having a pH of about 6-7.5 and a mixing ratio in the range of about 1:1 to 1:3 vol:vol. The resulting LNP suspension was further mixed with a buffered solution having a pH of about 6-8 and a mixing ratio in the range of 1:1 to 1:3 vol:vol.

The LNPs were then concentrated and filtered via an ultrafiltration process where the alcohol was removed and the buffer exchanged for the final buffer solution. The ultrafiltration process, having a tangential flow filtration format ("TFF"), used a hollow fiber membrane nominal molecular weight cutoff range from 30-500 KD, targeting 100 KD. The TFF retained the LNP in the retentate and the filtrate or permeate contained the alcohol and final buffer wastes. The TFF provided an initial concentration to a lipid concentration of 20-100 mg/mL.

Following concentration, the LNP suspension was diafiltered against the final buffer with pH 7-8, 10 mM Tris, 140 mM NaCl with pH 7-8, or 10 mM Tris, 70 mM NaCl, 5-10 wt % sucrose, with pH 7-8, for 5-20 volumes to remove the alcohol and perform buffer exchange. The material was then concentrated via ultrafiltration.

The concentrated LNP suspension was then sterile filtered into a suitable container under aseptic conditions. Sterile filtration was accomplished by passing the LNP suspension through a pre-filter (Acropak 500 PES 0.45/0.8μιη capsule) and a bioburden reduction filter (Acropak 500 PES 0.2/0.8μιη capsule). Following filtration, the vialed LNP product was stored −20° C.

Example 10: In Vivo Evaluation of SEAP mRNA LNP Compositions with Different Cationic Lipid Components Female Balb/C (CRL) mice (6-8 weeks old; N=10 mice per group) were given 100 μl intramuscular (IM, 50 μl per quad) injections of secreted placental alkaline phosphatase ("SEAP") mRNA formulated in LNPs (i.e., mRNA-LNPs). mRNA-LNPs were prepared by the process described in Example 9, with LNP compositions as indicated in Table II above.

As shown in Table III, Groups 1-4 compare LNP 9, LNP 10, LNP 11 and LNP 13 at a dose of 1.0 μg SEAP mRNA.

TABLE III

| Group | SEAP mRNA (μg) | LNP Number |
|---|---|---|
| 1 | 1.0 | 9 |
| 2 | 1.0 | 10 |
| 3 | 1.0 | 11 |
| 4 | 1.0 | 13 |

Animals were inoculated once. On day 1, blood was drawn from each animal. Expression levels of SEAP activity were measured using Novabright Phospha-Light EXP Assay kit for SEAP (secreted placental alkaline phosphatase) Reporter Gene Detection (N10578) (Thermo Fisher) following the manufacturers protocol.

First, the serum samples were heat inactivated at 56° C. for 30 minutes. The samples were then diluted 1:2 in PBS. In a 96 well plate, 12.5 μl of serum samples and 12.5 μl PBS were added in duplicate. A standard curve was set up using recombinant SEAP protein (InvivoGen). Naïve mouse serum was diluted 1:2 in PBS and added to a separate 96 well plate. SEAP protein was added to the first well for a final concentration of 100 μg/well. The control serum was then diluted 1:2 for a 15-point standard curve. 25 μl of each standard was added to the assay plate. 50 μl of a mixture of a non-placental alkaline phosphatase inhibitors ("Component A") was added to each well of the plate and the plate was incubated at 65° C. for 5 minutes. Next 50 μl a composition including a CSPD® substrate and Emerald-III™ luminescence enhancer ("Component B") was then added to each well and the plate was incubated at room temperature in the dark for 17 minutes. Luminescence was read using a Versa Max plate reader. Serum SEAP concentrations for each sample was calculated using linear regression in Graphpad Prism.

Representative day 1 serum SEAP titers are shown in FIG. 1. As shown in FIG. 1, SEAP expression was comparable for LNP 9, LNP 10, LNP 11, and LNP 13, indicating that the addition of ester moieties in the cationic lipid component of the LNP did not adversely impact mRNA expression for LNP 9, LNP 10, LNP 11, or LNP 13.

Example 11: In Vivo Evaluation of SEAP mRNA LNP Compositions with Different Cationic Components Female Balb/C (CRL) mice (6-8 weeks old; N=10 mice per group) were given 100 μl intramuscular (IM, 50 μl per quad) injections of secreted placental alkaline phosphatase ("SEAP") mRNA formulated in LNPs (i.e., mRNA-LNPs). mRNA-LNPs were prepared by the process described in Example 9, with LNP compositions as indicated in Table II above.

As shown in Table IV, Groups 1-4 compare LNP 3, LNP 6, LNP 8, and LNP 12 at a dose of 1.0 μg SEAP mRNA.

TABLE IV

| Group | SEAP mRNA (μg) | LNP Number |
|---|---|---|
| 1 | 1.0 | 3 |
| 2 | 1.0 | 6 |
| 3 | 1.0 | 8 |
| 4 | 1.0 | 12 |

Animals were inoculated once. On day 1, blood was drawn from each animal. Expression levels of SEAP activity were measured using Novabright Phospha-Light EXP Assay kit for SEAP (secreted placental alkaline phosphatase) Reporter Gene Detection (N10578) (Thermo Fisher) following the manufacturers protocol.

First, the serum samples were heat inactivated at 56° C. for 30 minutes. The samples were then diluted 1:2 in PBS. In a 96 well plate, 12.5 μl of serum samples and 12.5 μl PBS were added in duplicate. A standard curve was set up using recombinant SEAP protein (InvivoGen). Naïve mouse serum was diluted 1:2 in PBS and added to a separate 96 well plate. SEAP protein was added to the first well for a final concentration of 100 μg/well. The control serum was then diluted 1:2 for a 15-point standard curve. 25 μl of each standard was added to the assay plate. 50 μl of a mixture of non-placental alkaline phosphatase inhibitors ("Component A") was added to each well of the plate and the plate was incubated at 65° C. for 5 minutes. Next 50 μl a composition including a CSPD® substrate and Emerald-III™ luminescence enhancer ("Component B") was added to each well and the plate was incubated at room temperature in the dark for 17 minutes. Luminescence was read using a Versa Max plate reader. Serum SEAP concentrations for each sample was calculated using linear regression in Graphpad Prism.

Figure 2A:
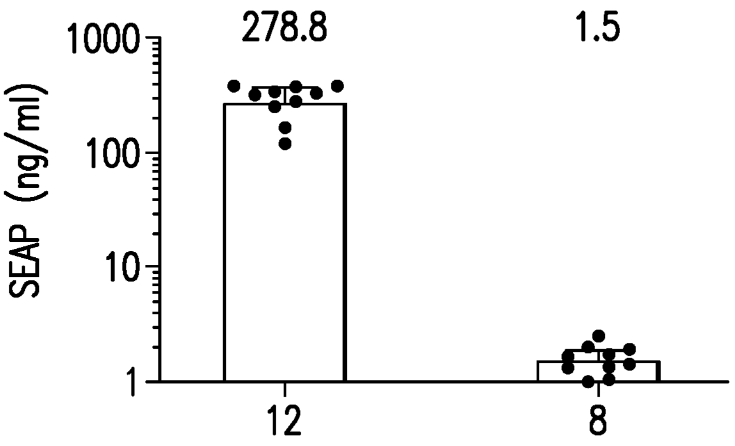
FIGS. 2A and 2B are graphs depicting SEAP expression of LNP 3, 6, 8, and 12 of the present invention.
Figure 2B:
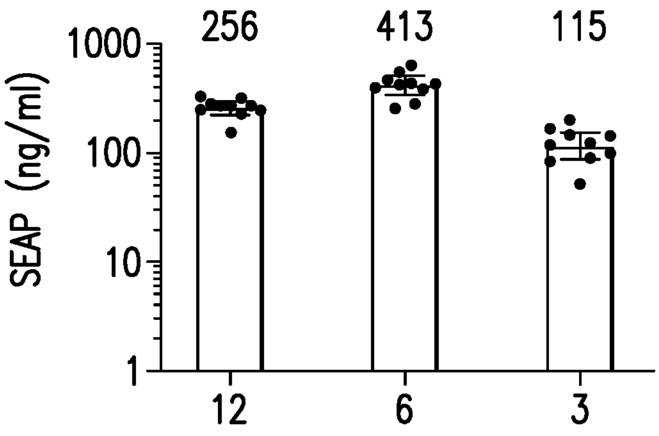

Representative day 1 serum SEAP titers are shown in FIGS. 2A and 2B. As shown in FIG. 2B, SEAP expression was comparable for LNP 3, LNP 6, and LNP 12, but significantly reduced for LNP 8, which is shown in FIG. 2A, indicating that the addition of ester moieties in the cationic lipid component of the LNP did impact mRNA expression for LNP Composition 8 when compared to LNP 3, LNP 6, and LNP 12.

The data from Examples 10 and 11 demonstrated that the presence of an ester group in a cationic lipid of the LNP alone does not predict the impact on mRNA expression. Instead, it is clear that some modifications retain expression (e.g., utilizing the cationic lipids of LNP 3, LNP 6, LNP 9, LNP 10, or LNP 13) while others, such as utilizing the cationic lipid of LNP 8, negate it.

Example 12: In Vivo Evaluation of Cationic Lipid Half-Life at Site of Administration as Component of mRNA LNP Compositions The terminal half-life of elimination (t½) of cationic lipids at the site of administration, when administered as a component of lipid nanoparticle compositions via the intramuscular route, was evaluated in animals. Nanoparticle formulations selected for study are indicated in Table V below.

Up to fifteen rats (approximately 9-10 weeks old; N=1-3 rats per time point group) were given 400 μl intramuscular (IM, 200 μl per quad) injections of RSV F mRNA formulated in LNPs (mRNA-LNPs). mRNA-LNPs were prepared by the process described in Example 9. At least one animal was sacrificed at each of the 3-5 time points (up to 504 hr post-dose). Terminal samples were collected from blood and tissues including muscles around the injection sites. Plasma samples were obtained following centrifugation of blood. Tissue samples were homogenized in the presence homogenization buffer consisting of Tris buffer, sucrose, and a non-selective protease inhibitor 4-(2-aminoethyl)benzenesulfonyl fluoride. The concentrations of cationic lipids in plasma and tissue samples were determined by a LC-MS/MS assay following a protein precipitation step and addition of an appropriate internal standard (labetalol, imipramine, or diclofenac). Quantification was performed by determining peak area-ratios of the cation lipids to the internal standard.

Pharmacokinetic parameters were obtained using non-compartmental methods (Phoenix®). The area under the drug concentration-time curve (AUC0-t) was calculated from the first time point (0 min) up to the last time point with measurable drug concentration using the linear trapezoidal or linear/log-linear trapezoidal rule. The terminal half-life of elimination (t½) was determined by unweighted linear regression analysis of the log-transformed data. The time points for determination of half-life were selected by visual inspection of the data. Values for terminal half-life of elimination (t½) for cationic lipids are shown in Table V below.

TABLE V

| LNP Number* | Cationic Lipid Chemical name | IM $t_{1/2}$ (hours) |
|---|---|---|
| 3 | (Z)-non-2-en-1-yl 10-(2-(dimethylamino)ethyl)nonadecanoate | 7.3 |
| 6 | (Z)-oct-2-en-1-yl 11-(2-(dimethylamino)ethyl)icosanoate | 7.4 |
| 8 | methyl (Z)-18-(2-(dimethylamino)ethyl)heptacos-7-enoate | 5.5 |
| 9 | di((Z)-non-2-en-1-yl) 9-((4-(dimethylamino)butanoyl)oxy)heptadecanedioate | 5.2 |
| 10 | dimethyl (9Z,28Z)-19-((4-(dimethylamino)butanoyl)oxy)heptatriaconta-9,28-dienedioate | 9.2 |
| 11 | di-tert-butyl (9Z,28Z)-19-((4-(dimethylamino)butanoyl)oxy)heptatriaconta-9,28-dienedioate | 90 |
| 12 | (13Z,16Z)-N,N-dimethyl-3-nonyldocosa-13,16-dien-1-amine | >250 |
| 13 | (6Z,9Z,28Z,31Z)-heptatriaconta-6,9,28,31-tetraen-19-yl 4-(dimethylamino)butanoate | >250 |

All LNP compositions consisted of cationic lipid (as indicated in Table V), plus cholesterol, DSPC (1,2-Distearoyl-sn-glycero-3-phosphocholine), and PEG-lipid (α-[8'-(1,2-Dimyristoyl-3-propanoxy)-carboxamide-3', 6'-Dioxaoctanyl]carbamoyl-co-methyl-poly(ethylene glycol), also known as PEG2000-DMG) at molar ratio of 58:30:10:2, respectively.

As shown in Table V, the terminal half-life of elimination (t½) of cationic lipids at the site of administration, when administered as a component of lipid nanoparticle compositions via the intramuscular route, was decreased for ester-containing cationic lipids. Ester-containing cationic lipids (i.e., LNPs 3, 6, and 9-11) were more rapidly eliminated from the site of administration relative to non-ester containing cationic lipids (i.e., LNPs 12 and 13). As shown by the data, the terminal half-life of elimination was lipid-specific; notably not all ester modified lipids were equally rapidly cleared.

Example 13: In Vivo Evaluation of Tolerability of mRNA Lipid Nanoparticle Compositions Crl:CD(SD) rats, approximately 9-11 weeks of age at study start, were assigned to groups of up to 10 males and each received a 50 μg/dose of RSV F mRNA formulated in LNPs (mRNA-LNP), which were diluted in phosphate buffered saline prior to injection, or a control group, which were injected with PBS only. The mRNA-LNPs were prepared by the process described in Example 9. Each animal received 0.20 mL of the respective mRNA-LNP test or PBS control injection in the left quadriceps followed by 0.20 mL of the same formulation in the right quadriceps for a total daily dose of 0.4 mL. Five males/group were designated for final necropsy on Study Day 3 (SD 3) and/or 5 males/group were designated for recovery sacrifice on Study Day 8 (SD 8). Assessment of tolerability was based on unscheduled deaths, clinical observations, body weights, clinical pathology evaluations (serum biochemistry and special chemistry, and limited anatomic pathology evaluations (left quadriceps muscle and overlying skin). In general, animals were anesthetized under isoflurane to effect prior to dose administration and injection sites will be marked with indelible ink (single dot~4 mm proximal above injection site).

Figure 3A:
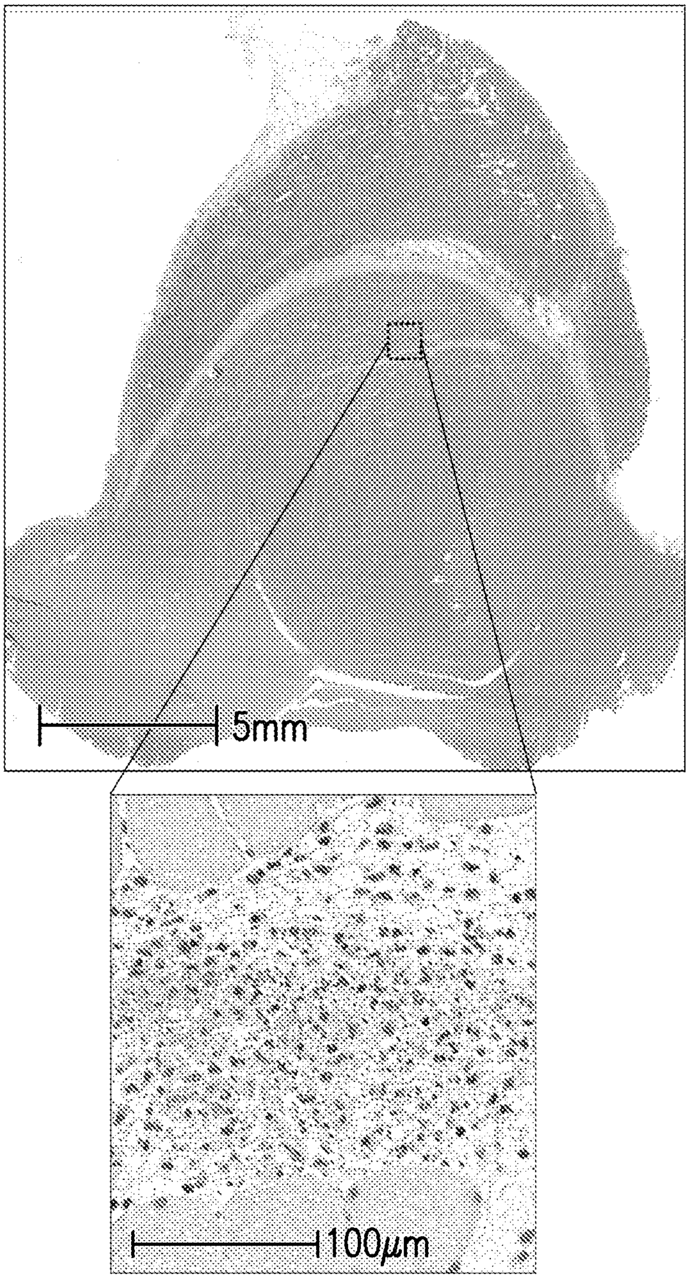
FIGS. 3A and 3B depict histopathology graphs that characterize LNP 13 of the present invention.
Figure 3B:
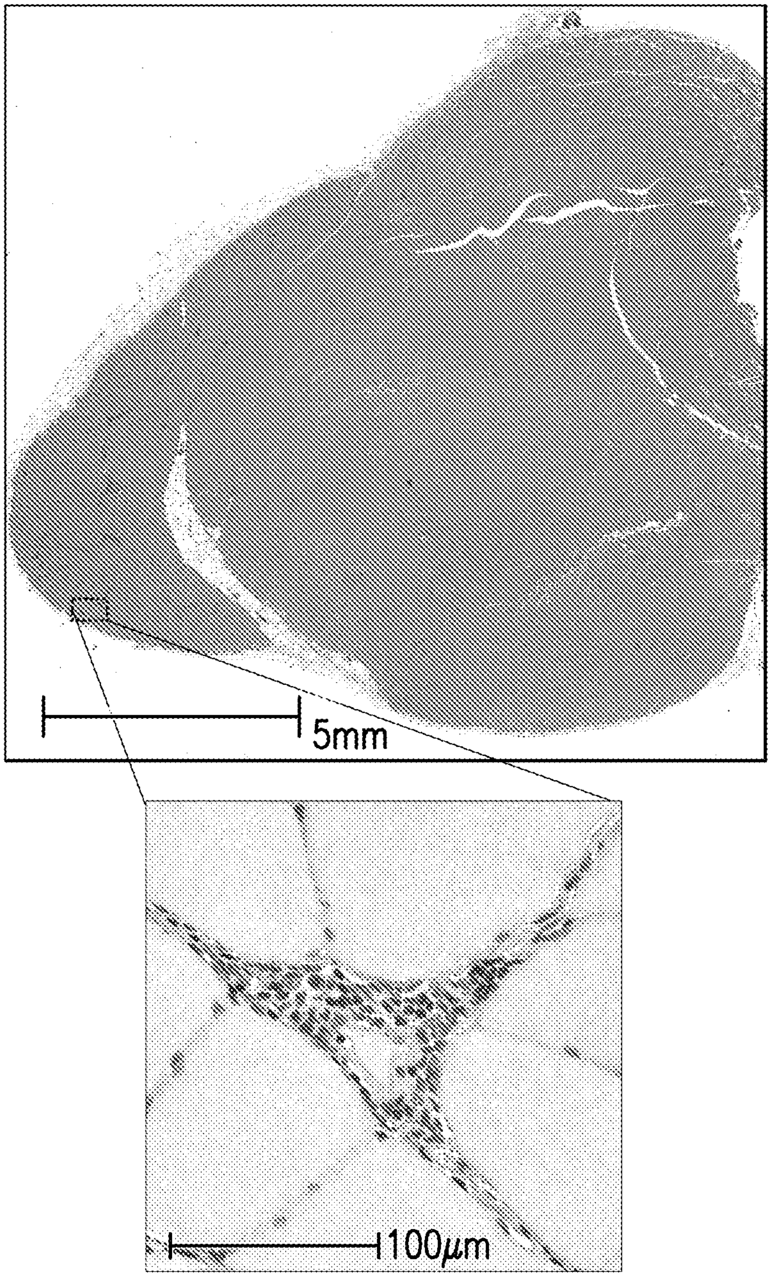

LNP 13 is characterized by histopathology graphs as shown in FIGS. 3A and 3B. As shown in FIG. 3A, mild to moderate acute inflammation of the muscle was observed on Study Day 3 and characterized by granulocytic infiltrates, cellular debris, and edema in the connective tissue surrounding the myofibers. As shown in FIG. 3B, minimal chronic inflammation of the muscle at the injection site was observed on Study Day 8 and characterized by rare, degenerated myocytes surrounded by mononuclear inflammatory cells.

Figure 4A:
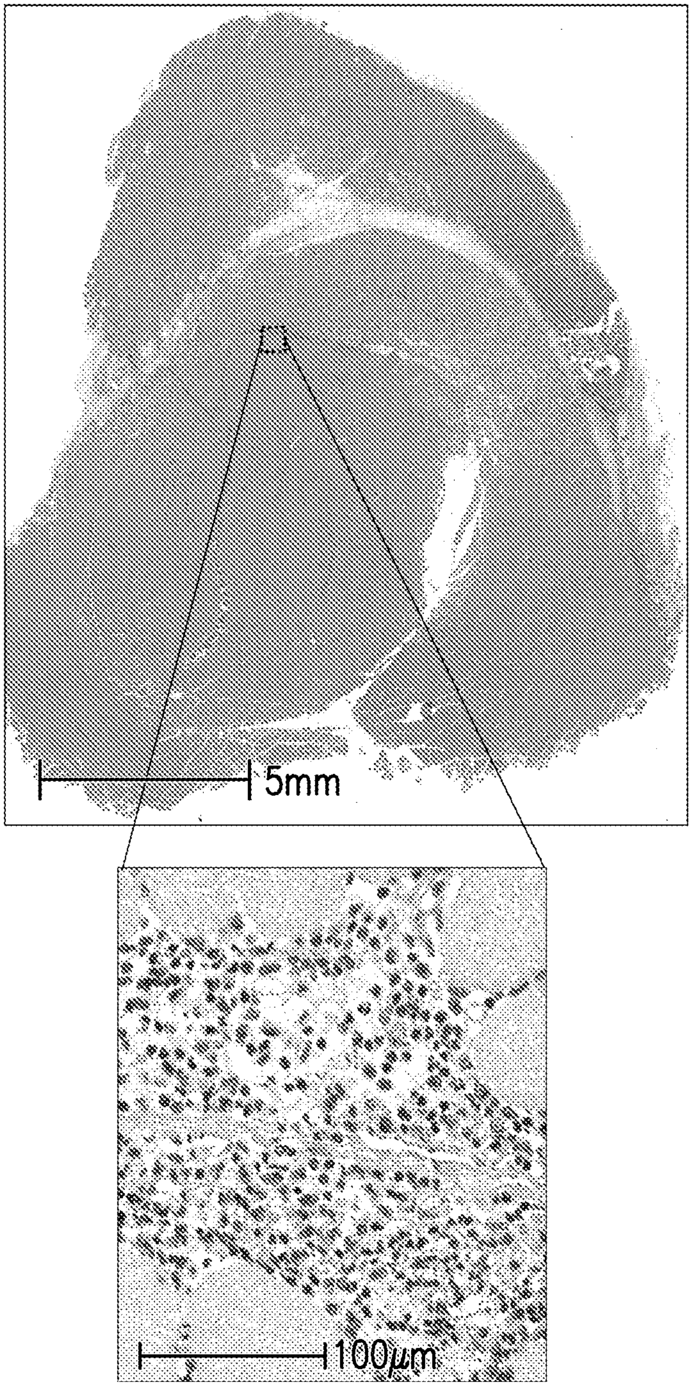
FIGS. 4A and 4B depict histopathology graphs that characterize LNP 9 of the present invention.
Figure 4B:
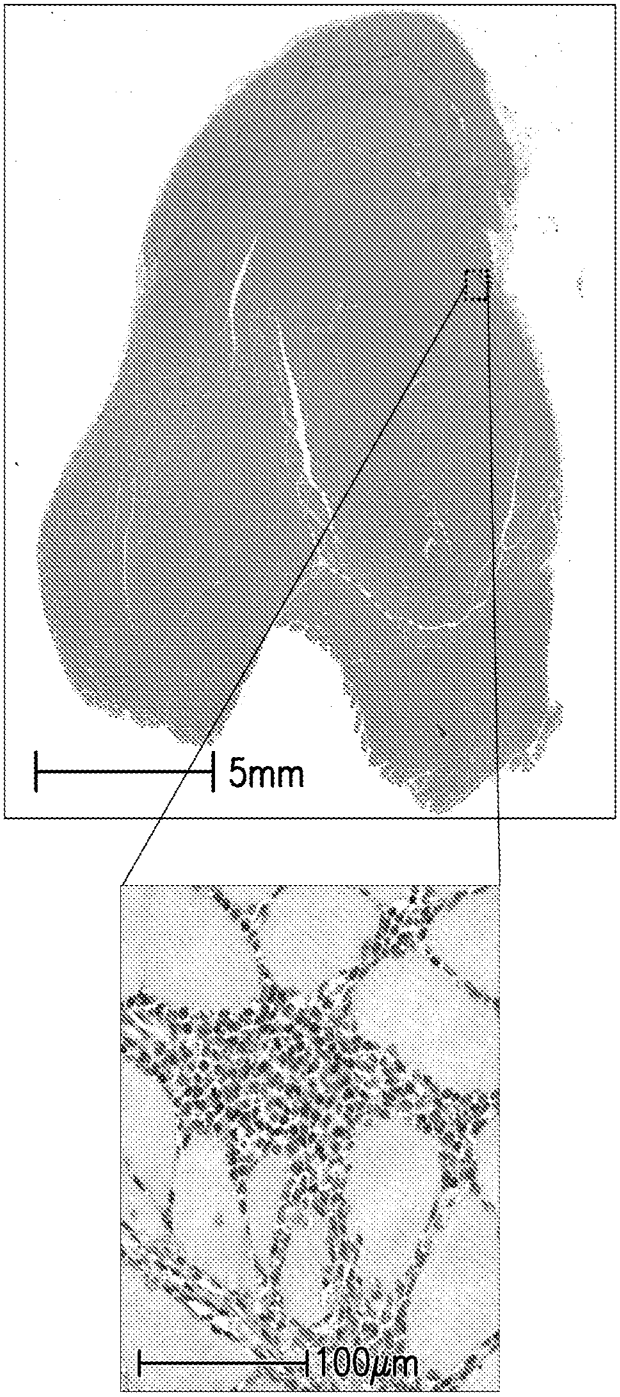

LNP 9 is characterized by histopathology graphs as shown in FIGS. 4A and 4B. As shown in FIG. 4A, moderate acute inflammation was observed on Study Day 3 and consisted of expansion of connective tissues that surrounds myofibers, muscle bundles, and blood vessels by edema, granulocytes, and macrophages and chronic inflammation was observed on Study Day 8 and characterized by myofibers and muscle bundles surrounded by minimal mononuclear inflammatory cells, as shown in FIG. 4B.

Figure 5A:
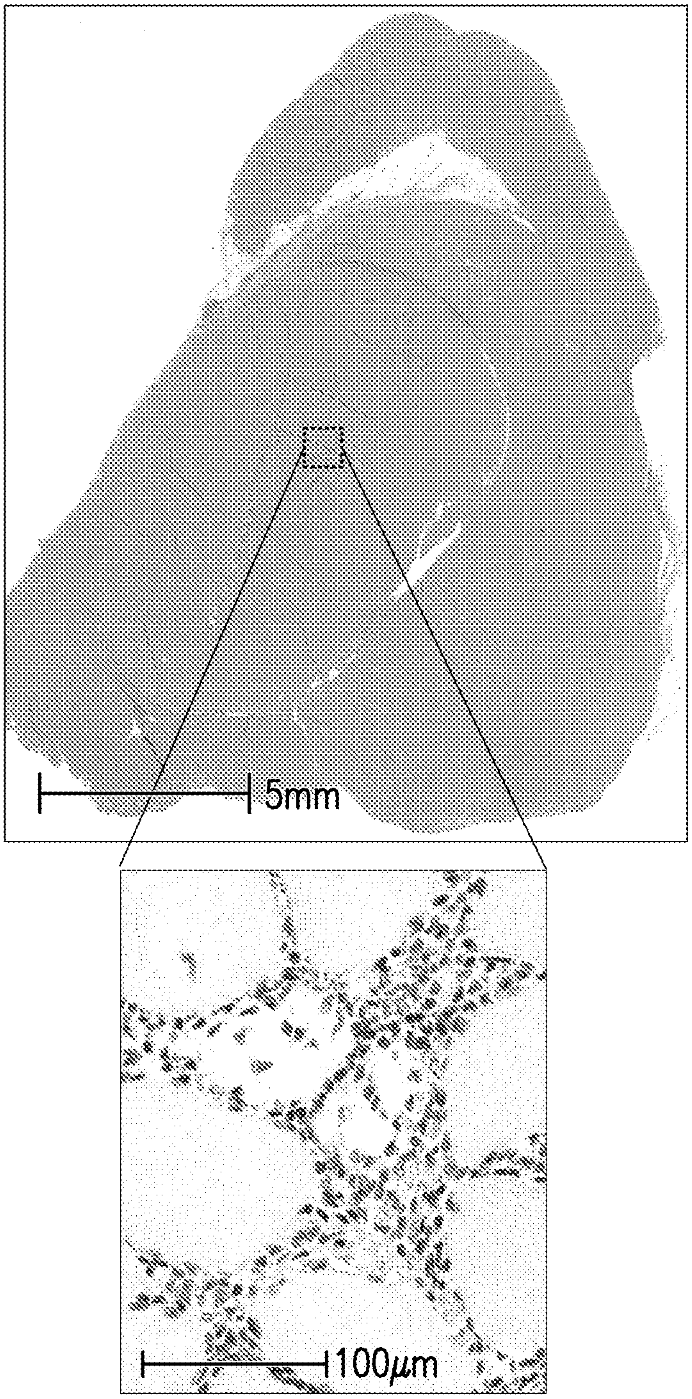
FIGS. 5A and 5B depict histopathology graphs that characterize LNP 10 of the present invention.
Figure 5B:
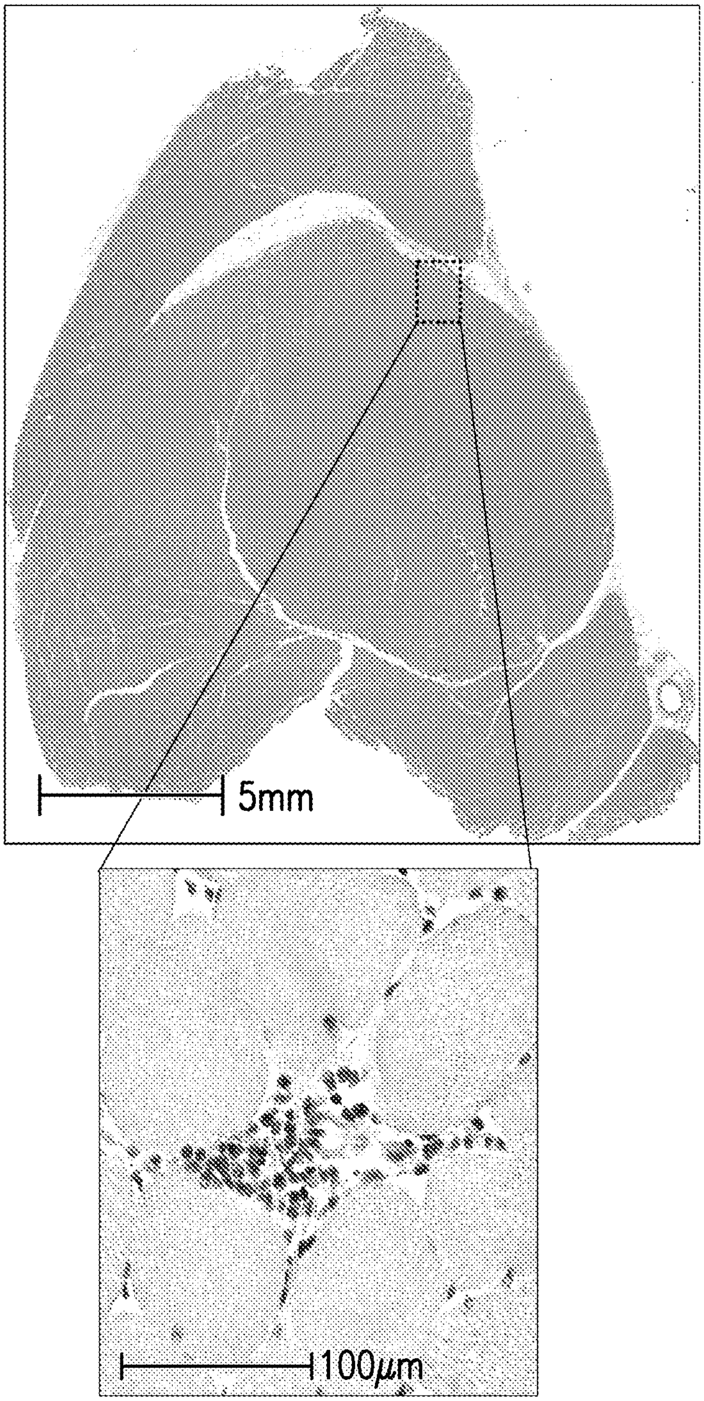

LNP 10 is characterized by histopathology graphs as shown in FIGS. 5A and 5B. As shown in FIG. 5A, mild acute inflammation was observed on Study Day 3 and characterized by myofiber degeneration and inflammatory cells within the connective tissue that separated the muscle bundles and myofibers and minimal chronic inflammation was observed on Study Day 8 and characterized by occasional mononuclear cellular infiltrates between the adjacent myofibers, as shown in FIG. 5B.

Figure 6A:
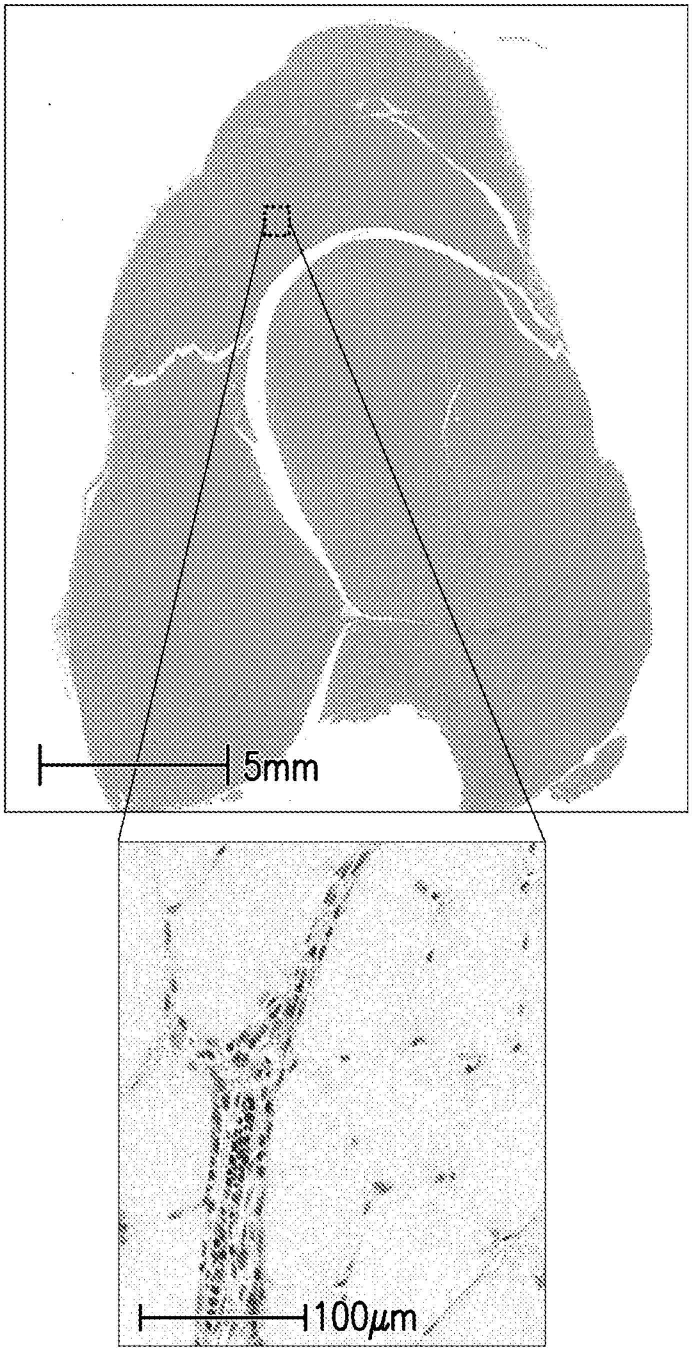
FIGS. 6A and 6B depict histopathology graphs that characterize LNP 3 of the present invention.
Figure 6B:
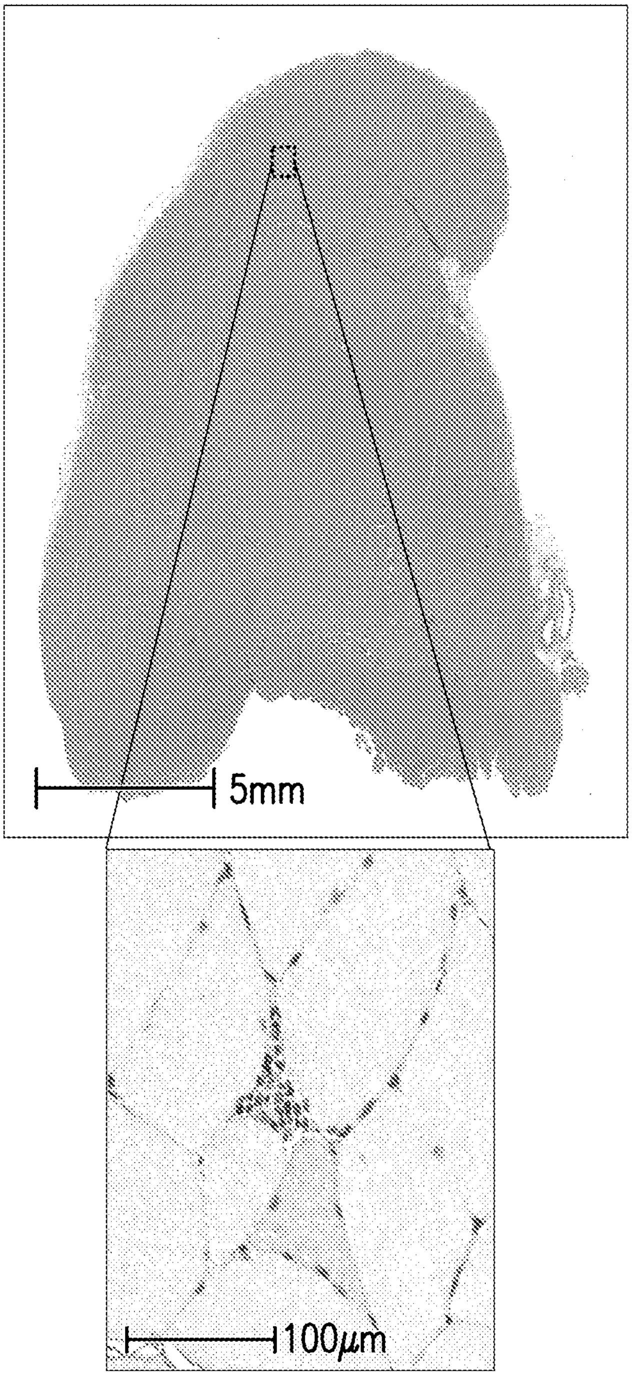

LNP 3 is characterized by histopathology graphs as shown in FIGS. 6A and 6B. As shown in FIG. 6A, minimal inflammation was observed on Study Day 3 and consisted of multifocal mononuclear cell infiltration in connective tissue surrounding myofibers, muscle bundles, and blood vessels and the severity and character of inflammation was similar to that observed in the quadriceps muscle on SD 3 on Study Day 8, as shown in FIG. 6B.

Figure 7A:
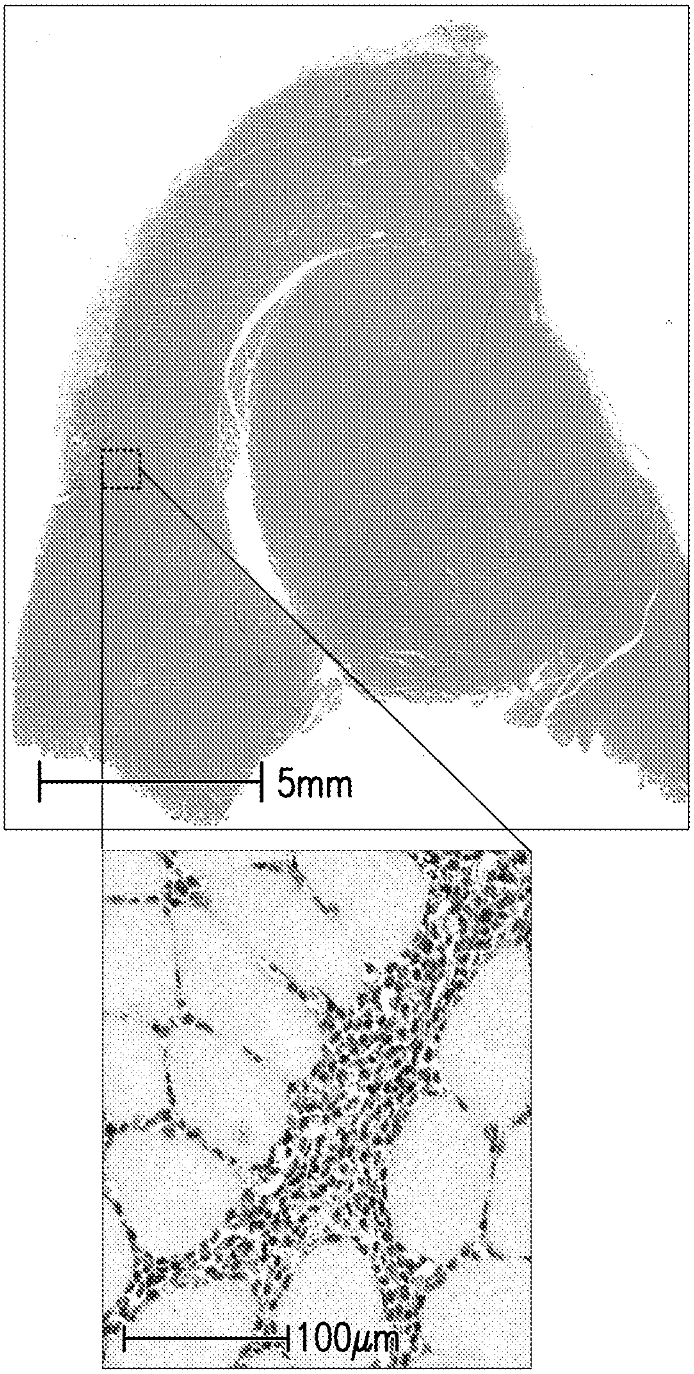
FIGS. 7A and 7B depict histopathology graphs that characterize LNP 6 of the present invention.
Figure 7B:
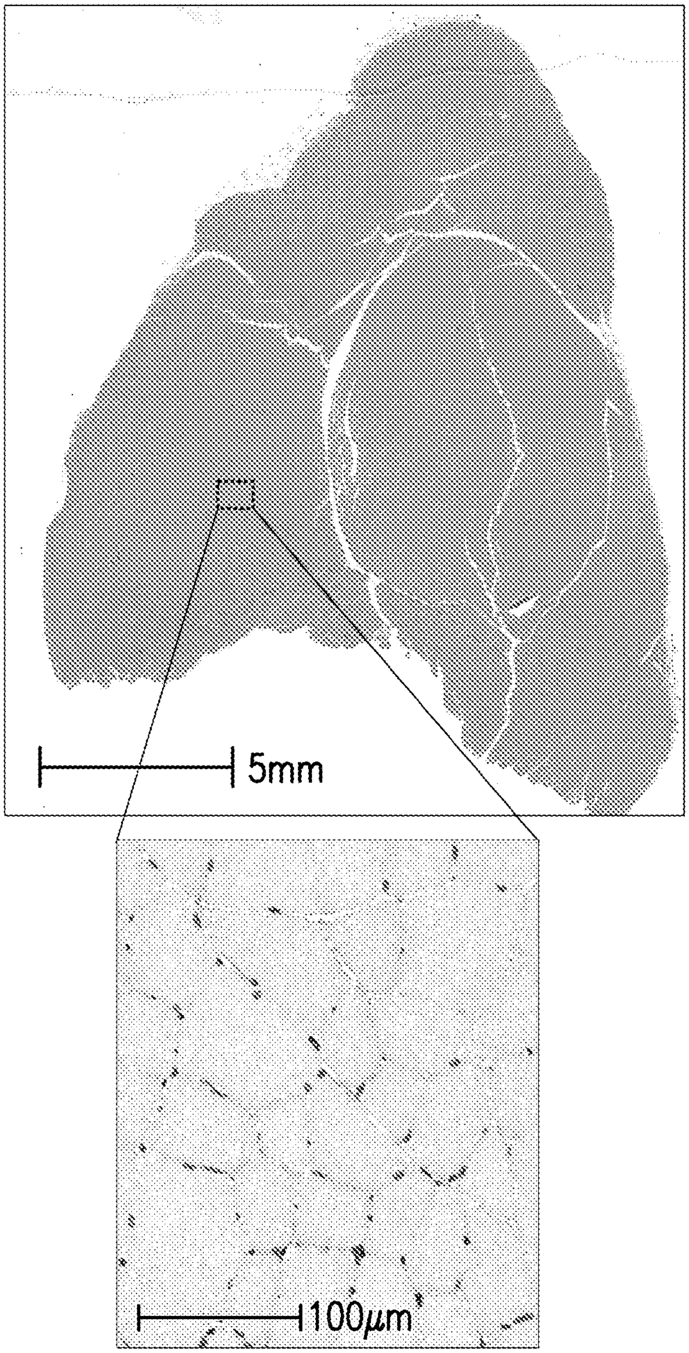

LNP 6 is characterized by histopathology graphs as shown in FIGS. 7A and 7B. As shown in FIG. 7A, minimal acute inflammation was observed on Study Day 3 and characterized by very small, focal infiltration of granulocytes and mononuclear cells within the connective tissue and around individual swollen myofibers and there was no evidence of inflammatory changes observed in the muscle on Study Day 8, as shown in 7B.

Figure 8A:
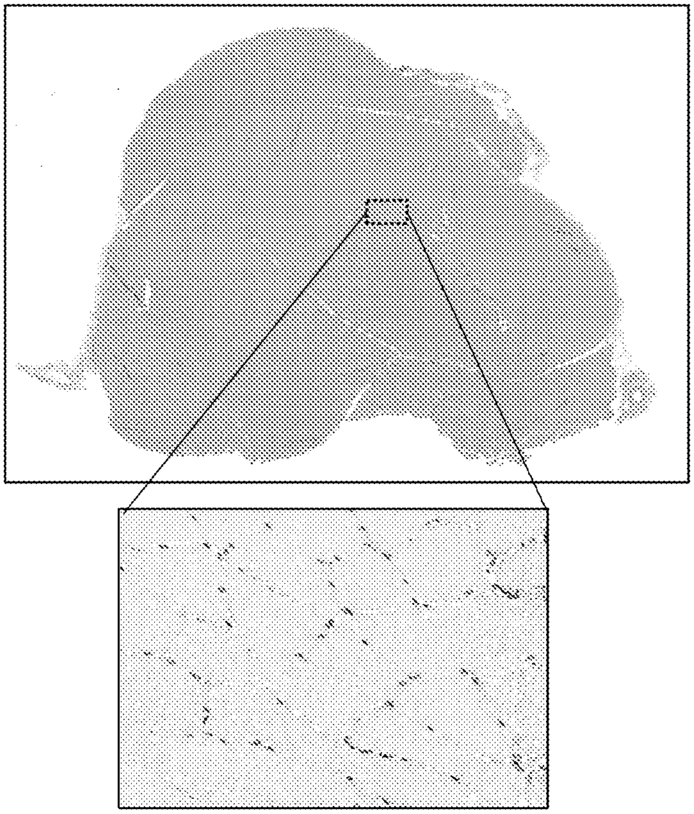
FIGS. 8A and 8B depict histopathology graphs that characterize controls used in Example 13 of the present invention.
Figure 8B:
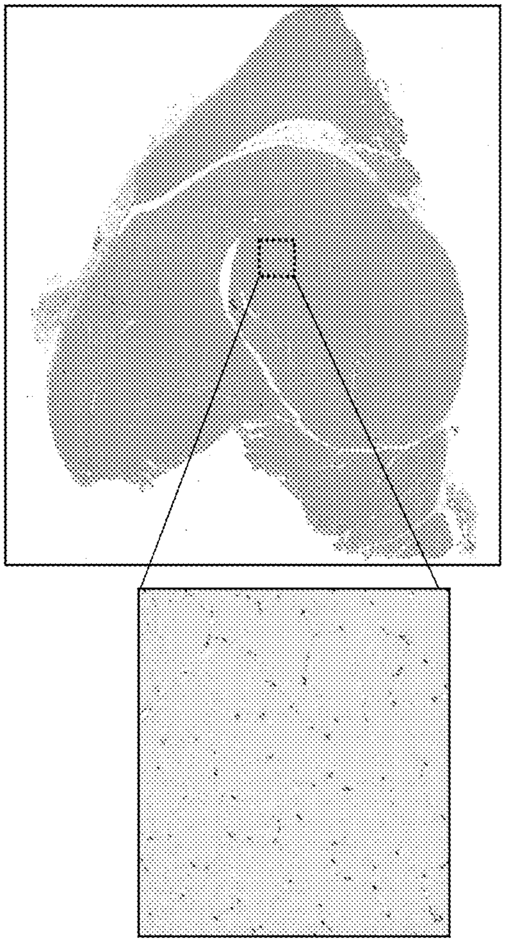

The control group, PBS only, is characterized by histopathology graphs shown in FIGS. 8A and 8B. As shown in FIG. 8A, there are normal myocytes lined by a delicate layer of connective tissues and there is no evidence of inflammation at Study Day 3. Similarly, as shown in FIG. 8B, there is no evidence inflammation at Study Day 8.

As shown from the data in Table V and FIGS. 6A-B and 7A-B, LNP 3 and LNP 6 are indicative of LNP compositions providing improved tolerability relative to other LNP compositions. The data also indicates that the improved tolerability is unique to LNP 3 and LNP 6, which are composed of (Z)-non-2-en-1-yl 10-(2-(dimethylamino)ethyl)nonadecanoate and (Z)-oct-2-en-1-yl 11-(2-(dimethylamino)ethyl)icosanoate cationic lipids respectively, and not generalizable to LNP compositions composed of other ester-containing lipids.

What is claimed:

1. A composition comprising:

a polynucleotide; and a lipid nanoparticle (LNP) comprising:

(a) a monoester cationic lipid selected from the group consisting of:

(Z)-non-2-en-1-yl 10-(2-(dimethylamino) ethyl) nonadecanoate; and (Z)-oct-2-en-1-yl 11-(2-(dimethylamino) ethyl) icosanoate;

(b) a phospholipid;

(c) cholesterol; and (d) α-[8'-(1,2-dimyristoyl]-3-propanoxy)-carboxyamide-3',6'-dioxaoctanyl]carbamoyl-ωmethyl-poly (ethylene glycol) (PEG2000-DMG);

wherein the polynucleotide is at least partially encapsulated in the LNP; and wherein the monoester cationic lipid has a terminal half-life of elimination of less than 100 hours following intramuscular administration of the composition to a subject.

2. The composition of claim 1, wherein the LNP comprises 30-65 mole % monoester cationic lipid, 5-30 mole % phospholipid, 10-40 mole % cholesterol, and 0.5-4 mole % PEG2000-DMG.

3. The composition of claim 2, wherein the LNP comprises 55-65 mole % monoester cationic lipid, 5-15 mole % phospholipid, 25-35% cholesterol, and 1-2.5 mole % PEG2000-DMG.

4. The composition of claim 1, wherein the phospholipid is 1,2-distearoyl-sn-glycero-3-phosphocholine (DSPC).

5. The composition of claim 4, wherein the DSPC is present in the amount of about 5-15 mole %.

6. The composition of claim 1, wherein the PEG2000-DMG is present in the amount of about 5-15 mole %.

7. The composition of claim 1, further comprising:

a buffer.

* * * * *